(12) United States Patent
Egan et al.

(10) Patent No.: US 7,932,099 B2
(45) Date of Patent: Apr. 26, 2011

(54) METHODS AND COMPOSITIONS FOR ANALYTE DETECTION

(75) Inventors: Richard Laswell Egan, Oceanside, CA (US); Graham Peter Lidgard, La Jolla, CA (US); David Dickson Booker, Oceanside, CA (US); Christopher Johann Johnson, San Diego, CA (US)

(73) Assignee: Nexus DX, Inc., San Diego, CA (US)

( * ) Notice: Subject to any disclaimer, the term of this patent is extended or adjusted under 35 U.S.C. 154(b) by 301 days.

(21) Appl. No.: 11/677,559

(22) Filed: Feb. 21, 2007

(65) Prior Publication Data

US 2008/0199851 A1 Aug. 21, 2008

Related U.S. Application Data

(60) Provisional application No. 60/775,649, filed on Feb. 21, 2006, provisional application No. 60/789,345, filed on Apr. 5, 2006, provisional application No. 60/866,932, filed on Nov. 22, 2006.

(51) Int. Cl.
*G01N 33/53* (2006.01)

(52) U.S. Cl. ....... 436/514; 435/7.1; 435/7.5; 435/287.1; 435/287.2; 435/287.7; 435/810; 436/518; 436/808; 436/810; 422/58; 422/61

(58) Field of Classification Search ............. 435/7.1, 435/7.5, 287.1, 287.2, 287.7, 810; 436/514, 436/518, 808, 810
See application file for complete search history.

(56) References Cited

U.S. PATENT DOCUMENTS

| | | | |
|---|---|---|---|
| 4,366,225 A | 12/1982 | Kosinski | |
| 4,707,450 A * | 11/1987 | Nason | 600/572 |
| 4,857,453 A * | 8/1989 | Ullman et al. | 435/7.92 |
| 4,943,522 A * | 7/1990 | Eisinger et al. | 435/7.25 |
| 4,978,504 A * | 12/1990 | Nason | 422/61 |
| 5,073,484 A | 12/1991 | Swanson et al. | |
| 5,078,968 A | 1/1992 | Nason | |
| 5,238,649 A | 8/1993 | Nason | |
| 5,266,266 A | 11/1993 | Nason | |
| 5,415,994 A | 5/1995 | Imrich et al. | |
| 5,716,778 A | 2/1998 | Weng et al. | |
| 5,798,273 A | 8/1998 | Shuler et al. | |
| 5,837,466 A | 11/1998 | Lane et al. | |
| 6,083,695 A * | 7/2000 | Hardin et al. | 506/5 |
| 6,235,539 B1 | 5/2001 | Carpenter | |

(Continued)

FOREIGN PATENT DOCUMENTS

WO WO 01/13126 * 2/2001

(Continued)

OTHER PUBLICATIONS

Corstjens, et al. Use of up-converting phosphor reporters in lateral-flow assays to detect specific nucleic acid sequences: a rapid, sensitive DNA test to identify human papillomavirus type 16 infection. Clin Chem. Oct. 2001;47(10):1885-93.

(Continued)

*Primary Examiner* — Bao-Thuy L Nguyen
(74) *Attorney, Agent, or Firm* — Cooley, LLP

(57) ABSTRACT

The present invention is directed to methods and apparatus for detection of one or more analytes. Analytes include agents or components of infectious agents such as pathogenic virus, as well as enzymes, proteins and biomarkers.

29 Claims, 31 Drawing Sheets

U.S. PATENT DOCUMENTS

| | | |
|---|---|---|
| 6,236,639 B1 | 5/2001 | Selg et al. |
| 6,267,722 B1 | 7/2001 | Anderson et al. |
| 6,297,060 B1 | 10/2001 | Nowakowski et al. |
| 6,375,896 B1 | 4/2002 | Wuske et al. |
| 6,448,001 B2 | 9/2002 | Oku et al. |
| 6,485,982 B1 | 11/2002 | Charlton |
| 6,565,808 B2 | 5/2003 | Hudak et al. |
| 6,593,085 B1 | 7/2003 | Barnett et al. |
| 6,656,744 B2 | 12/2003 | Pronovost et al. |
| 6,719,691 B2 | 4/2004 | Kritzman et al. |
| 6,811,971 B2 | 11/2004 | Klepp et al. |
| 6,887,362 B2 * | 5/2005 | Huang et al. ............ 506/32 |
| 2004/0014094 A1 | 1/2004 | Lee et al. |
| 2004/0171174 A1 * | 9/2004 | Nazareth et al. ............ 436/514 |
| 2004/0197793 A1 | 10/2004 | Hassibi et al. |
| 2004/0197845 A1 | 10/2004 | Hassibi et al. |
| 2005/0130120 A1 | 6/2005 | Lambotte et al. |
| 2005/0136553 A1 | 6/2005 | Kaylor et al. |
| 2006/0040405 A1 | 2/2006 | Charlton et al. |
| 2007/0161078 A1 | 7/2007 | Lu et al. |
| 2008/0254999 A1 | 10/2008 | Kachab et al. |

FOREIGN PATENT DOCUMENTS

| | | |
|---|---|---|
| WO | WO 2005/031355 A1 | 4/2005 |

OTHER PUBLICATIONS

Hashida, et al. Detection of one attomole of [Arg8]-vasopressin by novel noncompetitive enzyme immunoassay (hetero-two-site complex transfer enzyme immunoassay). J Biochem. Oct. 1991;110(4):486-92.

* cited by examiner

FIGURE 21

[Graph: Fluorescence signal vs Distance (1/10 mm), peak near 225, labeled "0.41 HA unit Hong Kong 5/72 Flu B"]

FIGURE 22

[Graph: Fluorescence signal vs Distance (1/10 mm), labeled "16.3 µL H5N1", "Flu A" peak near 175, "subtype H5" near 275]

FIGURE 23

[Graph: Fluorescence signal vs Distance (1/10 mm), labeled "40 ng HA activity", "Flu A" peak near 175]

Test strips with subtype H5N1 viruses

Sensitivity of Nanogen Influenza A Test with pRNA capture system
0.75 mg/ml membrane without blocking Sensitivity of Nanogen Influenza A Test HA units/test
Influenza A/Texas/1/77

SEQUENCE LISTING

<160> NUMBER OF SEQ ID NOS: 114

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggttcagc tgcagcagtc tggagctgag ctgatgaagc ctggggcctc agtgaagata    60
tcctgcaagg ctactggcta cactttcagt aactactgga tagagtggat aaagcagagg   120
cctggacatg gccttgagtg gattggagag attttacctg gaagcgatag aacaaactac   180
aatgggaagt tcaagggcaa ggccacattc actgcagata catcctccaa cacagcccac   240
atgcaactca gtagcctgac atctgaggac tctgccgtct attactgtgc aaatagatac   300
gacgggtatt attttggttt ggattactgg ggtcaaggaa cctcagtcgc cgtctcctca   360
gcc                                                                  363

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Asp Arg Thr Asn Tyr Asn Gly Lys Phe
    50                  55                  60

Lys Gly Lys Ala Thr Phe Thr Ala Asp Thr Ser Ser Asn Thr Ala His
65                  70                  75                  80

Met Gln Leu Ser Ser Leu Thr Ser Glu Asp Ser Ala Val Tyr Tyr Cys
                85                  90                  95

Ala Asn Arg Tyr Asp Gly Tyr Tyr Phe Gly Leu Asp Tyr Trp Gly Gln
            100                 105                 110

Gly Thr Ser Val Ala Val Ser Ser Ala
        115                 120

<210> SEQ ID NO 3
<211> LENGTH: 321
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 3
gaaatcgtgc tcacccagtc tccagcaatc atgtctgcat ctctagggga gaaggtcacc      60
atgagctgca gggccagctc aagtgtaaat tcgtttact ggtaccagca gaggtcagat     120
gcctccccca aactattgat ttactattca tccaacctgg ctcctggagt cccacctcgc    180
ttcagtggca gtgggtctgg aactcttat tctctcacaa tcagcggctt ggagggtgaa    240
gatgctgcca cttattactg ccagcacttt actagttccc cgtacacgtt cggaggggg     300 accaacctgg aaataaaacg g                                               321

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Phe Val
            20                  25                  30

Tyr Trp Tyr Gln Gln Arg Ser Asp Ala Ser Pro Lys Leu Leu Ile Tyr
        35                  40                  45

Tyr Ser Ser Asn Leu Ala Pro Gly Val Pro Pro Arg Phe Ser Gly Ser
    50                  55                  60

Gly Ser Gly Asn Ser Tyr Ser Leu Thr Ile Ser Gly Leu Glu Gly Glu
65                  70                  75                  80

Asp Ala Ala Thr Tyr Tyr Cys Gln His Phe Thr Ser Ser Pro Tyr Thr
                85                  90                  95

Phe Gly Gly Gly Thr Asn Leu Glu Ile Lys Arg
            100                 105

<210> SEQ ID NO 5
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cagatccagt tggtgcagtc tggacctgag ctgaagaagc ctggagagac agtcaagatc      60
tcctgcaagg cctctgggta cagcttcaca aactatggaa tgaactgggt gaagcaggct    120
ccaggaaagg gtctaaagtg gatgggctgg ataaacacct acaccggaga gccagcctat    180
gctgatgact tcaagggacg gtttgccttc tctctggaaa cctctgccag cactgcctat    240
ttgcagatca caaacctcaa aaatgaggac acggctacat atttctgtgc aagatggaat    300
agagatgcta tggactactg gggtcaagga acctcggtca ccgtatctag c             351

<210> SEQ ID NO 6
<211> LENGTH: 117
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Ala Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Asn Arg Asp Ala Met Asp Tyr Trp Gly Gln Gly Thr Ser
            100                 105                 110

Val Thr Val Ser Ser
        115

<210> SEQ ID NO 7
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gacattgtgc tgacccaatc tccagcttct ttggctgtgt ctcttgggca gagggccacc      60
atatcctgca gagccagtga aagtgttgat agttctgaca atagtcttat gcactggtac     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtattgg ggatcctccg     300
tacacgttcg gaggggggac caagctggaa ataaaacgg                            339

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Ser
                20                  25                  30

Asp Asn Ser Leu Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Ile

```
                    85                  90                  95
Gly Asp Pro Pro Tyr Thr Phe Gly Gly Gly Thr Lys Leu Glu Ile Lys
            100                 105                 110

Arg

<210> SEQ ID NO 9
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caggtccaac tgcagcagcc tggggctgaa cttgtgaagc ctggggcttc agtgaagctg      60
tcctgcaagg cttctggcta caccttcacc agctactgga tgcactgggt gaagcagagg     120
cctggacagg ccttgagtg gatcggagag attgatcctt ctgattctta tactaactac      180
aatcagaagt tcaagggcaa ggccacattg actgtagaca atcctccag cacagcctac      240 atgcagctca gcagcctgac atctgaggac tctgcggtct attactgtgc aagggggggt     300
acaggagact ttcactatgc tatggactac tggggtcaag gcacctcggt caccgtatca     360
tcg                                                                   363

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Gly Asp Phe His Tyr Ala Met Asp Tyr Trp Gly
            100                 105                 110

Gln Gly Thr Ser Val Thr Val Ser Ser
        115                 120

<210> SEQ ID NO 11
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gacatcctga tgacccaatc tccatcctcc atgtctgtat ctctgggaga cacagtcagc      60
```

```
atcacttgcc atgcaagtca gggcattagc agtaatatag ggtggttgca gcagaaacca    120
gggaaatcat ttaagggcct gatctatcat ggaaccaact tggaagatgg agttccatca    180
aggttcagtg gcagtggatc tggagcagat tattctctca ccatcagcag cctggaatct    240
gaagattttg cagactatta ctgtgtacag tatgttcagt tcccgtacac gttcggaggg    300
ggcaccaagc tggaaatcaa acgg                                           324
```

```
<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Val Gln Phe Pro Tyr
                85                  90                  95

Thr Phe Gly Gly Gly Thr Lys Leu Glu Ile Lys Arg
            100                 105

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catgggatgc tgccggtgta t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aattctgggc cttggctgac g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tggccgcctc tgtcgaagaa g                                              21
```

<210> SEQ ID NO 16
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caggtccaac tgcagcagcc tggggctgag cttgtgaagc ctggggcttc agtgaacctg      60
tcctgtaagg cttctggcta caccttcacc agctactgga tgcactgggt gaagcagagg     120
cctggacaag gccttgagtg gatcggagag attgatcctt ctgatagttt tactacctac     180
aatcaaaact tcaaagacag ggccacattg actgtagaca atcatccag cacagcctac      240 atgcagctca gaagtctgac atctgaggac tctgcggtct attactgtgc caggggggt     300 ccaggagact tcgctatgc tatggattac tggggccaag gcacctcggt caccgtctcc     360
tca                                                                   363

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Pro Gly Ala Glu Leu Val Lys Pro Gly Ala
1               5                   10                  15

Ser Val Asn Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Asp Ser Phe Thr Thr Tyr Asn Gln Asn Phe
        50                  55                  60

Lys Asp Arg Ala Thr Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Gly Gly Pro Gly Asp Phe Arg Tyr Ala Met Asp Tyr Trp Gly
            100                 105                 110

Gln Gly Thr Ser Val Thr Val Ser Ser
        115                 120

<210> SEQ ID NO 18
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gacatcctga tgacccaatc tccatcctcc atgtctgtat ctctgggaga cacagtcagc      60
atcacttgcc atgcaagtca gggcattagc agtaatatag gtggttgca gcagaaacca     120 gggaaatcat ttaagggcct gatctatcat ggaaccaact ggaagatgg agttccatca      180 aggttcagtg gcagtggatc tggagcagat tattctctca ccatcagcag cctggaatcc     240

```
gaagactttg cagactatta ctgtgtacag tatgttcagt ttccctacac gttcggaggg      300
gggaccaagc tggaaataaa acgggct                                          327
```

<210> SEQ ID NO 19
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Val Gln Phe Pro Tyr
                85                  90                  95

Thr Phe Gly Gly Gly Thr Lys Leu Glu Ile Lys Arg Ala
            100                 105
```

<210> SEQ ID NO 20
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
caggtccaac tgcagcagtc tggggctgag ctggtgaggc ctggggtctc agtgaagatt       60
tcctgcaagg gttctggcta cacattcact gattatgcta tgcattgggt gaagcagagt      120
catgcaaaga gtctagagtg gattggactt attaatactg actatggtga tactacttac      180
aaccagaagt tcaagggcaa ggccacaatg actgtagaca atcctccaa cacagcctat       240 atggaacttg ccagactgac atctgaggat tctgccatct attactgtgc aagatcggac      300
tatgattact atttctgtgg tatggactac tggggtcaag aaccacggt caccgaatct      360 cta                                                                    363
```

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45
```

```
Gly Leu Ile Asn Thr Asp Tyr Gly Asp Thr Thr Tyr Asn Gln Lys Phe
        50                  55                  60

Lys Gly Lys Ala Thr Met Thr Val Asp Lys Ser Ser Asn Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Ser Asp Tyr Asp Tyr Tyr Phe Cys Gly Met Asp Tyr Trp Gly
            100                 105                 110

Gln Gly Thr Thr Val Thr Glu Ser Leu
        115                 120

<210> SEQ ID NO 22
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
caggtgcagc tgaaggagtc aggacctggc ctggtggcgc cctcacagcg cctgtccatc      60
acatgcaccg tctcagggtt ctcattaacc ggctatggtg tacactggat tcgccagtct    120
ccaggaaagg gtctggagtg gctgggaatg atatgggctg agggaagaac cgactataat    180
tcagttctca aatccagact gagcatcaat aaggacaatt ccaggagcca agtttttctta   240 gaaatgaaca gtctgcaaac tgatgacaca gccaggtact actgtgccag agaggtgatt    300
actacggaag cctggtactt cgatgtctgg ggccaaggaa cctcggtcac cgaatct       357

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Lys Glu Ser Gly Pro Gly Leu Val Ala Pro Ser Gln
 1               5                  10                  15

Arg Leu Ser Ile Thr Cys Thr Val Ser Gly Phe Ser Leu Thr Gly Tyr
             20                  25                  30

Gly Val His Trp Ile Arg Gln Ser Pro Gly Lys Gly Leu Glu Trp Leu
         35                  40                  45

Gly Met Ile Trp Ala Glu Gly Arg Thr Asp Tyr Asn Ser Val Leu Lys
     50                  55                  60

Ser Arg Leu Ser Ile Asn Lys Asp Asn Ser Arg Ser Gln Val Phe Leu
 65                  70                  75                  80

Glu Met Asn Ser Leu Gln Thr Asp Thr Ala Arg Tyr Tyr Cys Ala
                 85                  90                  95

Arg Glu Val Ile Thr Thr Glu Ala Trp Tyr Phe Asp Val Trp Gly Gln
            100                 105                 110

Gly Thr Ser Val Thr Glu Ser
        115

<210> SEQ ID NO 24
<211> LENGTH: 324
<212> TYPE: DNA
<213> ORGANISM: Artificial Sequence
<220> FEATURE:
```

-continued

<223> OTHER INFORMATION: Description of Artificial Sequence: Synthetic
      polynucleotide

<400> SEQUENCE: 24
gacattgtga tgactcagtc tccagccacc ctgtctgtga ctccaggaga tagagtctct    60
ctttcctgca gggccagcca gagtattagc gactacttat actggtatca acaaaaatca   120
catgagtctc caaggcttct catcaaatat gcttcccaat ccatctctgg gatcccctcc   180
agattcagtg gcagtggatc agggtcagat ttcactctca ctatcaacag tgtggaacct   240
gaagatgttg gaatgtatta ctgtcaaaat ggtcacacct ttccgctcac gttcggtgct   300
ggcaccaagc tggaaatcaa acgg                                          324

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Thr Ile Asn Ser Val Glu Pro
65                  70                  75                  80

Glu Asp Val Gly Met Tyr Tyr Cys Gln Asn Gly His Thr Phe Pro Leu
                85                  90                  95

Thr Phe Gly Ala Gly Thr Lys Leu Glu Ile Lys Arg
            100                 105

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Tyr Thr Phe Ser Asn Tyr Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Leu Pro Gly Ser Asp Arg Thr
1               5

<210> SEQ ID NO 28
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Asn Arg Tyr Asp Gly Tyr Tyr Phe Gly Leu Asp Tyr
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ser Val Asn Phe
1               5

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ser Ser
1

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln His Phe Thr Ser Ser Pro Tyr Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Tyr Ser Phe Thr Asn Tyr Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Asn Thr His Thr Gly Glu Pro
1               5
```

```
<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Arg Trp Asn Arg Asp Ala Met Asp Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Ser Val Asp Ser Ser Asp Asn Ser Leu
1               5                   10

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser
1

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Ser Ile Gly Asp Pro Pro Tyr Thr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Thr Ser Tyr Trp
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Ile Asp Pro Ser Asp Ser Tyr Thr
1               5

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Gly Gly Thr Gly Asp Phe His Tyr Ala Met Asp Tyr
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gly Ile Ser Ser Asn
1               5

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

His Gly Thr
1

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Tyr Val Gln Phe Pro Tyr Thr
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Thr Phe Thr Ser Tyr Trp
1               5

<210> SEQ ID NO 45
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 45

Ile Asp Pro Ser Asp Ser Phe Thr
1               5

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Gly Pro Gly Asp Phe Arg Tyr Ala Met Asp Tyr
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gly Ile Ser Ser Asn
1               5

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Gly Thr
1

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Gln Tyr Val Gln Phe Pro Tyr Thr
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Tyr Thr Phe Thr Asp Tyr Ala
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Asn Thr Asp Tyr Gly Asp Thr
1               5

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Arg Ser Asp Tyr Asp Tyr Tyr Phe Cys Gly Met Asp Tyr
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Ser Leu Thr Gly Tyr Gly
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Trp Ala Glu Gly Arg Thr
1               5

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Glu Val Ile Thr Thr Glu Ala Trp Tyr Phe Asp Val
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56
```

```
Gln Ser Ile Ser Asp Tyr
1               5
```

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Tyr Ala Ser
1
```

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gln Asn Gly His Thr Phe Pro Leu Thr
1               5
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
His Gly Met Leu Pro Val Tyr
1               5
```

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Pro Pro Ser Asn Tyr Gly Arg
1               5
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Pro Pro Ser Asn Phe Gly Lys
1               5
```

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 62

Gly Asp Pro Trp Phe Thr Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Ser Gly Pro Trp Leu Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Pro Pro Leu Ser Lys Lys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Thr Phe Arg Thr Pro Ile
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Thr Phe Arg Asp Pro Asn
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Pro Ile Trp Thr Lys Leu
1               5

<210> SEQ ID NO 68
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Glu Pro Val Lys Lys Tyr Pro Thr Arg Ser Pro
1               5                   10

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atggagccgg tgaagaagta tccgacgcgt tctcct                              36

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Thr Gln Leu Thr Thr Ala Gly Leu Arg Leu Leu
1               5                   10

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gagactcagc tgactacggc gggtcttcgg ctgctt                              36

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Thr Pro Leu Thr Glu Thr Ala Leu Lys Trp His
1               5                   10

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gagacgcctc ttacggagac ggctttgaag tggcat                              36

<210> SEQ ID NO 74
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Thr Pro Leu Thr Met Ala Ala Leu Glu Leu Phe
1               5                   10

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagacgccgc tgactatggc tgctcttgag cttttt                              36

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Thr Pro Leu Thr Thr Ala Ala Leu Arg Leu Val
1               5                   10

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gatactccgc tgacgacggc ggctcttcgg ctggtt                              36

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Pro Leu Thr Leu Trp Ala Leu Ser Gly Leu Arg
1               5                   10

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acgccgctta cgctttgggc tctttctggg ctgagg                              36
```

```
<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Thr Pro Leu Thr Glu Thr Ala Leu Lys Trp His
1               5                   10

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagacgcctc ttacggagac ggctttgaag tggcat                            36

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Thr Pro Leu Thr Met Ala Ala Leu Glu Leu Leu
1               5                   10

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cagacgcctc tgactatggc ggctcttgag cttctt                            36

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Leu Gln Asp Gly Ser Pro Pro Ser Ser Pro His
1               5                   10

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cagacgcctc tgactatggc ggctcttgag cttctt                            36
```

```
<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly His Val Thr Thr Leu Ser Leu Leu Ser Leu Arg
1               5                   10

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gggcatgtga cgactctttc tcttctgtcg ctgcgg                              36

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Pro Asn Phe Asp Trp Pro Leu Ser Pro Trp Thr
1               5                   10

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tttccgaatt ttgattggcc tctgtctccg tggacg                              36

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Thr Pro Leu Thr Glu Pro Ala Phe Lys Arg His
1               5                   10

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gagacgcctc ttacggagcc ggcttttaag cggcat                              36
```

```
<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tagaacgaag                                                              10

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cttcgttcta                                                              10

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tcagtggatg                                                              10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
catccactga                                                              10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gtattgcgag                                                              10

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctcgcaatac                                                              10
```

```
<210> SEQ ID NO 98
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98 aacgattc                                                                  8

<210> SEQ ID NO 99
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99 gaatcgtt                                                                  8

<210> SEQ ID NO 100
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100 agtggatg                                                                  8

<210> SEQ ID NO 101
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 catccact                                                                  8

<210> SEQ ID NO 102
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102 gtattgcg                                                                  8

<210> SEQ ID NO 103
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103 cgcaatac                                                                  8

<210> SEQ ID NO 104
<211> LENGTH: 8
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104 atgccttc                                                                  8

<210> SEQ ID NO 105
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105 gaaggcat                                                                  8

<210> SEQ ID NO 106
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 tgatggac                                                                  8

<210> SEQ ID NO 107
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107 gtccatca                                                                  8

<210> SEQ ID NO 108
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108 cagtagtg                                                                  8

<210> SEQ ID NO 109
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 cactactg                                                                  8

<210> SEQ ID NO 110
<211> LENGTH: 8
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 110 ttcctgag                                                                    8

<210> SEQ ID NO 111
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111 ctcaggaa                                                                    8

<210> SEQ ID NO 112
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112 gactctct                                                                    8

<210> SEQ ID NO 113
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113 agagagtc                                                                    8

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Gly Gly Gly Ser
1               5
```

METHODS AND COMPOSITIONS FOR ANALYTE DETECTION

RELATED APPLICATIONS

This application claims priority to U.S. provisional application No. 60/775,649, filed Feb. 21, 2006, No. 60/789,345, filed Apr. 5, 2006, and No. 60/866,932 filed Nov. 22, 2006, pursuant 35 U.S.C. 119(e), and the disclosure for each of which is incorporated by reference herein in its entirety.

STATEMENT AS TO GOVERNMENT SUPPORTED RESEARCH

Portions of this invention may have been made with the support of the United States government under contract number 200-2007-19345 granted by the Center for Disease Control. The Government may have certain rights to portions of this invention.

BACKGROUND OF THE INVENTION

This invention relates to assays for analyte(s), e.g., antigens, in a sample such as a biological sample obtained from an animal. In particular, the invention relates to a method and device(s) for the detection of an analyte(s) utilizing binding moieties specifically targeting a selected analyte. More particularly, the analytes to be detected include infectious agents and/or components thereof.

Many types of assays have been used to detect the presence of various substances, often generally called analytes or ligands, in bodily samples. These assays typically involve antigen antibody reactions, ligand, anti-ligand, ligand receptor and utilize, synthetic conjugates comprising radioactive, enzymatic, fluorescent, or visually observable metal soluble tags, and specially designed reactor chambers. Most current tests are designed to make a quantitative determination, but in many circumstances all that is required is qualitative or positive/negative indication. Assays have been utilized to detect infectious agents, such as influenza.

Even the positive/negative assays must be very sensitive because of the often small concentration of the analyte of interest in the test fluid. False positives can also be troublesome, particularly with agglutination and other rapid detection methods such as dipstick and color change tests. Because of these problems, sandwich assays and other sensitive detection methods which use metal sols or other types of colored particles have been developed. These techniques have not solved all of the problems encountered in these rapid detection methods. Moreover, with the emergence of highly pathogenic agents such as influenza virus, there is a need to develop effective laboratory or point-of-care methods and systems that can effectively and accurately detect one or more infectious agents, such as influenza Types or strains within subtypes.

Influenza is commonly seen in local outbreaks or epidemics throughout the world. Epidemics may appear at any time and can occur explosively with little or no warning. The number of people affected can vary from a few hundred to hundreds of thousands. Epidemics may be short-lived, lasting days or weeks but larger epidemics may last for months. Although influenza is a mild disease in most individuals, it is life threatening to elderly, the very young or debilitated individuals. Epidemics are responsible for large losses in productivity. Therefore, there is a need to develop devices and methods to effectively detect what Types and subtypes of a pathogen, such as influenza, present in samples obtained from subjects in order to determine whether the infection is caused by a typical or expected subtype of Influenza (seasonal flu) or a subtype that is the causative agent of an epidemic or pandemic.

It is an object of this invention to provide a rapid, sensitive method for detecting analytes in a biological sample. Another object is to provide an assay which has high sensitivity and fewer false positives than conventional assays. A further object is to provide an apparatus or system for detection of low levels of analytes present in biological samples. Another object is to provide an assay system which involves a minimal number of procedural steps, and yields reliable results even when used by untrained persons. An additional object is to provide a system for testing infectious agents that provides results identifying one or more infectious agents in a matter of minutes. A further object provides a system where results on a testing implement are equally specific and sensitive for the target analytes, notwithstanding that results can be read one to several hours after completion of a reaction necessary to obtain a result. These and other objects and features of the invention will be apparent from the following description, drawing, and claims.

SUMMARY OF THE INVENTION

In certain aspects of the invention a sample collection device (SCD) is provided for use in detection of one or more target antigens or analytes that may be present in a sample. The sample collection device can be utilized in conjunction with a test device. In one aspect, a system is provided for detection of one or more analyte comprising a SCD, a Test Device and a Reader, as further described herein. In one aspect, the invention provides a kit comprising: (a) a lateral flow device comprising a bibulous strip containing (i) a sample application zone, (ii) a detection zone comprising one or more discrete bands of pRNA non-diffusively bound to said strip, each band capable of indirectly specifically capturing a different analyte and (iii) in a control zone; (b) a first conjugate for each of said analytes, each said conjugate comprising a specific binding partner capable of specifically binding to an analyte and a pRNA adapted to recognize one of said discrete bands of pRNA on said strip; and (c) a second conjugate for each of said analytes comprising a specific binding partner capable of specifically binding to said analyte and a label.

In various embodiments, a SCD comprises one or more upper sealed chambers, which can contain the same or different solutions. In one embodiment, the upper sealed chamber comprises at least two compartments or subchambers each comprising. In other embodiments, the upper chamber can comprise puncturable, breakable or rupturable ampoules. In some embodiments, a SCD provides the necessary reagents to form a complex with one or more different target antigens that may be present in a sample, wherein the complex comprises a capture moiety and a detectable label, a Test Device provides the necessary means to addressably capture one or more complexes so formed and a Reader which provides a means to detect one or more signals from addressably captured complexes.

In various embodiments, an upper sealed chamber comprising extraction buffer and/or reagents, a sample collection implement, a sample collection implement holder and a plurality of reagents, wherein the reagents comprise a plurality of specific binding pairs, where each pair comprises a label conjugated to first specific binding agent and a capture moiety conjugated to a second specific binding agent, where the first and second specific binding agents specifically bind a target antigen to form a complex. The capture moiety can be "captured" or immobilized where a partner capture moiety disposed on a substrate binds to the capture moiety-specific binding agent conjugate.

In various embodiments, the plurality of specific binding agents comprise a multitude of groups of specific binding pairs, wherein each group comprises specific binding agents that specifically bind one target antigen, and a second group of specific binding pairs specifically bind a second different antigen. Thus a plurality of specific binding pairs comprised in a SCD is capable of detecting a plurality of different antigens.

In various embodiments, the capture moiety is an oligonucleotide, avidin, streptavidin, pyranosyl RNA (pRNA), aptamer, or a combination thereof. In various embodiments, the label is a metal, a fluorophore, a chromophore or a combination thereof. In some embodiments, the plurality of specific binding pairs comprised in a SCD can contain one type of capture moiety but with different capture moiety partners, e.g., each specific binding agent conjugated to pRNA, where each group that is specific to a different antigen comprises different pRNAs. In other embodiments, the plurality of specific binding pairs comprises one or more different capture moieties, e.g., pRNA for one group of specific binding pairs, while streptavidin for another, or a combination of different types of capture moieties.

In some embodiments, the plurality of specific binding pairs comprised in a SCD can contain one type of label (e.g., specific binding pairs where each group is conjugated to fluorophores having the same or fluorophores having different wavelength signals). In other embodiments, specific binding pairs can comprise a combination of different types of labels (e.g., combination of metals and fluorophores). In one embodiment, the capture moiety is pRNA and the label is Europium.

In various embodiments, the specific binding agents are antibodies, thus a specific binding pair comprises an antibody-label conjugate ("label probe") or antibody-capture moiety ("capture probe"). In such embodiments, a "partner capture moiety" is comprised on a test membrane disposed in a Test Device, which partner binds a specific capture probe, e.g., pRNA partner specifically binding a pRNA (i.e., capture moiety) contained on a capture probe (i.e., antibody specific for a target antigen).

In some embodiments, the different analytes detected are virus or components of virus (e.g., polypeptides). In various embodiments, the different antigens are from influenza virus and subtypes of influenza virus. In one embodiment, the influenza virus that can be detected is influenza virus A and B as well as subtypes of influenza virus. One embodiment is directed to detection of influenza virus strains A and B and subtypes of the formula HxNy, wherein x can be 1-16 and y can be 1-9, or any combination of xy thereof.

In yet other embodiments, the different analytes detected are one or more different infectious agents and/or one or more different subtypes of an infectious agents. Such infectious agents include HIV, HCV, and myobacterium, tuberculosis, bacteria, fungi, yeast, HSV, HPV or a combination thereof.

In various embodiments, an SCD comprises a sampling implement that provides a means to collect a sample from a subject, wherein the sampling implement is comprised connected to the upper chamber via a sampling implement holder. The sampling implement is disposed at the distal end of a shaft, which shaft can be solid, hollow or semi-permeable. In some embodiments, the sampling implement is a swab, a comb, a brush, a spatula, a rod, a foam, a flocculated substrate or a spun substrate.

In various embodiments, an SCD comprises one or more sealed upper chambers wherein the seal functions as a valve to control fluid communication between the upper chamber and lower chamber of an SCD. In some embodiments, the valve can be a break-away valve, a flapper valve, a twist, screw, rupturable, puncturable or breakable valve. In other embodiments, the upper chamber can contain one or more ampoules which prevent solutions contained therein to flow to the lower chamber, unless pressure is exerted to rupture, puncture or break the ampoule so as to release any contents therein.

One aspect of the invention is directed to a SCD comprising a sample reservoir upstream of a plunger implement, a plurality of sealable apertures for delivery of one or more solutions, a substrate for filtering one or more compounds from a sample administered to the sample reservoir and reagents that are capable of specifically binding at least one analyte in said sample.

In another aspect of the invention, a Test Device is provided for detection of one or more analytes, wherein the device comprises a lateral flow membrane in a body, a chamber upstream of the lateral flow membrane containing a fluid or solution, wherein a gap is disposed between said chamber and said lateral flow membrane thus precluding fluid communication between the chamber and the lateral flow membrane. In one embodiment, the pressure excited on the chamber pushes close the gap thus forming fluid communication between the chamber and the lateral flow membrane. In one embodiment, an opening into which a distal end of an SCD fits, is disposed directly above a wicking pad that is disposed downstream of the gap, but upstream of the lateral flow membrane.

In one embodiment, the Test Device chamber comprises one or more subchambers containing the same or different solutions. In other embodiments, the chamber of subchambers comprise one or more ampoules that are breakable, puncurable or rupturable. Thus, where pressure is excited on such ampoules the contents are controllably released. As described herein, a Test Device can comprise a gap means or not comprise a gap means for disrupting fluid communication from the chamber to the lateral flow membrane. A Test Device gap can be from zero to 3.0, 0.5, to 3.5, 1.0 to 2.5, 1.0 to 3.0, or 2.0 to 4.0 mm.

In some embodiments, a Test Device can comprise a body housing the lateral flow membrane, wherein the body provides one or a plurality of windows through which the lateral flow membrane is visible. In various embodiments described herein, a Test Device comprises a lateral flow membrane that comprises a wicking substrate and an absorbent substrate upstream or downstream of the test zones disposed on said lateral flow membrane. In some embodiments, a substrate for collecting a small volume of sample for archiving is provided in a SCD or Test Device. In one embodiment the substrate providing such archiving means is a filter, membrane or paper that collects a small volume of sample and said substrate is subsequently removed from the device.

In various embodiments, an SCD and or Test Device comprises one or more identical identifiable tags, which can be removed from one device and placed on another device.

In some embodiments, the Test Device is shaped to only fit (specialized adaptor shape) into the receiving port of a reader if the upstream chamber has been depressed thus indicating that wash buffer or chase buffer contained therein has been released through the lateral flow membrane. In such embodiments, the Test Device and Reader specialized adaptor provides a means to verify that chase buffer or solution in the upstream chamber of the Test Device has been released and thus washed any sample present upstream of the lateral flow membrane through the lateral flow membrane. Thereby, the specialized adaptor provides a "safety means" to prevent reading of unprocessed samples.

In another aspect of the invention, the processed samples are run through the Test Device's lateral flow membrane, but can be placed aside from 30 minutes to several hours. In various embodiments, a plurality of samples can be run through the Test Device but read at 0.5, 1, 2, 3, 4, 5, 6, 7, 8, 9, 10, 11 or 12 hours later, with consistent and accurate signals.

In certain aspects of the invention, the devices disclosed herein are utilized in methods for detection of one or more analyte that may be present in a sample. In some embodiments, methods are directed to detecting one or more strain of an infectious agent. In one embodiment, a method is directed to utilizing the devices of the invention to detect one or more influenza virus and subtypes thereof. For example, methods are provided for detection of influenza virus A and B, and subtype of influenza A that may be present in a single sample.

In one embodiment, a method is provided for determining whether a subject is infected with a pandemic, non-pandemic or strain of influenza virus for which vaccine is available.

In some embodiments, the Test Device excludes any reagent or binding agent that is capable of specifically binding a target antigen.

In one aspect of the invention, a reader is providing to detect a signal from a Test Device wherein said reader is a UV LED reader. In various embodiments, the signal detected is a fluorescence signal from a detector molecule. In further embodiments, the detector molecule is a lanthanide. In yet a further embodiment, the lanthanide is Europium.

In one embodiment, the reader comprise a UV photodiode. In another embodiment, the reader comprises a UV laser diode.

In another aspect of the invention, a reader is configured to comprise at least one board standard. In another embodiment, a reader is configured to comprise at least two or more hard standards. In various embodiments, a hard standard comprises a label molecule emitting a detectable signal. In further embodiments, the label is a fluorescence label. In yet further embodiments, the fluorescence label is a lanthanide. In yet a further embodiment, the lanthanide is Europium.

In another aspect of the invention, an SCD and Test device of the invention are used in a method to detect one or more analytes, wherein such an analyte is associated with a disease, pathologic or other physiological condition. In various embodiments, such analytes are biomarkers associated with a condition related to the heart, liver, kidney, intestine, brain, fetus, or pancreas. In one embodiment, such analytes are associated with a cardiac condition (e.g., myocardial infarction).

In various embodiments, the devices of the invention can be utilized in any method to detect an antigen or protein (analytes) in a sample obtained from a subject to detect any such analytes, through utilization of a particular panel of immunoreactive or specific binding reagents that are specific for the desired analytes.

In several aspects of the invention, the Test Device comprises an upstream chamber that contains a means for providing a wash running buffer or liquid. In various embodiment, such a buffer or liquid comprises additional agents such as signal/detector molecules that can be read by an optical reader or by unaided visualization. In certain embodiments, the buffer or liquid is comprised in a compartment that comprised of a glass ampoule or membrane pouch, sac or formed filled pouch. In further embodiments, such compartments are raptured, broken or otherwise released of their contents by exerting pressure on said compartments. In other embodiments, such compartments are punctured or lanced by an appendage or needle. In yet further embodiments, such compartments are protected by a safeguard means that precludes accidental or unintentional release of their contents.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 21 illustrates test for influenza B.

FIG. 22 illustrates test for influenza A and subtype H5N1.

FIG. 23 illustrates test for influenza A and subtype H1N1.

Figures 35, 36:
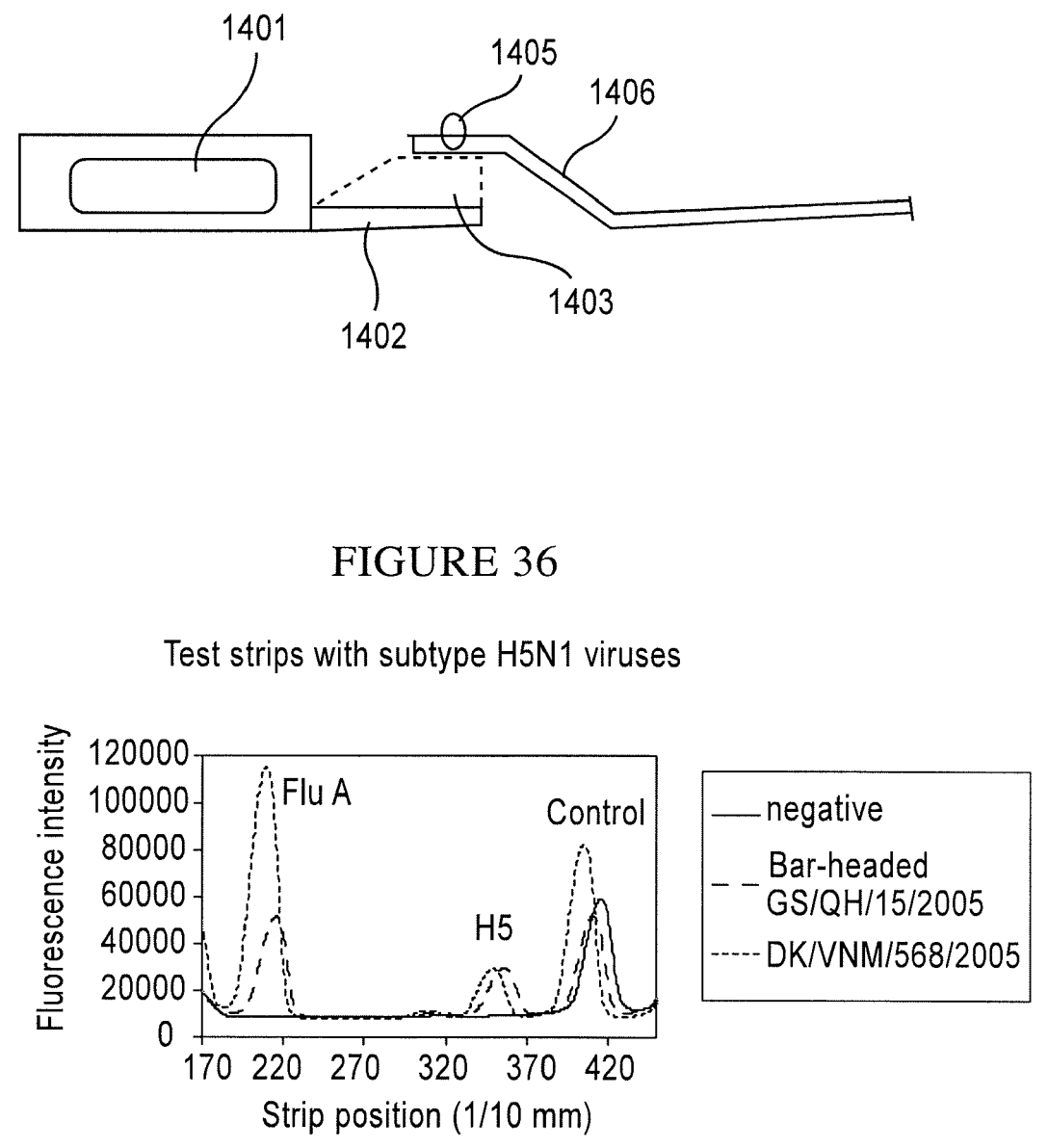

FIG. 35 illustrates an embodiment where an upstream compartment 1401 (e.g., ampoule) containing a liquid is in fluid communication with a dry wicking pad 1402 which swells when said compartment is manipulated to release its liquid content, wherein said swelling increases the size of the wicking pad 1403 so that it becomes in fluid communication with a sample 1405 disposed on a test strip 1406. Therefore, based on the density/type of wicking material 1402 a predetermined time delay can be built into the system from the point of release to point of initiating flow of the sample 1405 through the test strip 1406.

FIG. 36 illustrates fluorescence intensity of subtype H5N1 viruses.

FIG. 38 depicts a graph of fluorescence intensity of Flu B viruses.

FIG. 39 illustrates the sensitivity using a MAB system.

FIG. 40 illustrates the sensitivity using a pRNA system.

FIG. 41 illustrates the sensitivity using a pRNA system and membrane blocking.

FIG. 42 provides a comparison of sensitivity for MAB, pRNA and pRNA with blocking.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Various aspects of the present invention are directed to devices and binding-pair assays that utilize specific binding moieties and capture moieties for the qualitative and/or quantitative analysis of selected analytes in samples. The invention is useful in a variety of assays that are utilized to detect one or more infectious agents present in a sample. Assays useful in the invention include, but are not limited to, competitive immunoassays, non-competitive immunoassays, sandwich immunoassays and blocking assays.

However, the use of the invention is not limited to immunoassays, as other assays including ligand-receptor, ligand-binding protein, aptamer-binding agent, enzyme-substrate, chemical or biochemical reactions are detected by utilizing a device or method of the invention. In one aspect of the invention, methods and systems of the invention utilize a sample collection device, a test device and a reader. Various specific assay protocols, reagents, devices or analytes useful in the practice of the invention are known, see, e.g., U.S. Pat. Nos. 4,313,734; 4,366,241; 5,266,266; 6,235,539; 6,468,474; 6,565,808; 6,448,001; or 5,415,994, as well as U.S. Pub. Nos. 2006/0040405; 2004/0014094; 2004/0048395; or 2005/0130120.

In one aspect of the invention, a sample collection device is utilized to collect a sample and process a sample with immunoreactive reagents that provide a detection means and a capture means, which processed sample is subsequently provided to a test device, which provides a means for reading/viewing signals provided by said detection means. The signals can be read by the naked eye or with an instrument depending on the combination of detection means (e.g., conjugate labels) utilized. Furthermore, the test device can be configured to allow detection of multiple analytes. Such analytes can be from one or more infectious agents, including different strains and/or subtypes. Detection can include qualitative and/or quantitative measurements of one or more analytes.

Figure 2A:
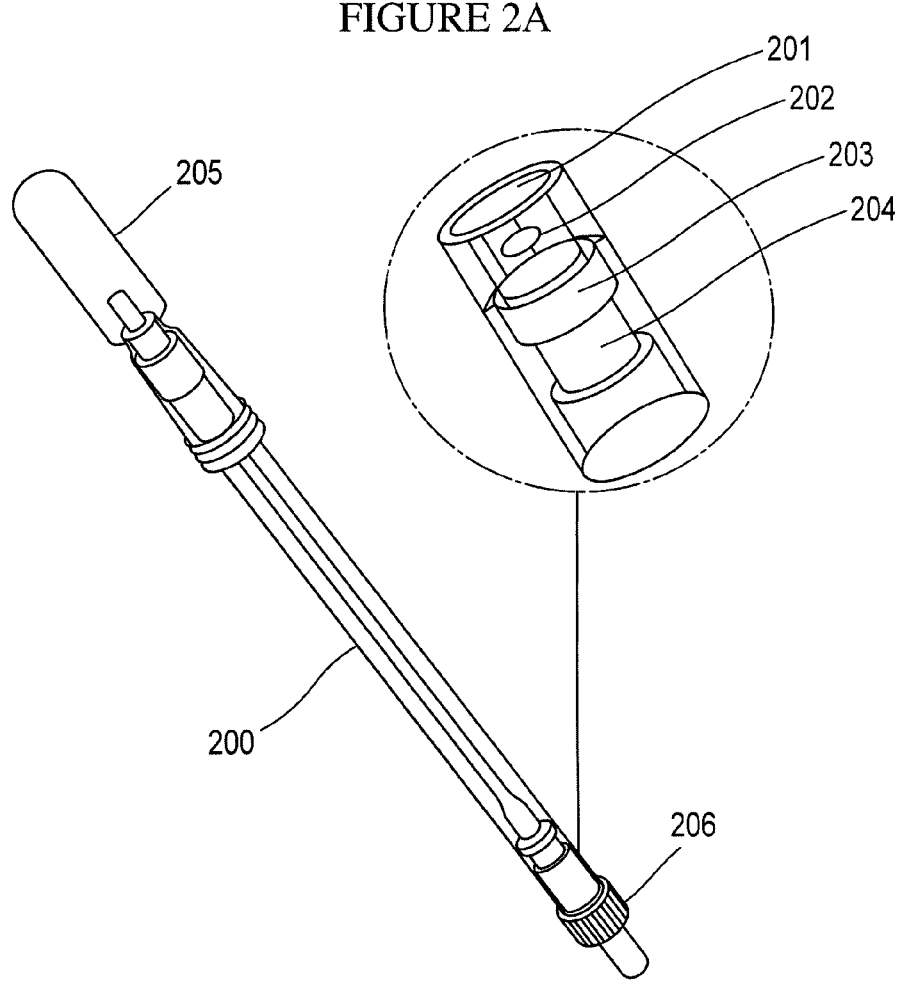
FIG. 2A illustrates a sample collection device with a blow up view of a mixing compartment.
Figure 2B:
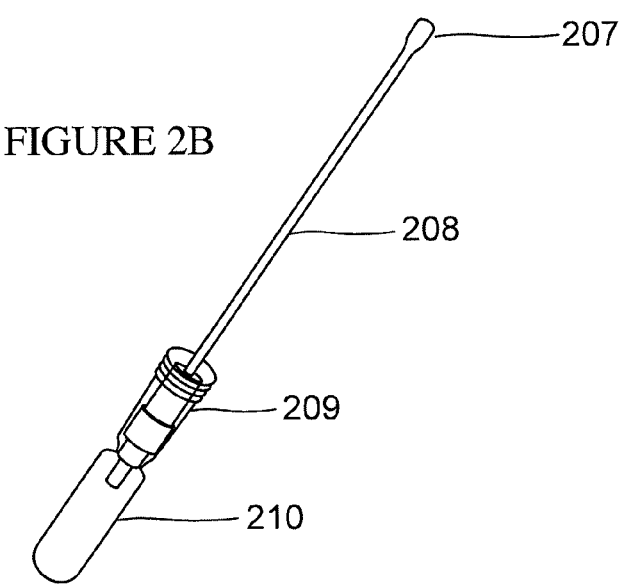
FIG. 2B illustrates a sampling assembly.

Sample Collection Device. One aspect of the invention is directed to a sample collection device ("SCD") that comprises the necessary means to collect a biological sample, as well as the reagents and buffers necessary to process the sample and react to the binding reagents with one or more target analytes. As shown in FIG. 2B, an exemplary SCD comprises an upper chamber 210 to which is attached a sampling implement holder 209 a stem 208 a sampling implement 207, collectively forming a sampling assembly.

Figure 1:
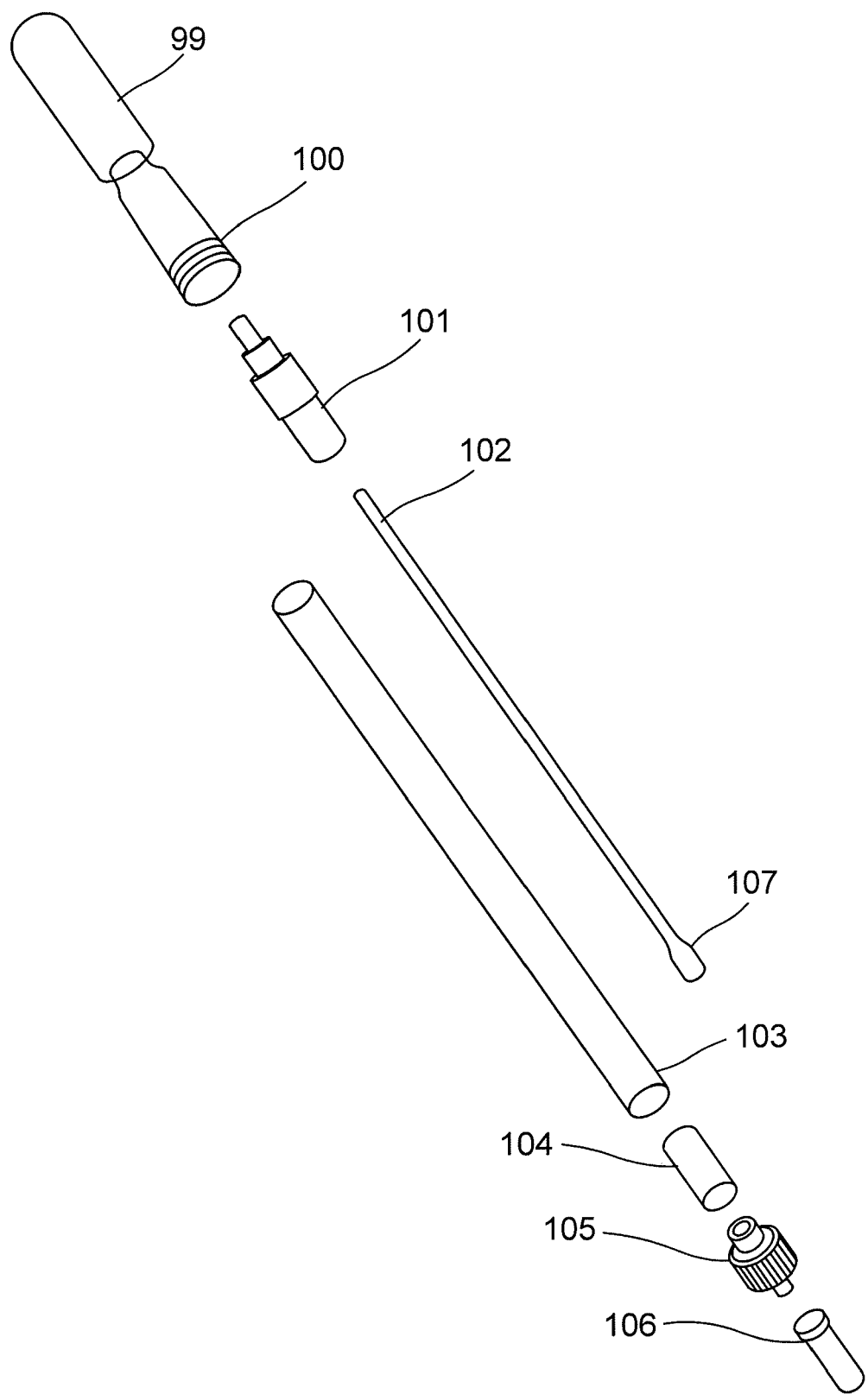
FIG. 1 illustrates a sample collection device.

The sampling assembly FIG. 1 is removable from a housing comprising a sample receiving tube 103, a lower chamber mixing or reagent area 104, which can contain reagents that specifically bind to one or more target antigens. The lower chamber 104 can comprise one or more compartments. For example, two compartments can be arranged in series in the lower chamber. The sampling assembly is placed into the sample receiving tube 103 portion of the housing to provide an integrated configuration. In such a configuration a sampling implement 107 is upstream of and in fluid communication with the lower chamber. The length the sampling assembly can be optimized for sample collection, e.g., throat and nasal sample collection. For example, the length of the device (e.g., integrated configuration) can be about 1 to 9 inches, or about 3, 4, 5, 6, 7, 8 or 9 inches.

The stem 102 can be hollow, solid or semi-porous. Therefore, in some embodiments, the stem actually provides a path of fluid communication from the upper chamber 100 to the sampling implement 107 (e.g., swab). The stem is held by the sample holder 101 which fits into a receiving end of the upper chamber 100. For example, the stem may be hollow or semi-permeable and a portion of the stem which may extend into the upper chamber has a terminal end that is closed, so that if the stem portion in the upper chamber is snapped or broken, then fluid communication (i.e., fluid flow) is provided between the upper chamber down through the distal end of the stem to a sampling implement (e.g., swab) comprising a sample (e.g., biological sample).

An upper chamber can comprise one or more compartments. The upper chamber can be comprised of a semi-rigid or depressible material, and shaped as a bulb 99. Such a bulb can comprise a solution.

The upper chamber can be sealed. Furthermore such a seal can be punctured, broken or opened via a valve structure, so as to provide fluid communication between the upper chamber and lower chamber. In some embodiments, the solution in the upper sealed chamber is a buffer solution. In various embodiments, the volume for a solution in the upper chamber is from about 10-500 µl, or from about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. In one embodiment, the solution volume is up to 150 µl.

In some embodiments, a liquid solution comprising the necessary reagents (e.g., detection/capture specific binding agents, etc.) can be disposed in the reagent area of the lower chamber in liquid communication with the upper chamber. As exemplified in FIG. 2A, fluid from the upper chamber flows down to the sampling implement to extract sample and—the extracted sample passes through an aperture that may restrict/control the liquid flow from the upper chamber to the lower chamber comprising, for example, an aperture to control flow by size, e.g. size of perforations or type of substrate or filter that is disposed on the proximal end 201 of a compartment in the lower chamber. The lower chamber may contain a reagent area. In one embodiment, the reagent area (e.g., 203) contains a solid substrate that includes the necessary reagents 202 (e.g., immunoassay reagents, such as detection and capture probes, etch), formed as a dried solid, separately disposed or in a unified solid.

Therefore, where a sample is washed downward via the solutions (e.g., buffer) in the upper chamber, a mixture is produced carrying the sample that travels down to the lower chamber reagent area, which chamber comprises the solid reagent-containing substrate 202. The solid reagent is dissolved rapidly by the buffer and the resultant solution is a mixture of sample that may contain analyte(s) of interest, and the immunoassay reagents (e.g., specific binding agents, label conjugate and capture probes, etc.). For example, a solid reagent 202 can include both label and capture probes used in the assay that are capable of specifically binding a target analyte. The integrated device 200 includes the upper and lower chambers, the sample collection device and the luer lock 206 which locks into the lateral flow device for delivery of the reaction mixture for subsequent detection. Furthermore, as noted the upper chamber can be designed with a depressible (e.g., plastic) bulb 205 so that if desired additional pressure is applied to force fluid flow from an upper chamber into a lower chamber.

In one embodiment, the upper chamber comprises a valve that allows controllable release of a solution comprised in the upper chamber. For example, where the valve is a snap-valve, the user applies force to the valve stem to break the stem, whereby the breakaway feature allows buffer to enter the lower chamber via the stem. Furthermore, the sealed chamber can be a squeezable bulb, which is capable of being compressed (e.g., user applies pressure to the bulb), thus controlling the flow rate of the solution (e.g., buffer) to the sampling implement.

In some embodiments, the upper chamber is comprised of a bulb component that is a self-contained compartment that includes a solution. Such solutions include extraction, lysis, reagent, buffer or preservative solutions. In one embodiment, the solution is a buffer solution that is utilized to transfer the biological sample from the sampling implement down to the lower chamber.

Figure 5:
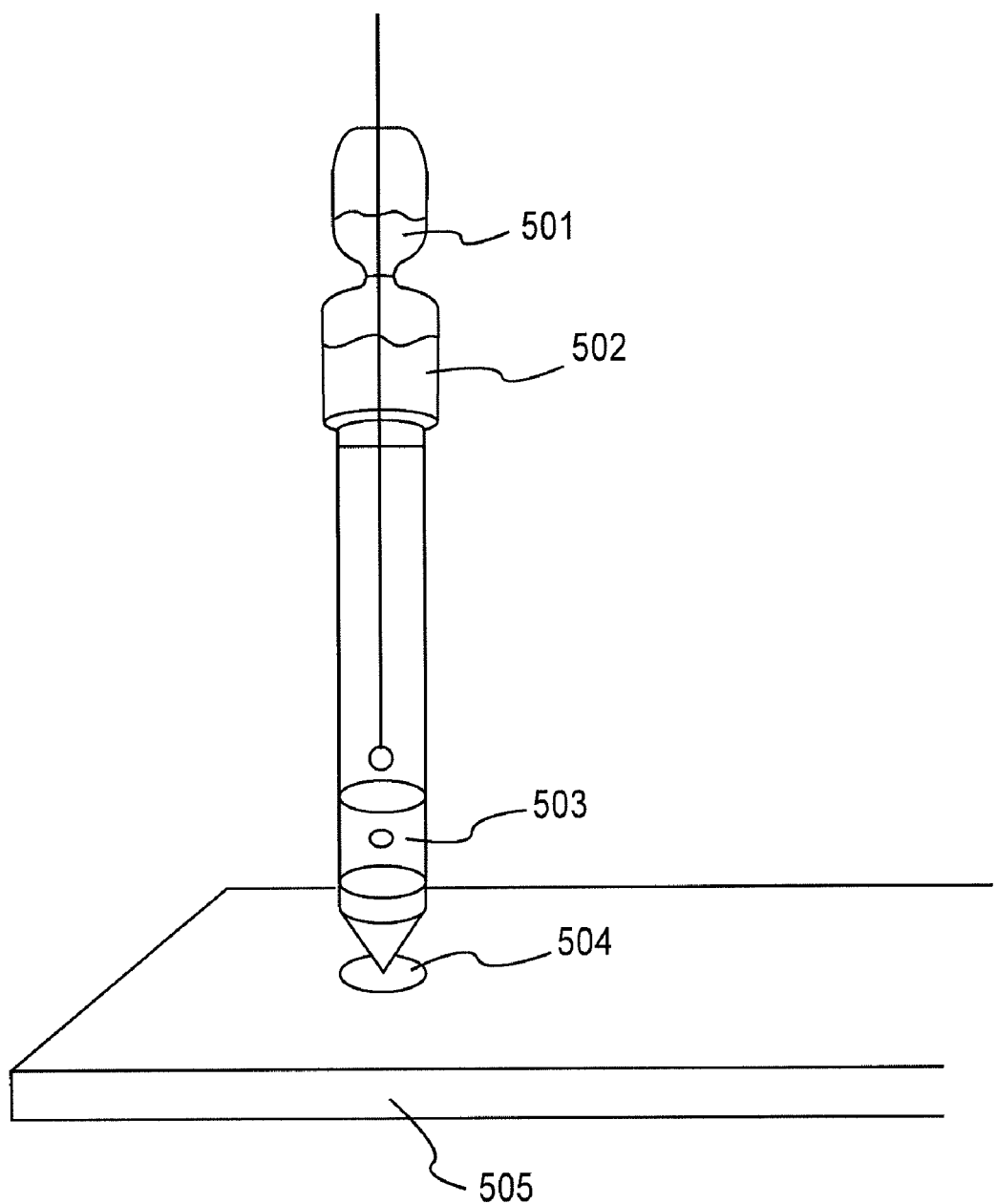
FIG. 5 illustrates a sample collection device.

Furthermore, such an upper chamber can comprise one or more compartments, such as depicted in FIG. 5. Each compartment can comprise a solution that is the same or different 501 and 502.

Furthermore, such solutions can comprise reagents as desired including but not limited to extraction buffers, reducing agents, immunoreactive agents, such as, anti-analyte specific binding agents comprising detection labels (e.g., conjugates) and capture moieties. The reagents for reactions are depicted in 503 and 504 shows attachment of the luer to the test strip 505.

Figure 6:
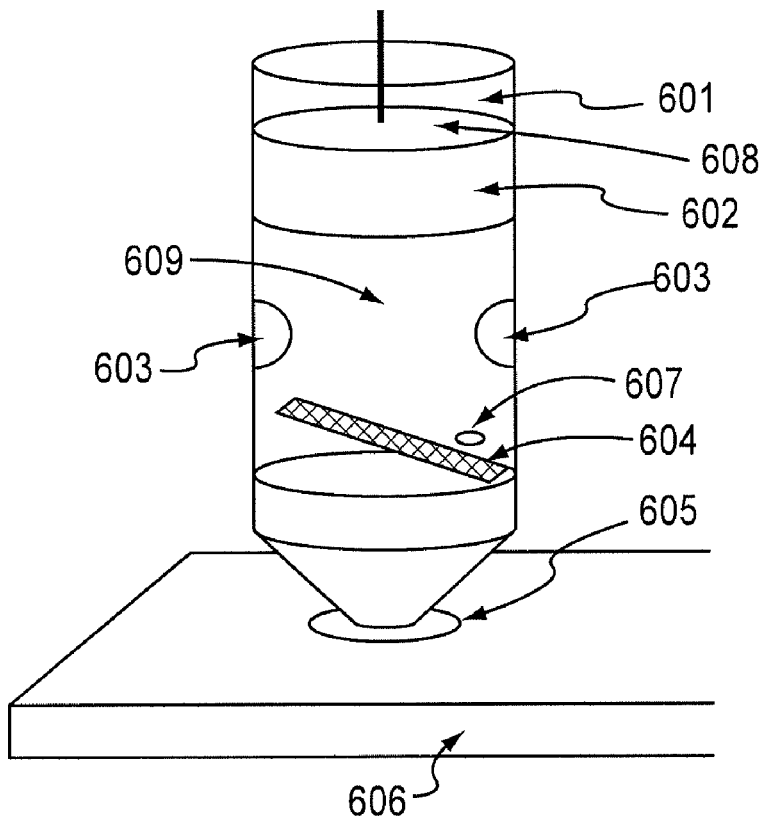
FIG. 6 illustrates a sample collection device.

In another embodiment, the sampling assembly is not integrated with the housing containing a sample receiving tube. See FIG. 6. In such a configuration, the sampling assembly 601 is utilized to collect and deliver a sample to a sample receiving chamber 609. The sample receiving chamber can be open or closed to allow a sample to be introduced into sample receiving tube. It should be understood that any sample receiving tube disclosed herein can be of a variety of geometric shapes, including cylinder, square, triangular or any polygonal, as desired. In some embodiments, the housing can comprise one or more sealable apertures 603 that can be opened to add one or more selected reagents 607, buffers or wash fluids.

For example, in one embodiment, whole blood is drawn into the sample receiving chamber 609. Subsequently, the sample passes through a membrane 602 (e.g., a membrane to separate red blood cells from plasma, allowing the plasma to pass through) into a lower portion of the sample receiving tube to mix with various reagents, for example, necessary for an immunoassay. Immunoreagents—necessary to target specific analytes can be pre-selected and disposed as a solid substrate 607 in the SCD or added through an aperture 603, or can be disposed on a membrane 604.

As the whole blood sample is discharged, the membrane 604 may act as a filter to precludes passage of blood components, thus allowing only plasma to pass through the distal end of the sample receiving tube 605, which will fit into the Test Device 606. Additional valves that can be utilized include a rotary, breakable, stopcock, gate, ball, flapper, needle, butterfly, pinch, bellows, piston, slide, plug, diverter, or actuator valve.

As used herein, a "capture probe" refers to a conjugate of a binding agent linked to a capture moiety and a "detection probe" refers to a conjugate of a binding agent linked to a label or signal producing moiety, wherein each is capable of specifically binding to a target analyte. Furthermore, for clarity, a "capture moiety partner" in the context of the Test Device (described below) refers to a complement, cognate or partner molecule that specifically binds to a capture moiety comprised on a capture probe.

Solid reagent components include, a powder, pill, bead, lyophilized pellet, pressed lyophilized power, dried on solid support (e.g., glass/plastic bead), lyophilized on or in association with a solid support or dried directly in the mixing or lower chamber. Such reagents are known in the art such as disclosed in CURRENT PROTOCOLS IN IMMUNOLOGY (Coligan, John E. et. al., eds. 1999).

In some embodiments, as the solution passes through the sampling implement, an extraction step of a sample occurs (e.g., where solution includes an extraction buffer). Furthermore, the lower chamber can comprise a filter through which an extracted sample flows. For example, if a filter is disposed at the proximal end of the lower chamber, an extracted sample then flows through a filter (e.g., a mesh disk) thereby precluding certain components of the extraction mixture from passing into the reagent area compartment comprising a solid reagent bead. Furthermore, a filter means can also function to restrain the reagent bead during SCD transportation and storage. As noted herein, the reagent bead can comprise both the detection and capture probe, or two separate beads can each contain detection or capture probes.

The filtering aspect allows an analyte of interest to migrate through the device in a controlled fashion with few, if any, interfering substances. The filtering aspect, if present, often provides for a test having a higher probability of success, depending on the type of sample being processed, as would be evident to one of skill in the art (e.g., whole blood sample versus throat swab). In another embodiment, the SCD may also incorporate reagents useful to avoid cross-reactivity with non-target analytes that may exist in a sample and or to condition the sample; depending on the particular embodiment, these reagents may include, but not limited to, non-hCG blockers, anti-RBC reagents, Tris-based buffers, EDTA, among others. When the use of whole blood is contemplated, anti-RBC reagents are frequently utilized. In yet another embodiment, the SCD may incorporate other reagents such as ancillary specific binding members, fluid sample pretreatment reagents, and signal producing reagents (e.g., substrates necessary for reacting with label conjugates).

In another embodiment, the lower chamber can comprise a small element of absorbent paper, on which a predetermined percentage of the extracted sample is retained for archival purposes. After passing through the collection device and having a portion restrained for archival purposes, the extracted sample contacts a reagent solution or solid (e.g., conjugate bead 202), and the next assay step takes place as the specimen liquid rapidly dissolves the conjugate bead and allows the reactants to mix and start the assay.

In other embodiments, the luer 105 disposed on the distal end of the SCD can be replaced with or further attached to a valve structure that also functions to control the flow of liquid out from the sample collection device. A valve can also be utilized in practice of the invention, where the valve is disposed in the upper sealed chamber, thus providing a means to control release of solutions contained therein. Whether in the upper chamber, lower chamber, or between any compartments disposed in the SCD, a valve can be of any type as recognized in the art such as, but not limited to, a rotary, snap, breakable, stopcock, gate, ball, needle, butterfly, pinch, bellows, piston, slide, plug, diverter, or actuator valve. In one embodiment, the valve is a snap valve which is rendered open where pressure is exerted in the stem portion of the valve that extends into the upper sealed chamber (100), thereby breaking open the hollow stem 102 and allowing the contents of the sealed upper chamber to flow into the hollow tube, at the end of which is disposed a sampling implement (e.g., swab 107).

In one embodiment, there is a valve at the distal end of the SCD. When the valve is in the closed position, a sample or sample and reagent can be retained in the lower chamber 104. When the valve is in the open position the contents of a mixing subchamber—can be released, for example by gravity flow. Alternatively, the bulb component of the sample collection device is utilized to release the sample/reagent from the luer, luer-valve or valve. In a preferred embodiment of the present invention, the content from the distal or outlet end of the sample collection device ("SCD") is released from the SCD such that the flow can be actuated, regulated or modulated.

In another embodiment, the distal end of the SCD is open, whereby prior to release of a solution from the upper sealed chamber, the SCD is engaged (e.g., by friction fit) into the receiving port of a Test Device. In such an embodiment, the fluid flow from the distal end of the SCD into the Test Device is not regulated by a luer or a valve structure.

In another embodiment, the distal end of the SCD does not utilize a valve but rather is open, The SCD may be attached to the test device prior to release of the buffer from the upper chamber. Upon release of the solution from the upper chamber, the sample is released and/or extracted from the collection implement by the solution and mixed with the reagents located in the lower chamber. The mixture then flows to the test device for analysis of the presence of one or more analytes. It is possible to include water-dissolvable membranes within the lower chamber to slow the flow of the mixture out of the SCD) onto the test device. Such membranes are conventional and can be designed to permit the retention of the mixture for differing periods of time sufficient to allow mixing and reaction of the reagents and sample analytes. For example, such membranes can be prepared from proteins, polysaccharides or film formers.

In another embodiment, the distal end of an SCD comprises a very narrow opening that prevents fluid flow unless and until pressure is applied to the device (e.g., via the bulb structure of the SCD, or if the housing is depressible, then by exerting pressure on the housing itself) to force the fluid out from the distal end. In other words, there is no valve of any sort disposed at the distal end of the SCD.

In another aspect of the present invention the fluid regulatory means (e.g., luer 105, luer-valve combination and valve) is closed such that the sample or sample and one or more reagents can be retained in the lower chamber 104 for any length of time. The valve structure can then be mechanically, fully or partially, opened to release the contents through the distal or outlet end of the SCD into a test device, optionally at a regulated or modulated rate.

Reagents utilized in an SCD of the invention can include one or more salts, chelators, anticoagulants, detergents, stabilizers, diluents, buffering agents, enzymes, cofactors, specific binding members, labels, mucolytic and the like. The one or more reagents can be compounds that facilitate analysis of a sample. Furthermore, such reagents can readily be adapted for use in a Test Device of the invention.

In a one embodiment the SCD is engaged to a second device, for example the test device of the present invention, such that opening of the valve structure or removing a cap 106 covering the opening (no valve) releases the contents into the second device. In another embodiment, engaging the SCD comprising a male luer to the test device comprising a female luer results in release of the contents of the reaction subchamber. In a further embodiment, the contents from the distal end can be released via the bulb component. Where a valve structure is utilized in the SCD, the valve structure can be opened to release the contents by various means such as, but not limited to, opening a stopcock or by turning, rotating, twisting or sliding the valve structure such that the valve can be opened to allow fluid communication into the test platform or by removing a cap which opens the fluid flow path.

Archive Sample. In one aspect of the invention a means for archiving a portion of a sample is provided. In some embodiments, an SCD or Test Device, or both, comprise an archival means, which can comprise an absorbent or adsorbent substrate (e.g., paper or membrane),—a short capillary tube of defined length, or a small reservoir/compartment for retaining a portion of the sample in the lower chamber. In some embodiments, this archival mechanism is located at a position in the device before the sample encounters the reaction reagents.

In one embodiment shown in FIG. 28, a small compartment, that can provide a small reservoir for an archive sample, 1109 is positioned in the test device adjacent to the port/aperture 1108 for delivery of sample to the test device. Such an archive compartment can be configured to be removable or so that a substrate onto which the archive sample is disposed, is itself removable from said compartment. For example, a filter/membrane material sized to fit into the compartment will function to collect to a predetermined capacity of sample (e.g., cell, cell components, protein, nucleic acid, etc.). The test device may contain a pouch 1106 of wash buffer with a housing or cover 1107

Figure 29A:
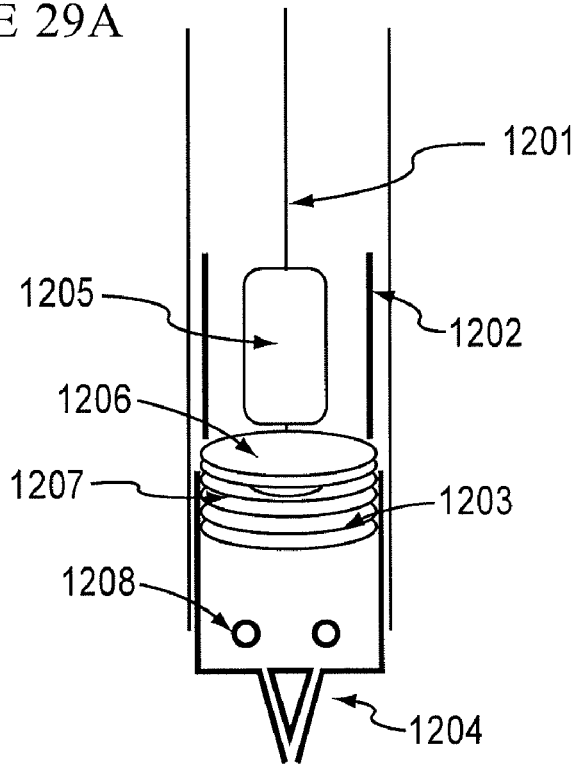
FIG. 29 provides one illustration of an sampling device with an archival component; the sampling swab 1205 is attached to a hollow shaft 1201 and is flanked by sleeves 1202 upstream of a hydrophobic frit (10+u) 1206 and 1203 followed by a (FIG. 29B) filter paper that can be in various shapes with regions for retaining an archive sample 1209 and three dimensional regions 1210 that can for example retain a reagent pill/bead. In addition, reagent pill/beads can also be disposed in the compartment downstream of the filter paper 1208 which can allow mixing before expelling the sample through the tip 1204.

In another embodiment, an SCD comprises a means for retaining an archive sample FIG. 29A. For example, within a SCD lower compartment, filter paper and hydrophobic membranes can be provided configured to retain a sample for archiving purposes. Various combinations of materials are possible. In one embodiment the means for archiving comprises three disks 1203, 1206, 1207, that may or may not touch each other. In another embodiment, the SCD FIG. 29A can be configured with sleeves 1202 which provide a means to move the sizes of the tube/casing closer to the swab 1205 attached to stem 1201 so that as a fluid exits the swab it will stay in close proximity to the swab, so as to improve the efficiency of extracting fluid from the swab. A reagent bead is depicted as 1208 and the exit port is 1204.

Figure 29B:
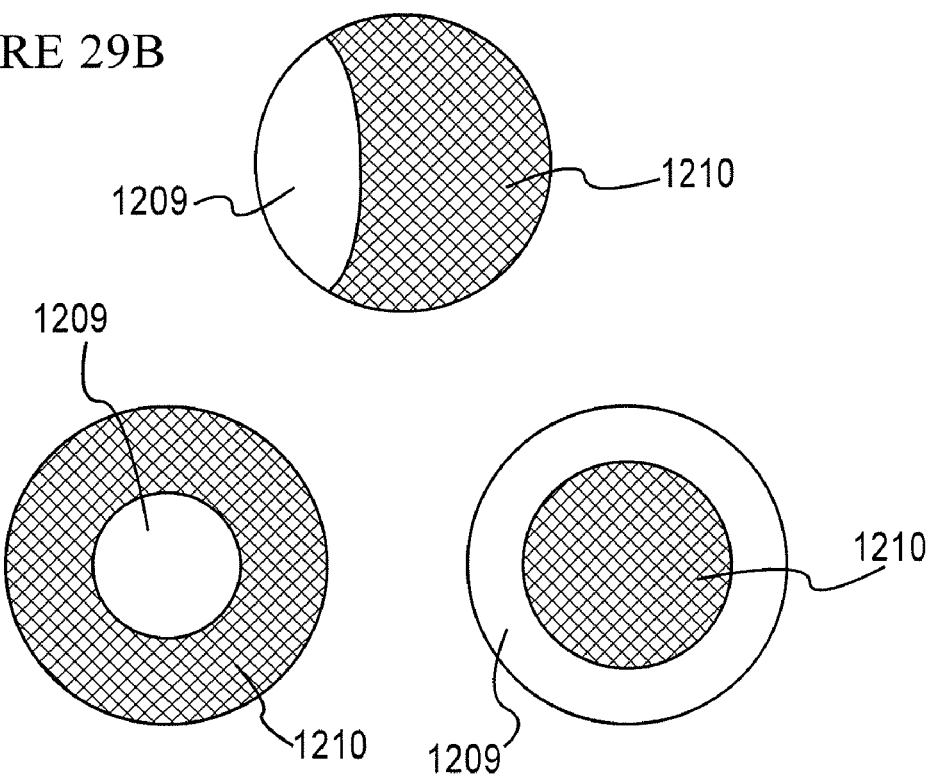

As shown in FIG. 29B the disks can comprise a grid portion 1210 and a pad portion 1209, wherein the pad portion is designed to retain an archive sample. The pad portion can be comprised of any absorptive/adsorptive material and can comprise 5, 10, 15, 20, 25, 30, 35, 40, 45 or 50% of the surface area of a disk. Furthermore, the grid portion can comprise three dimensional ("3D") substrates raised relative to the surface of a disk. Such 3D protrusions can provide a grid into which a reagent bead can be disposed. Such beads can measure in size from about 0.5, 1, 1.5, 2.0, 2.5, 3.0, 3.5, 4, 4.5, 5.0, 5.5, to about 6.0 mm.

In one embodiment, the archived material is a cell(s) or cellular component, including but not limited to a protein, peptide, protein fragment or nucleic acid molecule. Therefore, samples can be preserved for further testing depending on the type of molecule archived (e.g., protein versus nucleic acid). Furthermore, archive disks 1207 (for example as shown in FIG. 29A) provide a means of storing samples and maintain stability of said samples from about 1, 2, 3, 4, 5, 6, 7, 8, 9, 10, 11, 12, 13, 14, 21 to 30 days. For example, RNA is stable for about 2, 3, 4, or 5 days.

In another embodiment, the archival disks are placed in a preservative solution, which extends storage time for said archive samples from about 1, 2, 3, 4, 5, 6, 7, 8, 9 or 10 weeks. Of course depending on the in-field setting, samples can be stored indefinitely (e.g., once the sample is subjected to freezing).

In another embodiment, a reaction compartment—in the lower chamber can be removed from the sample receiving tube and placed in a housing (e.g., plastic tube). In one embodiment, the compartment (e.g., a cage) retains a small volume of sample mixture to which a preservative can be added for storage. In another embodiment, the solutions provided in the upper chamber or a reaction solution in the lower chamber can also include preservatives necessary to archive a liquid sample. Such preservatives are known in the art. See, e.g., U.S. Pat. No. R.E29061; Buccholz et al. Transfusion. 1999 September; 39(9):998-1004; Quiagen specialty reagents, available at Quiagen.com.

In one embodiment, an archive sample is retained for later testing (e.g., by RT-PCR, See Example 8).

Sample Identification. The SOD also includes anywhere on the sampling implement or the sample receiving tube, for example, attached to the outer tube 103, 3 identical identifying labels (e.g., barcodes allowing at least $10^9$ unique values) for patient identification number. The labels can be peel-off and is self-adhesive. One label is retained on the SCD 103. The peel-off copies can be placed on the Test Device FIG. 3 and on any facility paperwork, or an archival reservoir means. Bar code format will be to a universal standard such as Codabar 303 or 305. In other embodiments, the identifying labels can be signal emitting transponders known in the art, including but not limited to, radio frequency emitter, light emitter or electromagnetic wave emitter.

Compartments in the Upper or Lower Chambers. In some aspects of the invention, the SCD comprises one or more compartments in the lower chamber that can include reagents, filters, membranes and reservoirs. In one embodiment the upper chamber of the SCD nay comprise one, two or more compartments, each of which can further contain a solution. In some embodiments, such compartments can comprise the same or two different solutions, reagents, buffers, or a combination thereof. Further, multiple compartments can be arranged in series in a lower chamber (e.g., multiple cages— in series). In addition, such compartments may be referred to as "subcompartment" or "subcompartments" in the disclosures herein.

In one embodiment, compartment is distal relative to a sampling implement and comprises a liquid or solid reagent component that comprises binding agents that are specific to a particular analyte (or analyte type). For example, the liquid or solid reagent component includes a specific binding agent (e.g., antibody) that is capable of specifically binding an analyte that may be present in a sample. In some embodiments, a single reaction or mixing compartment—is utilized in the SCD that is distal to and in fluid communication with the sampling implement. In other embodiments, one or more compartments can be utilized where one compartment functions as a lysis or extraction chamber, while a second compartment distal to the first compartment functions as a reagent-sample mixing chamber. In further embodiments, —filtering means may be disposed on the proximal end of one or more compartments, which compartment(s) is disposed— distal relative to the sampling implements. Filter means can be utilized to remove certain components from the sample, prior to extraction/lysis, sample-reagent mixing, during processing or before release from the SCD. Furthermore, the same or different filtering means can be disposed on multiple compartments if such multiple compartments are present in the sample receiving tube.

Samples.

A sample is any material to be tested for the presence and/or concentration of an analyte. In general, a biological sample can be any sample taken from a subject, e.g., non-human animal or human and utilized in the test devices. For example, a biological sample can be a sample of any body fluid, cells, or tissue samples from a biopsy. Body fluid samples can include without any limitation blood, urine, sputum, semen, feces, saliva, bile, cerebral fluid, nasal swab, urogenital swab, nasal aspirate, spinal fluid, etc. Biological samples can also include any sample derived from a sample taken directly from a subject, e.g., human. For example, a biological sample can be the plasma fraction of a blood sample, serum, protein or nucleic acid extraction of the collected cells or tissues or from a specimen that has been treated in a way to improve the detectability of the specimen, for example, a lysis buffer containing a mucolytic agent that breaks down the mucens in a nasal specimen significantly reducing the viscosity of the specimen and a detergent to lyse the virus thereby releasing antigens and making them available for detection by the assay. A sample can be from any subject animal, including but not limited to, human, bird, porcine, equine, bovine, murine, cat, dog or sheep.

For example, a sample can be derived from any source, such as a physiological fluid, including blood, serum, plasma, saliva or oral fluid, sputum, ocular lens fluid, nasal fluid, nasopharyngeal or nasal pharyngeal swab or aspirate, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings and meat extracts are also considered biological fluids. Pretreatment may involve preparing plasma, from blood, diluting or treating viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

Other fields of interest include the diagnosis of veterinary diseases, analysis of meat, poultry, fish for bacterial contamination, inspection of food plants, restaurants, hospitals and other public facilities, analysis of environmental samples including water for beach, ocean, lakes or swimming pool contamination. Analytes detected by these tests include viral and bacterial antigens as well as chemicals including, for example, lead, pesticides, hormones, drugs and their metabolites, hydrocarbons and all kinds of organic or inorganic compounds.

Test Device.

The present disclosure provides a test device, particularly immunoassay devices, for determining the presence or absence of multiple analytes in a fluid sample. In general, a Test Device FIG. 3 of the present disclosure includes a matrix defining an axial flow path. Typically, the matrix further includes a sample receiving zone, one or more test zones and one or more control zones. In frequent embodiments, a test region comprises the test and control zones, which are collectively addressable lines.

As used herein in the context of the Test Device the terms "axial flow membrane", "lateral flow membrane", "test membrane", "test strip" or "matrix" are used interchangeably which employs capillary action to move or transport the test fluids or employs the movement of fluid separate from capillary action as where fluid is pumped by the accumulation of gas pressure, hydraulic pressure (direct pumping using a piston or rotary, bellows or other type pump on the assay fluids, electrostatic movement due to an electric field, gravity, etc.).

Figure 3:
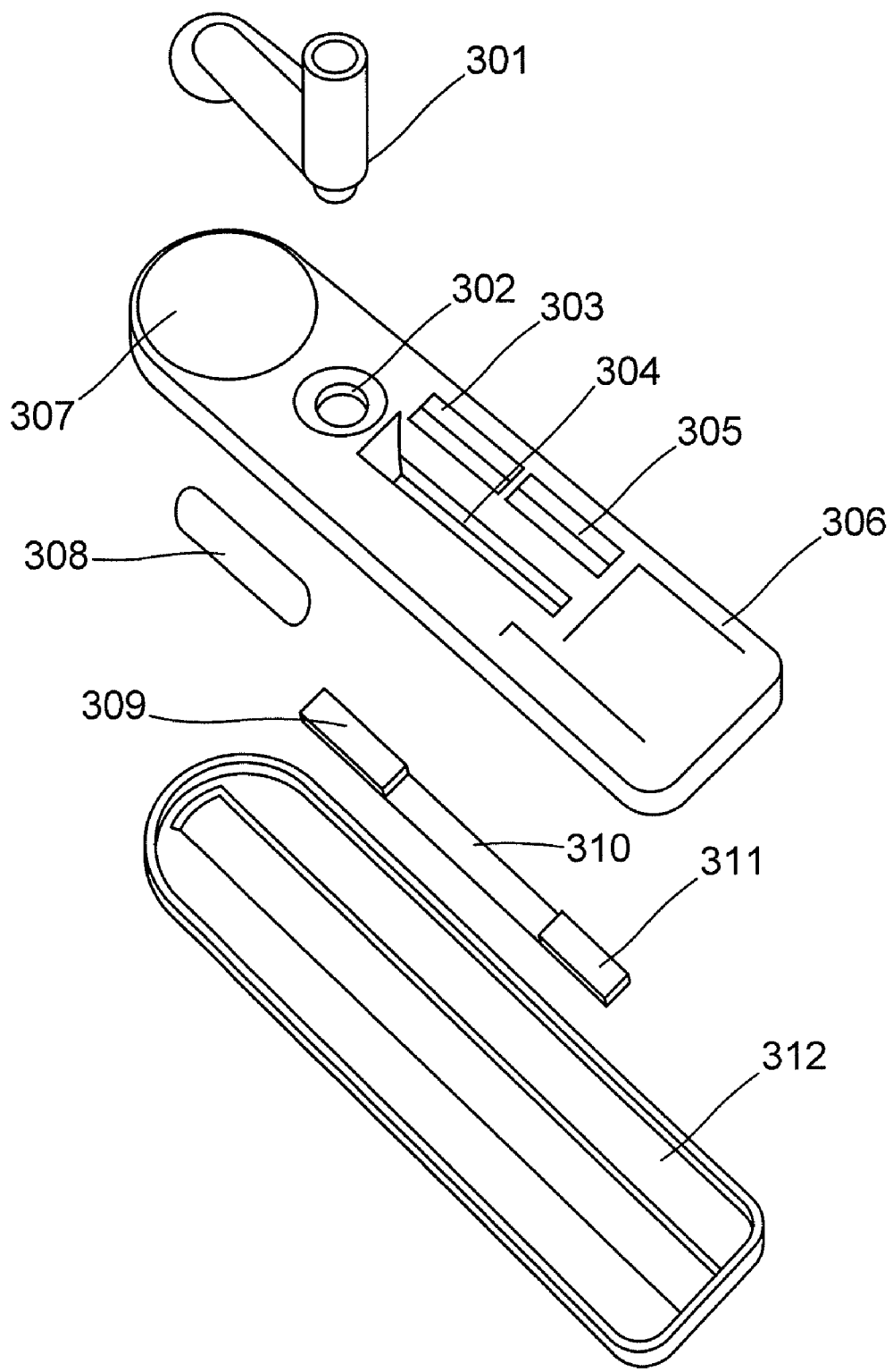
FIG. 3 illustrates a test device.

In one aspect of the invention, the Test Device as depicted in FIG. 3 is comprised of an aperture/port into which the distal end of a SCD of the invention is engaged either by friction fit, luer lock, adaptor or valve. An aperture/port 302, —provides an opening through which a sample from the SCD flows into the Test Device. A blood separation membrane can be disposed at the port which provides one way flow. In another embodiment, such a membrane can also be disposed in the SCD (e.g., immediately distal to the sample swab implement).

Upstream of the aperture is a compartment 307 that may be in fluid communication with the aperture, which aperture is in fluid communication with a wicking substrate 309. Furthermore, the compartment can comprise one or more subcompartments 308 that contain one or more solution(s). Subcompartments in the context of the Test Device can be made of a pierceable, puncturable, breakable (e.g., ampule) or depressible bladder like material. In one embodiment, the collar breaks away, however, the buffer is only released once additional force is applied to the buffer/wash compartment 308. As indicated herein, such compartments can be manipulated by applying pressure so as to puncture, break or depress the compartment enough so to release it contents. In addition, such compartments may be pierced by a lance, stab or appendage that breaks into said compartment upon exertion of force (e.g., thumb pressing down) onto said compartment.

In one embodiment, the Test Device comprises two sections, wherein one section comprises a portion where a sample is applied 302—and a compartment upstream of portion where the sample is applied comprising a wash or running buffer 308. In another embodiment, the upstream section can comprise one or more (e.g., two) compartments which may contain the same or different buffers, wherein each compartment can be separately or simultaneously manipulated to expel its contents.

In another embodiment, the compartment 307 itself can be semi-rigid, pliable or depressible, or bladder like, which provides a means for compacting the compartment to expel any contents therein. Therefore, in some embodiments, a user can exert pressure on the compartment 307 that will result in contents therein, whether self-contained or contained in a subcompartment, to be released to the wicking substrate 309. Such a solution can function as a wash or chase buffer, mobilizing or enhancing mobilization of the processed sample mixture through the wicking pad and into the test strip 310. Generally, such liquid solutions can comprise wash buffer, saline or any desired solution. Furthermore, in some embodiments, such a solution can comprise reagents, enzymes, labels or chemical compounds. The wash buffer mobilizes any unbound label causing it to migrate along the strip past the detection zone thus reducing background.

Furthermore, downstream of the test strip 310 is disposed an absorbent substrate 311. The test membrane substrate can overlap or abut to one or both the wicking substrate and absorptive substrate, respectively. Furthermore, in some embodiments, the Test Device upper 306 or lower housing 312 can comprise identity labels 303 and 305, which identify and correspond to an identical identity label on the SCD and can also identify the lot number of the Test Device (e.g., for quality assurance and tracking purposes). Window 304 through the upper housing permits visualization and reading of the results.

In a related embodiment, the matrix further includes an absorbent zone disposed downstream of the lateral flow substrate, membrane or matrix. In one embodiment, a wicking pad can be disposed upstream of the lateral flow membrane. In another embodiment, a wicking pad is disposed directly below the sample entry aperture. Moreover, in preferred embodiments, the test region, which comprises the test and control zones, is observable FIG. 8.

Suitable materials for manufacturing absorbent substrates 311 includes but are not limited to, hydrophilic polyethylene materials or pads, acrylic fiber, glass fiber, filter paper or pads, desiccated paper, paper pulp, fabric, and the like. For example, the lateral flow membrane absorbent zone may be comprised of a material such as a nonwoven spunlaced acrylic fiber, i.e., New Merge (available from DuPont) or HDK material (available from HDK Industries, Inc.), nonwoven polyethylene treated to improve the hydrophobic property of the material.

Safety Means. In some embodiments, a safety means 301 is disposed over the depressible chamber—307 so that the contents of the chamber cannot be accidentally discharged into the channel in fluid communication with the lateral flow membrane. A safety means can be a cover or flange that is lifted or pulled back to expose the depressible chamber or a push button disposed thereon.

Furthermore, such a safety means can function as an adaptor for a specific cognate adaptor, luer or valve present on the distal end of the SCD. Thus, a safety means can cover an aperture into which the distal end of the SCD is engaged, for example, prior to release of a sample into the Test Device. In an additional embodiment, the reader is designed so that a Test Device can only be inserted into a receiving port if the safety cover is first removed. For example, a Test Device with its safety cover removed indicates that a sample has been introduced into the Test Device and running buffer has been released from the compartment 307 upstream of the aperture (adapter/safety cover). In one embodiment, the aperture is disposed above the wicking pad 309.

Gap Means. In some embodiments, a Test Device comprises a gap disposed between the lateral flow membrane (e.g., wicking pad) and the channel in fluid communication with the buffer reservoir. The gap functions to keep any solution contained in the push button reservoir and assay sample separate until the appropriate time according to the assay development FIG. 7. In some embodiments, the gap can be from about 0.5, 1, 1.5, 2, 2.5, 3, 3.5, 4, 5, 6, 7, 8, 9 or 10 mm. In one embodiment the gap is greater than zero and less than 3 mm. Thus, where a user exerts pressure on the compartment—upstream of the sample aperture, the gap as shown between 703 and 704 is forced closed and a solution contained in the compartment—flows in the direction shown by 701 to and through the wicking pad, thus mobilizing the sample through the test strip. As indicated above, the solution can comprise any desired buffer, reagent, chemical compound, dye, label or bead. It should be understood that the gap embodiments disclosed herein can be adapted to any of the Test Device configurations disclosed herein.

Figure 27A:
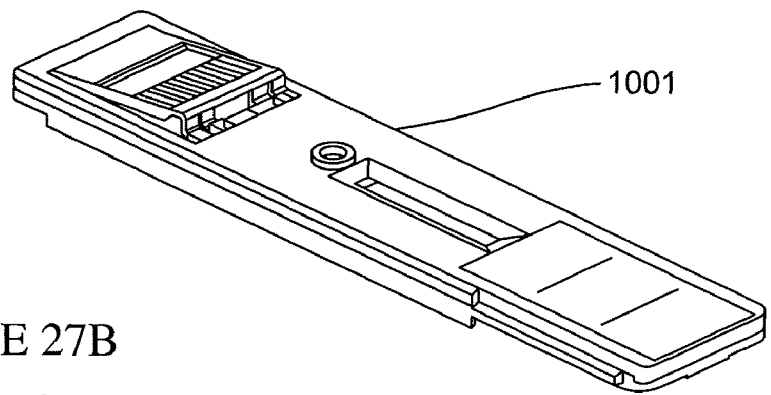
FIG. 27 illustrates various aspects of one Test Device; (A) an assembled Test Device 1001; (B) an unassembled Test Device with upper 1002, lower 1004 and test strip 1003, as well as the aperture/port to receive a sample 1005; (c) closer view of the spring/button compartment which can be pushed down to rupture, break or puncture a buffer/liquid compartment disposed above the membrane/pad 1006 that is in fluid communication with the test strip 1003.

In one embodiment, the test device is a lateral flow test strip, preferably, though not necessarily, encased in a housing, designed to be read by the reader FIGS. 3, 27.

Figure 27B:
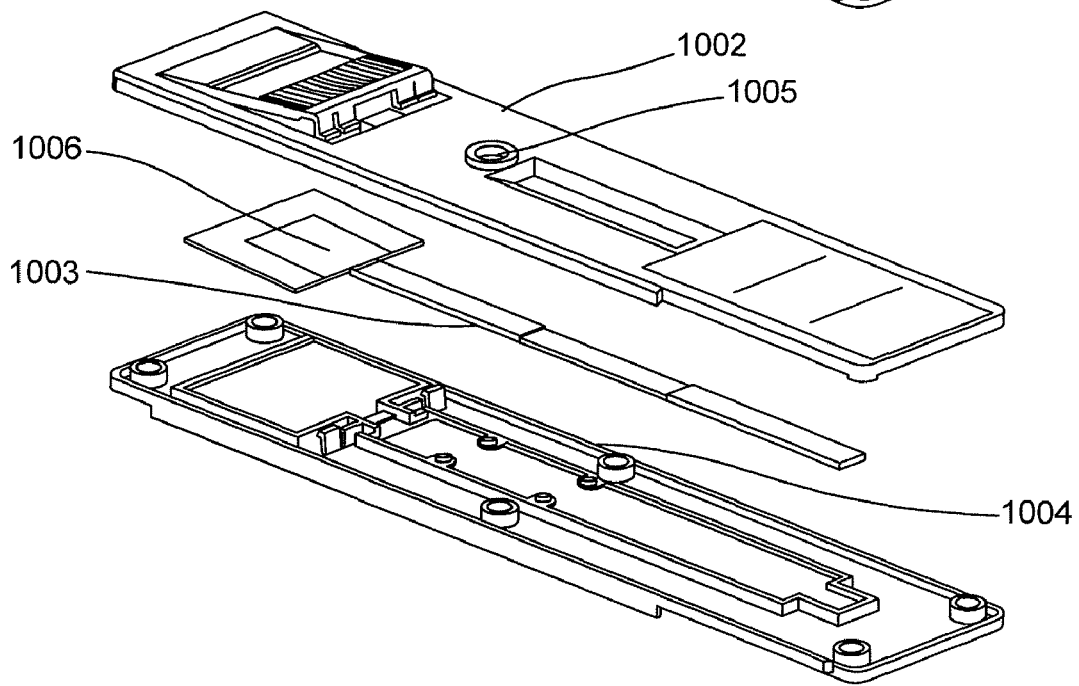

In one embodiment, shown in FIGS. 27 A, B, and C a SCD-processed sample is introduced into the Test Device 1001, a chase or running buffer is subsequently released and follows the specimen through the wicking pad and into the test strip, 1003 where specifically patterned capture agents bind their partner capture probes. Therefore, if a particular analyte is present, it will be bound by a detection probe and capture probe (as described herein above), which capture probe will bind its specific partner capture moiety immobilized on defined spots or lines on the test strip—1003. FIG. 27B shows the components of the test device including the upper housing 1002, lower housing 1004, and aperture 1005.

Figure 27C:
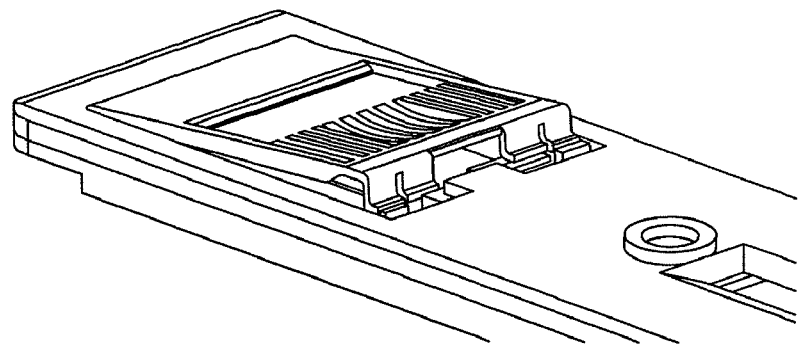

In one embodiment, a wash/running buffer solution is comprised in a foil, sac or buster type packet (e.g., similar to ketchup/condiment packet) which is disposed in the Test Device upstream FIG. 27C of the sample entry port 302, 504, 605, 1005, 1108. The sac or packet can be designed so that it is symmetric about the two orthogonal axes so that it can be loaded into the Test Device easily. Therefore, in one embodiment, the cover of the Test Device disposed over the packet when pressed down can cause the packet to break releasing the contents therein.

In another embodiment, the button portion can comprise a piercing appendage that punctures the packet as the button is depressed thus releasing the contents therein. A leaf spring or cantilever spring FIG. 27C can rest between the packet and the button and results in pressure exerted on the packet to ensure all the contents are released. Further, the geometry of the Test Device is configured so that the wash buffer is directed toward the wicking pad 904/905, 1006. In addition the geometry of the button, spring, and housing also reduces air voids in the packet area allowing the wash buffer to flow in any direction, even against gravity (e.g., uphill), as necessary, but not back into the packet storage area.

The number and size of the holes created, as well as the geometry of the hole created can be adjusted relative to one another in order to allow for predetermined flow of the wash buffer out of the packet.

In one embodiment, the piercing appendage (e.g., needle) will provide a fluid resistance barrier on the top of the packet, allowing fluid to exit the lower portion of the packet in the direction of the wicking pad. The piercing needle can also be tapered in order to achieve or enhance this function.

In one embodiment, the spring FIG. 27C is an integral part of the button, top housing or lower housing FIG. 27B or it can be a separate component altogether that is configured to easily fit and seal the wash/running buffer chamber.

In one embodiment, the sides of the button are designed to minimize pinch points while the button is depressed. Sides can also be designed to provide a baffle-type function, minimizing the risk of liquid exiting the Test Device.

In another embodiment, the geometry of the feature that supports the end of the wicking strip is designed to allow the piercing feature (e.g., needle) to pass through the packet and not allow the packet to form a seal between the packet and the support feature. The action of the needle pierces both the wicking pad and the packet. In another embodiment, the piercing is only of the packet with the wicking pad located directly adjacent to the pierced hole.

In one embodiment, the wash/running buffer in the Test Device is comprised in a breakable/rupturing substrate (e.g., an ampoule). Pressure exerted on a sealing membrane or button breaks the ampoule thus releasing its contents. In one embodiment, a channel, gutter, or trough is designed to direct the buffer to the wicking pad.

In one embodiment, the aperture for receiving the SCD distal end comprises a break-away collar ("Lock Collar") 1104 (FIG. 28A) which—attaches to the SCD assembly and breaks away from the Test Device body 1105 as the SCD 1101 is removed, thus releasing wash or running buffer from a compartment/reservoir 1102 upstream or immediately upstream of said aperture. In yet another embodiment, the Lock Collar when twisted into the lock position allows a sample to be dispensed onto the Test Device while concurrently releasing buffer or wash buffer from an upstream compartment. For example, the Lock Collar will comprise a geometry of channels 1103, holes or openings that line up with openings, channels or holes of the wash/buffer compartment only when the collar is in the lock position. Such a Lock Collar can be utilized with any of the one or more upstream compartments 1102, 1106 that can be utilized to deliver a buffer/wash or any other liquid.

In an alternative embodiment, the SCD 1101 can comprise the Lock Collar 1103 which fits into the Test Device body 1103 and twists from an unlock position to a lock position 1104.

Figure 28A:
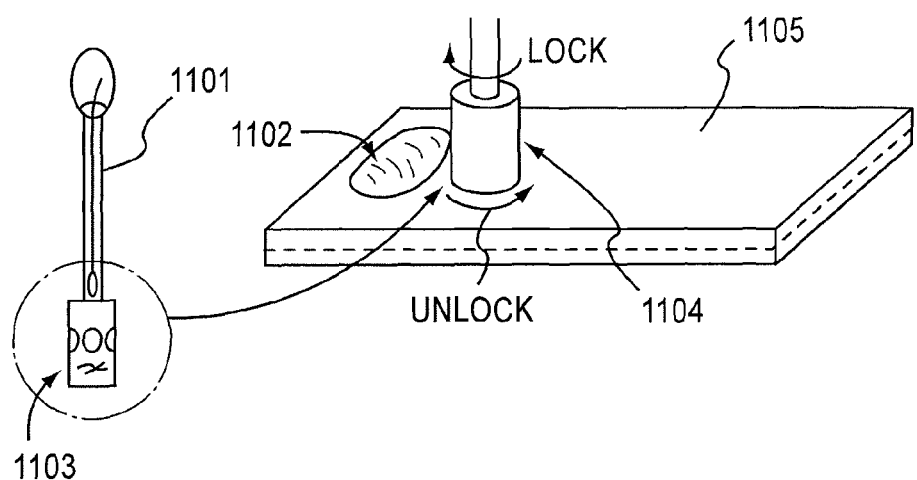
FIG. 28(A) illustrates an embodiment wherein a collar lock is provided that connects an SCD 1101 and Test Device 1105 component, wherein the collar lock 1104 provides channels/pores 1103 in a geometrical configuration that is open to an upstream compartment 1102 only when turned in the lock position (i.e. allowing fluid flow from the upstream buffer/liquid compartment laterally through the Test Device. The upstream compartment 1102 can be an ampoule or formed filled sac.
Figure 28B:
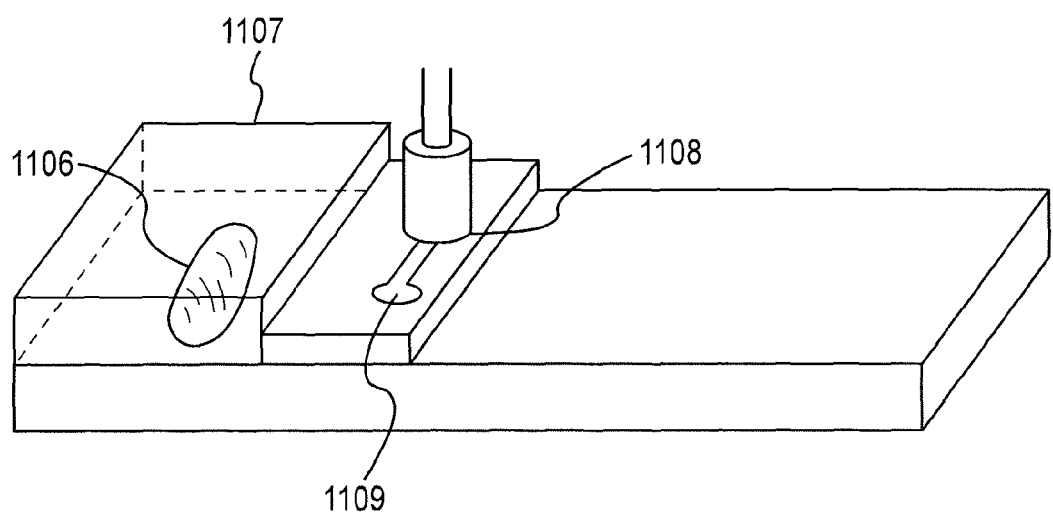
FIG. 28(B) illustrates an embodiment of a Test Device whereby the device comprises a safeguard cover 1107 over the upstream compartment 1106 containing a liquid (e.g., wash/running buffer). Furthermore, the device comprises a reservoir 1109 in fluid communication with the sample aperture/port 1108 which reservoir can comprise a membrane or compartment for retaining an archive sample.
Figure 28C:
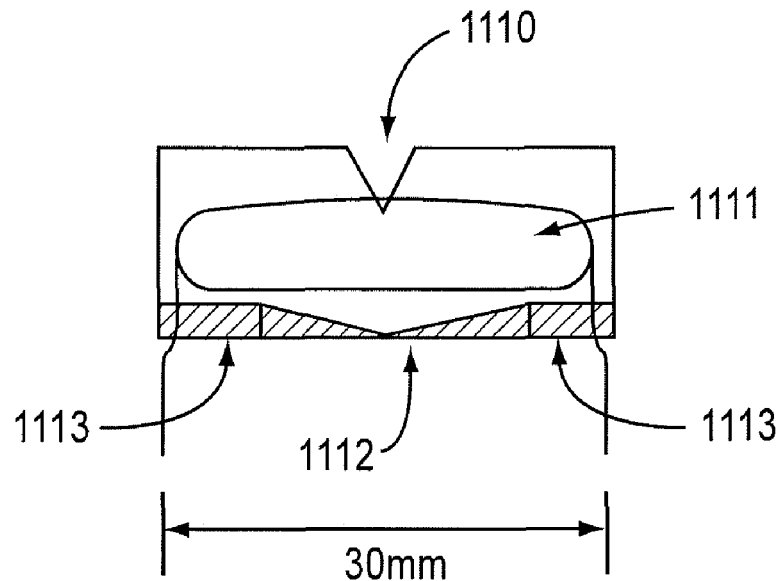
FIG. 28: (C) illustrates a compartment (e.g., ampoule) 1111 disposed in a Test Device with a break point 1110, wherein the Test Device is configured to provide a trough/channel 1112 and supporting substrate 1113 which directs the liquid contents of the ampoule downstream to the test strip; (D) provides an overhead view of the compartment comprising a sac/ampoule 1114 positioned upstream of where sample introduction occurs 1115, configured to provide a fluid ramp 1119 and supports 1118 through which the contents of the compartment to a space 1117 that is in fluid communication with a wicking pad 1116.
Figure 28D:
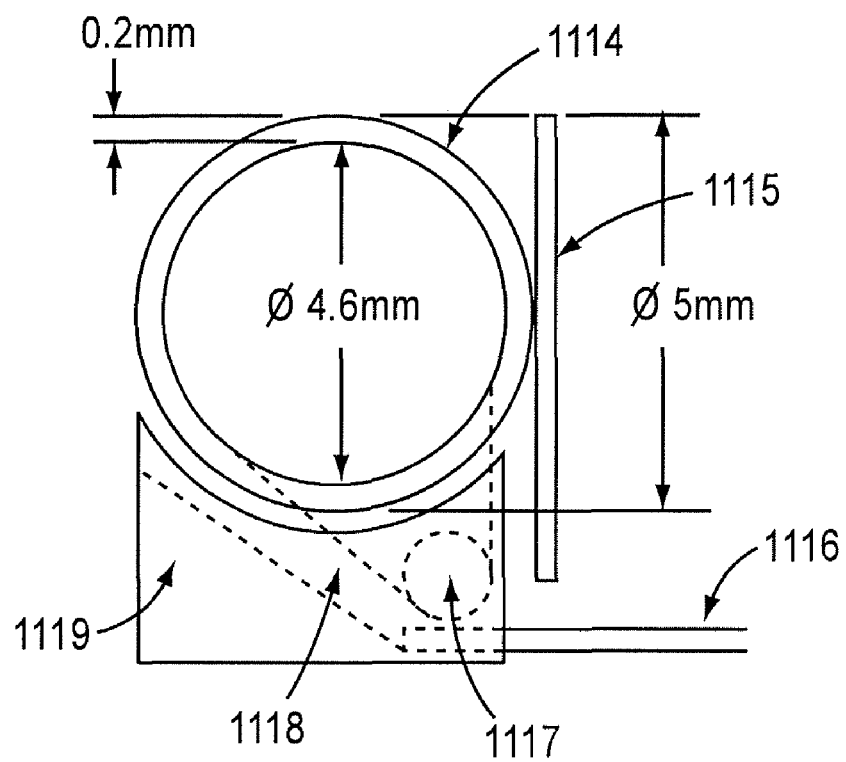

In one embodiment as depicted in FIG. 28B, the upstream wash buffer compartment comprises a soft membrane (e.g., form fill seal pack) or ampoule that is easily ruptured broken upon exertion of minimal force (e.g., user pressing with finger). Such an onion skin compartment—1106, can be further covered by a hard removable cover 1107 which prevents accidental breakage of the onion skin. The sample enters the test device through a port 1109 and the device may have a narrow channel 1109 for recovery of an archival sample.

Figure 4:
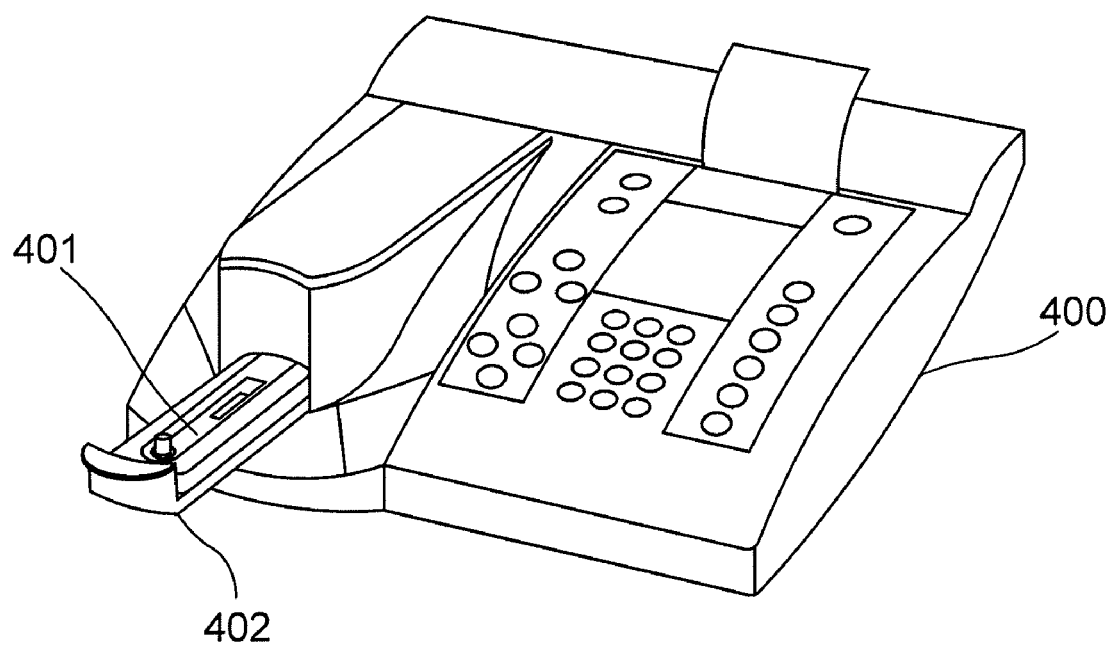
FIG. 4 illustrates a reader.
Figure 8:
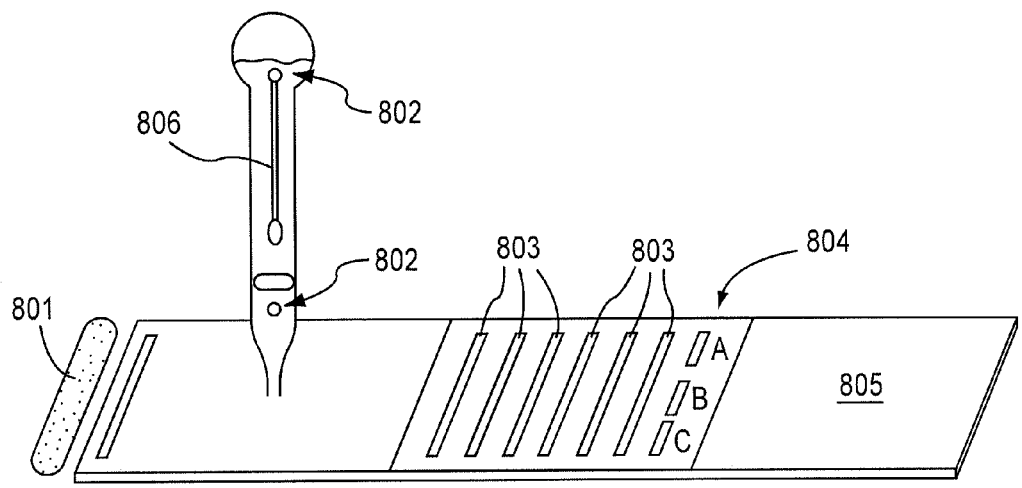
FIG. 8 illustrates a sample collection device and test device.

As shown in FIG. 8 the sample is delivered to the test strip by the SCD 802 which includes the stem and swab 806. Upstream of the test strip is the compartment 801 with wash buffer or other fluid. The test strip includes test zones 803—, and control zones A, B, C 804. The detection probe, via the conjugate label, will provide a detectable signal. The Test Device is then inserted into a reader 400 as shown in FIG. 4, where the signal from the label is measured and/or detected. In another embodiment, the test strip 401 can be inserted into a moveable tray 402 in the reader after the short assay processing period has completed for a very short read period (~20 seconds), this allows for a much higher through put of tests with one reader. Further, in another embodiment, the test strip can be inserted into the reader prior to addition of the sample.

In any of the embodiments herein directed to a wash/running buffer release from a chamber upstream of the sample (e.g., sample entry port), a time delay feature can be configured into the Test Device, so that a period of time passes between introduction of the sample and the release of the wash/running buffer. For example, a dry wicking pad substrate swells when wet (i.e., after wash buffer release) and due to the swelling connects and otherwise disconnected wicking strip FIG. 34, For example, a sample is applied 1405. The ampoule or substrate 1401 comprising the wash buffer is broken/ruptured to release the liquid into the dry wicking pad portion 1402, which swells 1403 and provides liquid communication to the wicking pad portion containing the sample 1405. The sample/buffer run through the test strip via the wicking pad 1406.

In another embodiment, a predetermined length density of fibrous membrane is placed in between the wash buffer compartment and the wicking membrane, which fibrous membrane can delay the contact of the wash buffer to the wicking membrane thus functioning as a time delay mechanism. Buffer wicks down the fibrous membrane and accumulates on the end of the membrane fibers until it reaches the wicking membrane and flows through with the sample disposed on the wicking membrane. In another embodiment, the buffer accumulates at the ends of the membrane fibers until there is enough volume to bridge a gap separating the fibrous membrane from the wicking membrane.

In other embodiments, a plunger or spring mechanism is configured into the Test Device, which functions to reduce the compartment/ampoule volume, thus ensuring the contents therein are dispersed onto a wicking pad, A plunger can be moved forward by the user exerting pressure on the button or a spring loaded plunger can be driven forwarded in an automated fashion (e.g., when placed in the reader). The plunger forms a seal as it drives forward so that the liquid's only means of exit is through to the wicking pad.

In one embodiment, the liquid transport along the test strip is based upon capillary action. In a further embodiment, the liquid transport along the matrix is based on non-bibulous lateral flow, wherein all of the dissolved or dispersed components of the liquid sample are carried at substantially equal rates and with relatively unimpaired flow laterally through the matrix, as opposed to preferential retention of one or more components as would occur, e.g., in materials that interact, chemically, physically, ionically or otherwise with one or more components. See for example, U.S. Pat. No. 4,943,522, hereby incorporated by reference in its entirety.

Any suitable material can be used to make the devices disclosed herein, such material including a rigid or semi-rigid, non-water-permeable material, such as glass, ceramics, metals, plastics, polymers, or copolymers, or any combination thereof. In some embodiments, either the SCD or Test Device comprise a plastic, polymer or copolymer such as those that are resistant to breakage, such as polypropylene, polyallomer, polycarbonate or cycloolefins or cycloolefin copolymers. Furthermore, devices of the invention can be made by appropriate manufacturing methods, such as, but not limited to, injection molding, blow molding, machining or press molding.

As used herein, test strip substrate refers to the material to which a capture moiety is linked using conventional methods in the art. A variety of materials can be used as the substrate, including any material that can act as a support for attachment of the molecules of interest. Such materials are known to those of skill in this art and include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone (PVP), rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamide, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media or a complex material composed of a solid or semi-solid substrate coated with materials that improve the hydrophilic property of the strip substrate, for example, polystyrene, Mylar, polyethylene, polycarbonate, polypropylene, polybutylene, metals such as aluminum, copper, tin or mixtures of metals coated with dextran, detergents, salts, PVP and/or treated with electrostatic or plasma discharge to add charge to the surface thus imparting a hydrophilic property to the surface.

In one embodiment, the lateral flow membrane is comprised of a porous material such as high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. In another embodiment, the label zone is comprised of a porous material such as a nonwoven spunlaced acrylic fiber (similar to the sample receiving zone), e.g., New Merge or HDK material. Often, the porous material may be backed by, or laminated upon, a generally water impervious layer, e.g., Mylar. When employed, the backing is generally fastened to the matrix by an adhesive (e.g., 3M 444 double-sided adhesive tape). Typically, a water impervious backing is used for membranes of low thickness. A wide variety of polymers may be used provided that they do not bind nonspecifically to the assay components and do not interfere with flow of the fluid sample. Illustrative polymers include polyethylene, polypropylene, polystyrene and the like. On occasion, the matrix may be self-supporting. Other membranes amenable to non-bibulous flow, such as polyvinyl chloride, polyvinyl acetate, copolymers of vinyl acetate and vinyl chloride, polyamide, polycarbonate, polystyrene, and the like, can also be used. In yet another embodiment the lateral flow membrane is comprised of a material such as untreated paper, cellulose blends, nitrocellulose, polyester, an acrylonitrile copolymer, and the like. The label zone may be constructed to provide either bibulous or non-bibulous flow, frequently the flow type is similar or identical to that provided in at least a portion of the sample receiving zone. In a frequent embodiment, the label zone is comprised of a nonwoven fabric such as Rayon or glass fiber. Other label zone materials suitable for use by the present invention include those chromatographic materials disclosed in U.S. Pat. No. 5,075,078, which is herein incorporated by reference.

In a frequent embodiment, the test strip substrate is treated with a solution that includes material-blocking and label-stabilizing agents. Blocking agents include bovine serum albumin (BSA), methylated BSA, casein, acid or base hydrolyzed casein, nonfat dry milk, fish gelatin, or similar. Stabilizing agents are readily available and well known in the art, and may be used, for example, to stabilize labeled reagents. In some embodiments, the upstream compartment containing a solution 307 can comprise multiple ampules, which can be selectively punctured or broken to release their contents. Therefore, in one embodiment, blocking reagents are contained in one ampule which is utilized to pre-treat (e.g., "block") the test strip (i.e., lateral flow membrane), while the additional ampule is reserved for washing the sample through the test strip.

In various disclosures herein, the test strip/lateral flow membrane comprises multiple test zones, one of which is referenced 803 in FIG. 8. Test zones generally contains a pre-selected capture moieties, where a pre-selected region comprises capture moieties that are partners for capture moieties conjugate to analyte-specific binding agents, such as monoclonal antibodies. In many of the presently contemplated embodiments, multiple types of labeled reagents are incorporated in SCD such that they may permeate together with a fluid sample contacted in the device. These multiple types of labeled reagent can be analyte specific or control reagents and may have different detectable characteristics (e.g., different colors) such that one labeled reagent can be differentiated from another labeled reagent if utilized in the same device, or in a preferred embodiment, having different capture moieties. As the labeled reagents are frequently bound to a specific analyte of interest and are subsequently processed through to a Test Device comprising a test strip, differential detection of labeled reagents having different specificities (including analyte specific and control labeled reagents) may be a desirable attribute. However, frequently, the ability to differentially detect the labeled reagents having different specificities based on the label component alone is not necessarily due to the presence of defined test and control zones in the device, which allow for the accumulation of labeled reagent in designated zones.

In some embodiments, each detection probe is conjugated to a fluorescent label emitting a different wavelength. Therefore, where a plurality of specific binding agents are comprised in a SCD, where the plurality comprises several different groups of specific binding pairs, each binding pair for a given group comprises labels different than any other group, where the multiple groups make up the plurality of specific binding agents. For example, a group of specific binding antibodies to influenza A can be conjugated to one type of fluorescent label (i.e., detection probes conjugated to a first fluorescent label), while a group of specific binding antibodies (i.e., detection probes conjugated to a second fluorescent label), and a third, fourth or fifth group can each comprise detection probes conjugated to different fluorescent labels. Of course, it should be evident that detection probes can also comprise a combination of different types of labels (e.g., first group comprising a fluorescent label, while second group a metal, while a control can comprise a chromophore). In one embodiment, the fluorescent labels emit wavelengths that are sufficiently distinct so that several test lines can be differentiated.

The present description provides for the development and use of single or multiple control zones in a single immunoassay device that are positioned in a predetermined manner relative to individual test zones thereby allowing easy identification of each of the one or more analytes of interest tested for in the device. The present description further provides for the making of control zones of various shapes, physical or chemical identities, and colors. In part, the use of such control zones allows for immunoassay devices that are easy to use, and allow for the identification of multiple analytes during a single assay procedure. (See, Example 11).

In one embodiment, the Test Device does not include any reagents contained therein that are capable of specifically binding to an analyte (e.g., antibody that is specific for H5N1).

The test region generally includes one or more control zone that is useful to verify that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

In some embodiments, a labeled control reagent is introduced into the fluid sample flow either in the SCD or in the Test Device. For example, in the Test Device, control reagents can be included in the upstream solution/buffer reservoir, which are described herein FIG. 3. In another example, the labeled control reagent may be added to the fluid sample before the sample is applied to the Test Device, e.g., present in the mixing subchamber in the SCD.

Exemplary functions of the labeled control reagents and zones include, for example, the confirmation that the liquid flow of the sample effectively solubilized and mobilized the labeled reagents from the SCD, which are captured in one or more defined test zones. Furthermore, controls can confirm that a sufficient amount of liquid traveled correctly through the test strip test and control zones, such that a sufficient amount of capture moieties could react with the corresponding specific capture probes complexed to a specific analyte (i.e., via the antigen specific binding agent). Further, control reagents confirm that the immunocomplexes (e.g., analyte-analyte specific binding agent) migrate onto the test region comprising the test and control zones, cross the test zone(s) in an amount such that the accumulation of the labeled analyte would produce a visible or otherwise readable signal in the case of a positive test result in the test zone(s). Moreover, an additional function of the control zones may be to act as reference zones which allow the user to identify the test results which are displayed as readable zones.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest.

In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in all amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form). Examples of contemplated pre-designed signals include signals of equal intensities in each control zone, or following a desired pattern of increasing, decreasing or other signal intensity in the control zones.

In another embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectable signal (e.g., be of the same color) or provide distinguishable detectable signals (e.g., have different colored labels or other detection systems) upon accumulation in the control zone(s).

In yet another embodiment, the control zones may include a combination of the two types of control zones described in the two previous embodiments, specifically, one or more control zones are able to restrain or bind a single type of labeled control reagent, and other control zones on the same test strip will be capable of binding one or several other specifically labeled control reagents.

In one embodiment, the labeled control reagent comprises a detectable moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

In another embodiment, the detectable moiety which forms the label component of the labeled control reagent is the same detectable moiety as that which is utilized as the label component of the analyte of interest labeled test reagent. In a frequent embodiment, the label component of the labeled control reagent is different from the label component of the labeled test reagent, so that results of the assay are easily determined. In another frequent embodiment, the control label and the test label include colored beads, e.g., colored latex. Also frequently, the control and test latex beads comprise different colors.

In a further embodiment, the labeled control reagent includes streptavidin, avidin or biotin and the control capture partner includes the corresponding member of such specific binding pairs, which readily and specifically bind with one another. In one example, the labeled control reagent includes biotin, and the control capture partner includes streptavidin. The artisan will appreciate that other members of specific binding pairs can alternatively be used, including, for example, antigen/antibody reactions unrelated to analyte. In yet other embodiment, capture partners can include any of the binding moieties disclosed herein.

The use of a control zone is helpful in that appearance of a signal in the control zone indicates the time at which the test result can be read, even for a negative result. Thus, when the expected signal appears in the control line, the presence or absence of a signal in a test zone can be noted.

In still further embodiment, a control zone comprising a mark that becomes visible in the test region when the test region is in a moist state is utilized. Control zones of this type are described in U.S. patent application Ser. No. 09/950,366, filed, Sep. 10, 2001, currently pending and published as U.S.

patent application Publication No. 20030049167, and Ser. No. 10/241,822, filed Sep. 10, 2002, currently pending and published as U.S. patent application Publication No. 20030157699.

In occasional embodiments, one or more control zones of this type are utilized. In another embodiment, a combination of control zones of the type utilizing labeled control reagents and control zone and of the type that display the control zone when in a moist state can be used. This allows a simple way to formulate control zones while allowing to use a reagent-based control zone to ascertain that the re-solubilization and mobilization of the reagents in SCD-processed samples has been effective, and that the specific reactions took place as expected, all along the path defined Test Device, wick, test strip and absorbent pad. The present embodiment includes the use of one or more control zones that become visible when the test region is in the moist state for each of the control zones of an assay, except the control zone on the distal or downstream end of the test strip.

The present description further provides means to build a rapid, multi-analyte assay, which is needed in many fields of environmental monitoring, medicine, particularly in the field of infectious disease. For example, contemplated devices include those useful for the differential diagnosis of Flu A or Flu B, and subtypes thereof (e.g., Flu A, H5N1) which may result in different treatments, or the differential diagnosis of Flu A, Flu B, and/or RSV in one step. Such devices permit the use of a single sample for assaying multiple analytes at once, and beneficially allows for a considerable reduction of the hands-on time and duration of the diagnostic process for the benefit of the doctor, or user in general. As such a plurality of immunoreagents can be utilized in an SCD of the invention, where said plurality comprises populations of specific binding agents, comprising pairs conjugated respectively to label and capture moiety, whereby said plurality comprise multiple populations each specific for a different analyte as compared to any other population. For example, the plurality of immunoreagents can be specific for several types of one pathogen or different pathogens.

A variety of analytes may be assayed utilizing devices and methods of the present disclosure. In a particular device useful for assaying for one or more analytes of interest in a sample, the collection of analytes of interest may be referred to as a panel. For example, a panel may comprise any combination (or all of) of influenza A, influenza B, influenza A subtypes, respiratory syncytial virus (RSV), adenovirus, and different types of Parainfluenza viruses (for example Types 1, 2, 3 etc.). Another panel may comprise testing for a selection of one or more of upper respiratory infection including, for example, *Streptococcus pneumoniae, Mycoplasma pneumoniae* and/or *Chlamydia pneumoniae*. Yet another panel can be devised for the diagnosis of sexually transmitted disease including, for example, *Chlamydia, Trichomonas* and/or Gonorrhea. In each case, a particular panel devised to provide signals on the Test Device for a particular series of analytes is readily obtained by incorporating a different set of detection and capture probes in the SCD, which is described herein. Therefore, a particular SCD will provide all the reagents necessary to detect a particular panel of analytes which are detected when using a Test Device employing test strips that have detection reagents that are not specific for the analytes of interest. In other embodiments, a broad scope Test Device can comprise non-specific capture moieties for several series of analytes from related or distinct pathogens, e.g., detection of HIV and HCV antigens; HIV and tuberculosis, Influenza A, B, and subtypes of A, bacterial and viral infections. Thus a single Test Device can be used with SCDs comprising immunoreagents for a different panel of analytes, providing enhanced efficiency and cost effectiveness.

For example, a panel may optionally include a variety of other analytes of interest, including SARS-associated coronavirus, influenza A; a hepatitis panel comprising a selection of hepatitis B surface Ag or Ab, hepatitis B core Ab, hepatitis A virus Ab, and hepatitis C virus; a phospholipids panel comprising a selection of Anticardiolipin Abs (IgG, IgA, and IgM Isotypes); an arthritis panel comprising a selection of rheumatoid factor, antinuclear antibodies, and Uric Acid; an Epstein Barr panel comprising a selection of Epstein Barr Nuclear Ag, Epstein Barr Viral Capsid Ag, and Epstein Barr Virus, Early Antigen; other panels include HIV panels, Lupus panels, H. Pylori panels, toxoplasma panels, herpes panels, Borrelia panels, rubella panels, cytomegalovirus panels, panels testing for recent myocardial infarction with analytes comprising an isotype of Troponin with myoglobin and/or CKMB and many others. One of skill in the art would understand that a variety of panels may be assayed via the immunoassays utilizing the devices disclosed herein. Immunoassay methods are known in the art. See, e.g., CURRENT PROTOCOLS IN IMMUNOLOGY (Coligan, John E. et. al., eds. 1999).

Numerous analytical devices known to those of skill in the art may be adapted in accordance with the present invention, to detect multiple analytes. By way of example, dipstick, lateral flow and flow-through devices, particularly those that are immunoassays, may be modified in accordance herewith in order to detect and distinguish multiple analytes. Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642. Other lateral flow devices that may be modified for use in distinguishable detection of multiple analytes in a fluid sample include U.S. Pat. Nos. 4,703,017, 6,187,598, 6,352,862, 6,485,982, 6,534,320 and 6,767,714. Exemplary dipstick devices include those described in U.S. Pat. Nos. 4,235,601, 5,559,041, 5,712,172 and 6,790,611. It will be appreciated by those of skill in the art that the aforementioned patents may and frequently do disclose more than one assay configuration and are likewise referred to herein for such additional disclosures. Advantageously, the improvements described are applicable to various assay, especially immunoassay, configurations.

SCDs or Test Devices of the invention can be configured to be utilized with existing analyte detection systems. For example, an SCD of the invention can be configured for use with an existing test device, or an existing test device can be configured/modified pursuant to disclosures herein for a Test Device. Some exemplary devices that can be modified in such a fashion include dipstick, lateral flow, cartridge, multiplexed, microtiter plate, microfluidic, plate or arrays or high throughput platforms, such as those disclosed in U.S. Pat. Nos. 4,235,601, 4,632,901, 5,559,041, 5,712,172, and 6,790,611, 6,448,001, 4,943,522, 6,485,982, 6,656,744, 6,811,971, 5,073,484, 5,716,778, 5,798,273, 6,565,808, 5,078,968, 5,415,994, 6,235,539, 6,267,722, 6,297,060, 7,098,040, 6,375,896, 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, and 6,306,642. Other lateral flow devices that may be modified for use in distinguishable detection of multiple analytes in a fluid sample include U.S. Pat. Nos. 4,703,017, 6,187,598, 6,352,862, 6,485,982, 6,534,320 and 6,767,714, 7,083,912, 5,225,322, 6,780,582, 5,763,262, 6,306,642, 7,109,042, 5,952,173, and 5,914,241. Exemplary microfluidic devices include those disclosed in U.S. Pat. Nos. 5,707,799, 5,837,115 and WO2004/029221. Each of the preceding patent disclosures is incorporated by reference herein in its entirety.

Reader.

The systems and methods include an immunoassay device in combination with a reader 400, particularly a reader 400 with a built in computer, such as a reflectance and/or fluorescent based reader, and data processing software employing data reduction and curve fitting algorithms, optionally in combination with a trained neural network for accurately determining the presence or concentration of analyte in a biological sample. As used herein, a reader refers to an instrument for detecting and/or quantitating data, such as on test strips comprised in a Test Device 401. The data may be visible to the naked eye, but does not need to be visible. The methods include the steps of performing an immunoassay on a patient sample, reading the data using a reflectance and or fluorescent based reader and processing the resultant data using data processing software employing data reduction. Preferred software includes curve fitting algorithms, optionally in combination with a trained neural network, to determine the presence or amount of analyte in a given sample. The data obtained from the reader then can be further processed by the medical diagnosis system to provide a risk assessment or diagnosis of a medical condition as output. In alternative embodiments, the output can be used as input into a subsequent decision support system, such as a neural network, that is trained to evaluate such data.

In various embodiments, the reader can be a reflectance, transmission, fluorescence, chemo-bioluminescence, magnetic or amperometry reader (or two or more combinations), depending on the signal that is to be detected from the Test Device. (e.g., LRE Medical, USA). In one embodiment, the reader comprises a receiving port designed to receive a Test Device, but where the Test Device can only be inserted into the receiving port if a depressible (e.g., push button) means upstream of the sample entry aperture has been depressed allowing the Test Device to fit into the receiving port 402. Thus, in such an embodiment, the Test Device is placed in a reader only when the contents of the solution reservoir (e.g., wash buffer) has been released, ensuring that the sample has been "run-through" the lateral flow membrane comprised in the Test Device.

In one embodiment, the reader is a UV LED reader which detects a fluorescence signal. The fluorescence signal is excited by a light emitting diode that emits in the UV region of the optics spectrum and within the absorbance peak of the fluorescence signal (e.g., lanthanide label). The emitted fluorescence signal is detected by a photodiode and the wavelength of the signal detected may be limited using a long pass filter which blocks stray emitted light and accepts light with wavelengths at and around the peak emission wavelength of the fluorescence emitting label. In other embodiments, the long pass filter may be replaced by a band pass filter. Furthermore, the excitation light may be limited by a band pass filter.

In another embodiment, the diode is a UV laser diode. Any conventional UV, LED or photodiode may be utilized.

In any such embodiments, the excitation source and the detector are mounted in a single machine or molded block. For simplified reading of the fluorescent signals generated on the test strip. In a further embodiment, such a machine also comprises hard standards (e.g., FIG. 33) as described herein.

In one embodiment, the axis of the excitation light is at 90 degrees to the Test Device or test strip comprised in a Test Device. Further, the axis of the emitted light is at an angle other than 90 degrees to the test strip.

In one embodiment the wavelength of the excitation light is limited by a short pass filter. In yet another embodiment the wavelength of the excitation light is limited by a combination of band pass filter and short pass filter. In yet a further embodiment, the wavelength of the detected light is limited by a combination of band pass and long pass filter. The reader can be configured to detect any of the signal emitters/labels described herein. In one embodiment, the label is any of the lanthanides described herein. In a further embodiment, the lanthanide used is Europium.

As indicated herein, in one embodiment, the reader is configured to comprise one or more hard standards. Thus, the reader can be machined to provide a implement (e.g., a jig) to hold 0.5, 0.75, 1, 1.25, 1.5, 1.75, 2, 2.25, 2.5 or 3 mm standards (e.g., encased in acrylic as described herein), which standard is disposed on about 3, 4, 5, or 6 mm centers. (e.g., See FIG. 33A, 33B, 34).

In one embodiment, the reader is adapted with a receiving port for the Test Device FIG. 27, which itself is configured with a safeguard FIG. 27C. In one embodiment the reader will accept but not process the Test Device 401 if the push button has not been depressed, or the reader will accept and read the Test Device, but will reject the result if the Wash Buffer control does not yield a positive signal, etc. In this latter embodiment, a wash/running buffer disposed in a compartment/sac disposed upstream of the sample FIG. 27C can contain a control signal (e.g., label emitting at a different wavelength) which the reader is programmed to detect.

The signal obtained by the reader is processed using data processing software employing data reduction and curve fitting algorithms, optionally in combination with a trained neural network, to give either a positive or negative result for each test line, or a quantitative determination of the concentration of each analyte in the sample, which is correlated with a result indicative of a risk or presence of a disease or disorder. This result can optionally be input into a decision support system, and processed to provide an enhanced assessment of the risk of a medical condition as output. In one embodiment, the entire procedure may be automated and/or computer-controlled.

Multi analyte Point of Care System.

Rapid influenza tests have been marketed for years. Most of these tests are lateral flow immunoassay tests using either gold or latex as the visualization agent. While most of new rapid immunoassays are able to differentiate influenza Type A from influenza Type B, only few of them have both test lines for type A and type B on the one strip. However, none of these tests are designed to differentiate subtypes of influenza type A. Therefore these tests may be able to detect avian influenza, none of them can tell if a patient is infected by a seasonal flu A virus or a more severe Type A subtype such as H5N1 termed avian influenza (or current potential pandemic subtype of influenza A). The present invention is designed on concepts that when applied are to yield a highly sensitive assay with improved reproducibility, able to detect type A, type B and differentiate subtype H5N1 from seasonal flu (subtypes H1 and H3) and is easy to use. Efforts have been made to apply multiple new technologies with a new device design, such as pre-mixing of the sample with the conjugate, use of a chasing or wash buffer to reduce background, employ a unique generic capture reagent pRNA which allows multiple analytes detection at high sensitivity, fluorescent label which is highly sensitive, etc. The combination of these approaches enables a novel and highly effective influenza rapid test that is much more sensitive, provides low cost production, ease of operate and has the ability to differentiate seasonal flu from pandemic avian flu H5N1.

In one embodiment, the combination of features described herein are responsible for the excellent sensitivity and reproducibility of assays constructed in accordance with the invention to use the novel system, which serves to concentrate ligand from a test sample at a test site the test strip, and the use of a metal sol or other colored particle as a marker system which permits persistent visual observation of the fluorescence over a period of one to several hours beyond the minimum time needed to complete the assay). Background noise is reduced while maintaining excellent sensitivity by including in the test implement a controllably released buffer that functions to wash away excess/unbound label. Furthermore, one or more control sites whose color is compared with the test site. In some embodiments, a filtration means is comprised in the sample implement or in the test implement, which filtration means limits the introduction to the test site of contaminants from the crude or unprocessed biological sample. In yet other embodiments, the filtration means is a membrane and includes detection and capture probes disposed thereon 604.

Assay Methods.

In one embodiment, an assay method comprises the steps of applying the sampling implement to a subject or subject's biological sample, to collect a sample (e.g., swabbing inside the nose, mouth, throat, ear; applying a sampling element to a biological sample obtained from a subject), inserting the collection implement into the sample collection device housing chamber, squeezing the upper chamber to break open the snap-valve and allowing a buffer to run down to the sampling implement, thus immersing the biological sample disposed thereon and running the mixture of buffer and sample into a reaction chamber (e.g., lower chamber) where a plurality of capture and detection probes bind to their specific target analyte. Subsequently or concurrently, the mixture is expelled from the distal end of the SCD into a Test Device comprising immobilized capture moieties designed to capture a complex of analyte and detection/capture probe, via the complementary capture moiety linked to a capture probe. Thus, a particular capture probe is designed to be complementary to an immobilized capture moiety for one particular analyte. Furthermore, as disclosed herein, capture moieties are disposed on a lateral flow membrane in distinct positions/patterns, where a single line or spot(s) if detected via the signal emitting label, allows qualitative and/or quantitative detection of a particular analyte. Therefore, by patterning particular capture probes on the lateral flow membrane, an assay method can detect a panel of the same or related infectious agent or even unrelated infectious agents, as disclosed herein.

In some embodiments a sandwich immunoassay format is utilized but any conventional format, including a competitive assay, may be used. Typically, an indirect capture of the formed immunocomplex is utilized in the sandwich format. One or more analytes in the sample are contacted with one or more pairs of a detection probe and a capture probe. Each pair contains the detection probe which is a conjugate comprising a label and a specific binding agent (SBA) capable of specifically binding to an analyte and a capture probe which is a conjugate comprising a detection moiety and another SPA capable of specifically binding the same analyte. Examples of specific binding agent(s) include antibodies, aptamers. In one embodiment, each of two SBAs are specific binding partners in that each bind the same target antigen or analyte. Examples of SBAs are known in the art and include but are not limited to antibodies, aptamers or oligonucleotides. In the sandwich assay, the analyte is simultaneously bound by both the detection probe and the capture probe. The detection moiety is part of a specific binding pair and the other partner of the pair is immobilized on the test device to capture the immunocomplex as it flows through the test device. The use of different capture moiety pairs for each different analyte permits the detection of multiple analyte on one test device from a single sample and reaction sequence. In most cases, the labels for each analyte are different. However, by having a specific location for each analyte as a capture zone with distinct capture moiety pairs for each analyte, it is possible to utilize the same label for all of the analyte.

Examples of sandwich immunoassays performed on test strips are described in U.S. Pat. Nos. 4,168,146 and 4,366,241, each of which is incorporated herein by reference. Examples of competitive immunoassay devices are those disclosed by U.S. Pat. Nos. 4,235,601, 4,442,204 and 5,208,535, each of which is incorporated herein by reference. Some additional exemplary devices that can be adapted to incorporate one or more components of the present invention include dipstick, lateral flow, cartridge, multiplexed, microtiter plate, microfluidic, plate or arrays or high throughput platforms, such as those disclosed in U.S. Pat. Nos. 6,448,001, 4,943,522, 6,485,982, 6,656,744, 6,811,971, 5,073,484, 5,716,778, 5,798,273, 6,565,808, 5,078,968, 5,415,994, 6,235,539, 6,267,722, 6,297,060, 7,098,040, 6,375,896, 7,083,912, 5,225,322, 6,780,582, 5,763,262, 6,306,642, 7,109,042, 5,952,173, and 5,914,241. Exemplary microfluidic devices include those disclosed in U.S. Pat. No. 5,707,799 and WO2004/029221.

In one such scheme, a test strip contains an enzyme labeled, mobile binding partner for an analyte which is in a zone downstream from a sample application zone. If an analyte is present in the test sample, it will combine with its labeled binding partner to form a complex which will flow along the strip to a detection zone which contains a substrate for the enzyme label and capable of providing a detectable enzymatic response, e.g., color response in the presence of the enzyme. The strip also contains a zone in which a predetermined amount of analyte is immobilized, so that any labeled binding partner which does not combine with the analyte, due to the absence of the analyte in a sample, will be captured and thereby inhibited from reaching the detection zone.

Alternatively the strip can contain a binding partner bears a moiety having a detectable physical property. For example, the labeled binding partner can include one or more moieties, e.g., chemical groups detectable on the basis of certain physical properties including without limitation colored species of fluorescers, phosphorescent molecules, radioisotopes, electroactive moieties, particles such as gold, etc.

In another scheme, the detection is based on the competition between a specific analyte, e.g., ligand, antigen or antibody, the amount of which is to be determined in a sample, and a known amount of tracer, which is generally the analyte or appropriate analog hereof in labeled form, with the analyte and tracer competing for a limited number of available binding sites on a binder which is specific towards the analyte and tracer. For example, if the concentration of tracer and binder is fixed and the only variable is the level of analyte, then the unknown level of analyte can be measured by determining the amount of bound and/or free tracer in the system. The values determined in the assay are compared with the values given by a range of known amounts of the analyte treated in the same manner, and by such comparison, one can determine the amount of analyte in the sample.

In general, the tracers used in such assays require either instrumentation and/or treatment of the tracer in order to determine the tracer in the bound and/or free portion of the assay as a measure of analyte. For example, in an assay in which an enzyme is used as the label or marker for the tracer, the enzyme must be developed with a suitable developer. When the label or marker is a fluorescent material, the tracer in the bound and/or free portion is determined by the use of appropriate instrumentation for determining fluorescence.

Alternatively the tracer used in the assay is a ligand labeled with a particulate label which is visible when bound to the binder on the support or when bound to the analyte bound to the binder on the support, without further treatment, and wherein the ligand is bound by either the binder or analyte. See also U.S. Pat. No. 4,703,017, which is incorporated herein by reference.

In another particular aspect, the non-nucleic acid based screening test of the present invention includes any solid phase, lateral flow, or flow-through tests. In general, solid phase immunoassay devices incorporate a solid support to which one member of a ligand-receptor pair, usually an antibody, antigen, or hapten, is bound. Common early forms of solid supports were plates, tubes, or beads of polystyrene, which were known from the fields of radioimmunoassay and enzyme immunoassay. More recently, a number of porous materials such as nylon, nitrocellulose, cellulose acetate, glass fibers, and other porous polymers have been employed as solid supports In one embodiment, a sample is collected from a subject via a sampling implement 102 and placed back into the cylinder housing of the SCD device 200. The SCD can first be inserted into a Test Device, or prior to insertion into a Test Device, a solution contained in the upper sealed chamber of the SCD is released to effect washing the sample and solution into a mixture downwards into a reaction chamber. In the reaction chamber is disposed either liquid or solid reagents comprising detection and capture probes that target one or more different analytes as disclosed herein, thereby forming a complex of analyte bound to detection and capture probe. The sample is then expelled from the SCD into a Test Device through an aperture that seals the contact between the SCD and the Test Device from the outside environment (e.g., preventing any spillage, aerosol or contamination). The sample mixture can flow as a result of gravity or the force of air pressure produced by squeezing the SCD (e.g., upper sealed chamber), into a Test Device. The sample is driven by capillary force and/or by wash buffer comprised in the Test Device 307 so as to allow any analyte-probe complex to pass through the lateral flow membrane contained in the Test Device. Capture probes and complementary immobilized capture moieties bind or hybridize to each other in predetermined lines or spots on the lateral flow membrane 803 or 804, whereby detection probes (via conjugate labels contained thereon) will provide a detectable signal which can subsequently be read to determine which analytes were present in the sample processed.

In one embodiment, Test Devices with samples processed thereon, can be set aside for time periods of about 1, 2, 3, 4, 5, 6 or 8 hours before reading the results, and yet provide results as accurately as if read in 15 or 20 minutes after processing. Thus, the signals produced are stable for long periods of time so that reading the results may occur at a significantly later time after the tests are actually performed. This is a great improvement for point-of-care diagnostics, where in the field conditions often present limited resources in manpower and time, and where the test setting can be in remote regions that are not easily or quickly accessed.

Binding Reagents.

One aspect of the invention is directed to binding reagents disposed in the SCD. For example, in some immunoassays, an antibody pair is utilized, where each member of the pair can specifically bind the same target analyte, wherein one antibody is a capture antibody and the other is a detection antibody. A capture antibody is linked, directly or indirectly, to a capture moiety which is "captured" by a cognate immobilized capture moiety disposed on a solid support (e.g., nitrocellulose membrane). Furthermore, the detection antibody (i.e., detection probe) is linked to a detectable label. The detection antibody is preferably labeled by conjugation to a physically detectable label, and upon contacting with the sample containing the target analyte forms a complex. The antibody-analyte complex can then be immobilized on a solid support via the capture moiety. The resulting complex immobilized on the solid support, is detectable by virtue of the label.

In one embodiment, the SCD reagent solution or solid substrate comprises a plurality of different detection probes, each detection probe capable of binding to a different target and each detection probe being labeled with or enabling the formation of a detection signal so that the presence of each target is indicated by the formation of a signal at the test zone for that target (i.e., in the Test Device); wherein the target for at least two of the capture moieties is an infectious agent or a disease causing micro-organism or a marker indicating the existence of a disease, disorder, or condition of the host from which the sample solution was derived, and wherein at least two of the capture moieties are capable of binding to different components or markers of the same infectious agent or disease causing microorganism, or to different markers for the same disease, disorder, or condition not caused by an infectious agent or disease causing microorganism, as targets for those capture moieties. Furthermore, the SCD will also comprise a plurality of different capture probes, each of which is paired up with a detection probe, where the pairing is defined by the capability to bind a particular target analyte.

As used herein, the term "specifically binds" refers to the binding specificity of a specific binding pair. "Specific binding pair member" refers to a member of a specific binding pair ("sbp"), which means two different molecules wherein one of the molecules specifically binds with the second molecule through chemical or physical means. For example, a pair of pRNAs or an aptamer/target antigen pair, or streptavidin-biotin provide exemplary specific binding pair members or sbp. The two molecules are related in the sense that their binding with each other is such that they are capable of distinguishing their binding partner from other assay constituents having similar characteristics. The members of the specific binding pair are referred to as ligand and receptor (antiligand), sbp member and sbp partner, and the like. A molecule may also be a sbp member for an aggregation of molecules; for example an antibody raised against an immune complex of a second antibody and its corresponding antigen may be considered to be an sbp member for the immune complex.

In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence or chemical moiety (such as digoxin anti-digoxin) and an antibody specific for the sequence, chemical moiety or the entire protein, polymeric acids and bases, dyes and protein binders, peptides and specific protein binders (e.g., ribonuclease, S-peptide and ribonuclease S-protein), metals and their chelators, and the like. Furthermore, specific binding pairs can include members that are analogs of the original specific binding member, for example an analyte-analog or a specific binding member made by recombinant techniques or molecular engineering.

An sbp member is analogous to another sbp member if they are both capable of binding to another identical complementary sbp member. Such an sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte. If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other specific binding members. Other examples of binding pairs that can be incorporated into the detection molecules are disclosed in U.S. Pat. Nos. 6,946,546, 6,967,250, 6,984,491, 7,022,492, 7,026,120, 7,022,529, 7,026,135, 7,033,781, 7,052,854, 7,052,916 and 7,056,679.

"Antibody" refers to a polypeptide substantially encoded by an immunoglobulin gene or immunoglobulin genes, or fragments thereof, and includes any immunoglobulin, including monoclonal antibodies, polyclonal antibodies, multispecific or bispecific antibodies, that bind to a specific antigen. A complete antibody comprises two heavy chains and two light chains. Each heavy chain consists of a variable region and a first, second, and third constant region, while each light chain consists of a variable region and a constant region. The antibody has a "Y" shape, with the stem of the Y consisting of the second and third constant regions of two heavy chains bound together via disulfide bonding. Each arm of the Y consists of the variable region and first constant region of a single heavy chain bound to the variable and constant regions of a single light chain. The variable regions of the light and heavy chains are responsible for antigen binding. The variable region in both chains generally contains three highly variable loops called the complementarity determining regions (CDRs) (light (L) chain CDRs including LCDR1, LCDR2, and LCDR3, heavy (H) chain CDRs including HCDR1, HCDR2, HCDR3) (as defined by Kabat, et al., Sequences of Proteins of Immunological Interest, Fifth Edition (1991), vols. 1-3, NIH Publication 91-3242, Bethesda Md.). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes and subclasses include IgG, IgG1, IgG2, IgG3, IgG4, IgM, IgA, IgA1, or IgA2, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods. The term "antibody" as used herein Antibodies are assigned to classes based on the amino acid sequence of the constant region of their heavy chain. The major classes of antibodies are IgA, IgD, IgE, IgG, and IgM, with several of these classes divided into subclasses such as.

In addition to an intact immunoglobulin, the term "antibody" as used herein further refers to an immunoglobulin fragment thereof (i.e., at least one immunologically active portion of an immunoglobulin molecule), such as a Fab, Fab', F(ab')$_2$, Fv fragment, a single-chain antibody molecule, a multispecific antibody formed from any fragment of an immunoglobulin molecule comprising one or more CDRs. In addition, an antibody as used herein may comprise one or more CDRs from a particular human immunoglobulin grafted to a framework region from one or more different human immunoglobulins.

"Fab" with regards to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

F(ab')$_2$ refers to a dimer of Fab'.

"Fc" with regards to an antibody refers to that portion of the antibody consisting of the second and third constant regions of a first heavy chain bound to the second and third constant regions of a second heavy chain via disulfide bonding. The Fc portion of the antibody is responsible for various effector functions but does not function in antigen binding.

"Fv" with regards to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Houston 1988).

"Single-chain Fv-Fc antibody" or "scFv-Fc" refers to an engineered antibody consisting of a scFv connected to the Fc region of an antibody.

The term "epitope" as used herein refers to the group of atoms and/or amino acids on an antigen molecule to which an antibody binds.

The term "monoclonal antibody" as used herein refers to an antibody or a fragment thereof obtained from a population of substantially homogeneous antibodies, i.e., the individual antibodies comprising the population are identical except for possible naturally occurring mutations that may be present in minor amounts. Monoclonal antibodies are highly specific, being directed against a single epitope on the antigen. Monoclonal antibodies are in contrast to polyclonal antibodies which typically include different antibodies directed against different epitopes on the antigens. Although monoclonal antibodies are traditionally derived from hybridomas, the monoclonal antibodies of the present invention are not limited by their production method. For example, the monoclonal antibodies of the present invention may be made by the hybridoma method first described by Kohler et al., Nature, 256:495 (1975), or may be made by recombinant DNA methods (see, e.g., U.S. Pat. No. 4,816,567).

The term "chimeric antibody" as used herein refers to an antibody in which a portion of the heavy and/or light chain is identical with or homologous to corresponding sequences in antibodies derived from a particular species or belonging to a particular antibody class or subclass, while the remainder of the heavy and/or light chain is identical with or homologous to corresponding sequences in antibodies derived from another species or belonging to another antibody class or subclass, as well as fragments of such an antibody, so long as such fragments exhibit the desired antigen-binding activity (U.S. Pat. No. 4,816,567 to Cabilly et al.; Morrison et al., Proc. Natl. Acad, Sci, USA, 81:6851 6855 1984)).

The term "humanized antibody" used herein refers to an antibody or fragments thereof which are human immunoglobulins (recipient antibody) in which residues from part or all of a CDR of the recipient are replaced by residues from a CDR of a non-human species (donor antibody) such as mouse, rat or rabbit having the desired specificity, affinity, and capacity. In some instances, FR residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin Fc region, typically that of a human immunoglobulin. For further details, see Jones et al., Nature, 321:522 525 (1986); Reichmann et al., Nature, 332:323 329 (1988); Presta, Curr. Op. Struct, Biol., 2:593 596 (1992); and Clark, Immunol. Today 21: 397 402 (2000).

The present invention provides anti-H5 monoclonal antibodies that are produced by mice hybridoma cell strains 8H5, 3C8, 10F7, 4D1, 3G4 and 2F2, These monoclonal antibodies are named after the hybridoma cell strains that produce them. Thus the anti-H5 monoclonal antibodies that are produced by mice hybridoma cell strains 8H5, 3C8, 10F7, 4D1, 3G4, and 2F2, respectively, are named monoclonal antibodies 8H5, 3C8, 10F7, 4D1, 3G4, and 2F2, respectively. Monoclonal antibodies 8H5, 3C8, 10F7, 4D1, 3G4, and 2F2 specifically bind to the hemagglutinin of subtype H5 avian influenza virus. The mice hybridoma cell strains 8H5, 3C8, 10F7, 4D1, 3G4, and 2F2 were deposited in China Center for Typical Culture Collection (CCTCC, Wuhan University, Wuhan, China) on Jan. 17, 2006 with deposit numbers of CCTCC-C200607 (hybridoma cell strain 8H5), CCTCC-C200605 (hybridoma cell strain 3C8), CCTCC-C200608 hybridoma cell strain 10F7), CCTCC-C200606 (hybridoma cell strain 4D1), CCTCC-C200604 (hybridoma cell strain 3G4) and CCTCC-C200424 (hybridoma cell strain 2F2).

In various embodiment, monoclonal antibodies are provided that block the binding of monoclonal antibodies 8H5, 3C8, 10F7, 4D1, 3G4, or 2F2 to the hemagglutinin of subtype H5 avian influenza virus. Such blocking monoclonal antibodies may bind to the same epitopes on the hemagglutinin that are recognized by monoclonal antibodies 8H5, 3C6, 10F7, 4D1, 3G4, or 2F2. Alternatively, those blocking monoclonal antibodies may bind to epitopes that overlap sterically with the epitopes recognized by monoclonal antibodies 8H5, 3C8, 10F7, 4D1, 3G4, or 2F2. These blocking monoclonal antibodies can reduce the binding of monoclonal antibodies 8H5, 3C8, 10F7, 4D1, 3G4, or 2F2 to the hemagglutinin of subtype H5 avian influenza virus by at least about 50%. Alternatively, they may reduce binding by at least about 60%, preferably at least about 70%, more preferably at least about 75%, more preferably at least about 80%, more preferably at least about 85%, even more preferably at least about 90%, even more preferably at least about 95%, most preferably at least about 99%.

The ability of a test monoclonal antibody to reduce the binding of a known monoclonal antibody to the H5 hemagglutinin may be measured by a routine competition assay such as that described in *Antibodies: A Laboratory Manual*, Cold Spring Harbor Laboratory, Ed Harlow and David Lane (1988). For example, such an assay could be performed by pre-coating a microtiter plate with antigens, incubating the pre-coated plates with serial dilutions of the unlabeled test antibodies admixed with a selected concentration of the labeled known antibodies, washing the incubation mixture, and detecting and measuring the amount of the known antibodies bound to the plates at the various dilutions of the test antibodies. The stronger the test antibodies compete with the known antibodies for binding to the antigens, the more the binding of the known antibodies to the antigens would be reduced. Usually, the antigens are pre-coated on a 96-well plate, and the ability of unlabeled antibodies to block the binding of labeled antibodies is measured using radioactive or enzyme labels.

Monoclonal antibodies may be generated by the hybridoma method first described by Kohler et al., Nature, 256: 495 (1975). In the hybridoma method, a mouse or other appropriate host animal is immunized by one or more injections of an immunizing agent and, if desired, an adjuvant. Typically, the immunizing agent and/or adjuvant will be injected in the host animal by multiple subcutaneous or intraperitoneal injections. It may be useful to conjugate the immunizing agent to a protein known to be immunogenic in the host animal being immunized, such as serum albumin, or soybean trypsin inhibitor. Examples of adjuvants which may be employed include Freund's complete adjuvant and MPL-TDM. After immunization, the host animal makes lymphocytes that produce or are capable of producing antibodies that will specifically bind to the antigen used for immunization. Alternatively, lymphocytes may be immunized in vitro. Desired lymphocytes are collected and fused with myeloma cells using a suitable fusing agent, such as polyethylene glycol, to form a hybridoma cell (Goding, *Monoclonal Antibodies: Principles and Practice*, pp. 59 103, Academic Press, 1996).

The hybridoma cells thus prepared are seeded and growl in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., *Moocloonal Antibody Production Techniques and Applications*, pp. 51-63, Marcel Dekker, Inc., New York, 1987).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the cells may be subcloned by limiting dilution procedures and grown by standard methods (Goding, Monoclonal Antibodies: Principles and Practice, pp. 59-103, Academic Press, 1996). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies of the invention may also be made by conventional genetic engineering methods. DNA molecules encoding the heavy and light chains of the monoclonal antibodies may be isolated from the hybridoma cells, for example through PCR using oligonucleotide probes that are capable of binding specifically to genes encoding the heavy and light chains of the monoclonal antibodies. Then the DNA molecules are inserted into expression vectors. The expression vectors are transfected into host cells such as E. coli cells, simian COS cells, Chinese hamster ovary (CHO) cells, or myeloma cells that do not otherwise produce immunoglobulin protein. The host cells are cultured under conditions suitable for the expression of the antibodies.

The antibodies of the invention can bind to the H5 hemagglutinin with high specificity and affinity. The antibodies shall have low cross-reactivity with other subtypes of hemagglutinin, preferably no cross-reactivity with other subtypes of hemagglutinins. In one aspect, the invention provides antibodies that bind to H5 hemagglutinin with a $K_D$ value of less than $1 \times 10^{-5}$M. Preferably, the $K_D$ value is less than $1 \times 10^{-6}$M. More preferably, the $K_D$ value is less than $1 \times 10^{-7}$M. Most preferably, the $K_D$ value is less than $1 \times 10^{-8}$ M.

The antibodies of the invention may contain the conventional "Y" shape structure comprised of two heavy chains and two light chains. In addition, the antibodies may also be the Fab fragment, the Fab' fragment, the F(ab)$_2$ fragment or the Fv fragment, or another partial piece of the conventional "Y" shaped structure that maintains binding affinity to the hemagglutinin. The binding affinity of the fragments to hemagglutinin may be higher or lower than that of the conventional "Y" shaped antibodies.

The antibody fragments may be generated via proteolytic digestion of intact antibodies (see, e.g., Morimoto et al., J. Biochem. Biophys. Methods, 24:107-117, (1992) and Brennan et al., Science, 229:81 (1985)). Additionally, these fragments can also be produced directly by recombinant host cells (reviewed in Hudson, Curr. Opin. Immunol., 11: 548-557 (1999); Little et al., Immunol. Today, 21: 364-370 (2000)). For example, Fab' fragments can be directly recovered from E. coli and chemically coupled to form F(ab')$_2$ fragments (Carter et al., Bio/Technology, 10: 163 167 (1992)). In another embodiment, the F(ab')$_2$ is formed using the leucine zipper GCN4 to promote assembly of the F(ab')$_2$ molecule.

According to another approach, Fv, Fab or F(ab')$_2$ fragments can be isolated directly from recombinant host cell culture. Other techniques for the production of antibody fragments will be apparent to a person with ordinary skill in the art.

The present invention provides isolated nucleic acid molecules encoding antibodies or fragments thereof that specifically bind to H5 hemagglutinin. Nucleic acid molecules encoding the antibodies can be isolated from hybridoma cells. The nucleic acid sequences of the molecules can be determined using routine techniques known to a person with ordinary skill in the art. Nucleic acid molecules of the invention can also be prepared using conventional genetic engineering techniques as well as chemical synthesis. In one aspect, the present invention provides an isolated nucleic acid molecule encoding the variable region of the heavy chain of an anti-H5 (HA) antibody or a portion of the nucleic acid molecule. In another aspect, the present invention provides an isolated nucleic acid molecule encoding the variable region of the light chain of an anti-H5 (HA) antibody or a portion of the nucleic acid molecule. In another aspect, the present invention provides an isolated nucleic acid molecule encoding the CDRs of the antibody heavy chain or light chain variable regions.

In one aspect, the present invention provides isolated nucleic acid molecules encoding the variable regions of the heavy chain and light chain of monoclonal antibodies 8H5, 3C8, 10F7, 4D1, 3G4, and 2F2. The nucleic acid sequences encoding the heavy chain variable regions of monoclonal antibodies 8H5, 3C8, 10F7, 4D1, 3G4, and 2F2 are set forth in SEQ ID NO: 1, SEQ ID NO: 5, SEQ ID NO: 9, SEQ ID NO: 16, SEQ ID NO:20 and SEQ ID NO: 22, respectively. The nucleic acid sequences encoding the light chain variable regions of monoclonal antibodies 8H5, 3C8, 10F7, 4D1, and 2F2 are set forth in SEQ ID NO: 3, SEQ ID NO: 7, SEQ ID NO: 11, SEQ ID NO: 18, SEQ ID NO:24, respectively. The present invention also includes degenerative analogs of the nucleic acid molecules encoding the variable regions of the heavy chain and light chain of monoclonal antibodies 8H5, 3C8, 10F7, 4D1, 3G4 and 2F2.

In another aspect, the present invention provides isolated nucleic acid variants that share sequence identity with the nucleic acid sequences of SEQ ID NO: 1, SEQ ID NO: 3, SEQ ID NO: 5, SEQ ID NO: 7, SEQ ID NO: 9, SEQ ID NO: 11, SEQ ID NO: 16, SEQ ID NO:18, SEQ ID NO:20, SEQ ID NO:22 or SEQ ID NO:24. In one embodiment, the nucleic acid variants share at least 70% sequence identity, preferably at least 75% sequence identity, more preferably at least 80% sequence identity, more preferably at least 85% sequence identity, more preferably at least 90% sequence identity, most preferably at least 95% sequence identity, to the sequences of SEQ ID NO: 1, SEQ ID NO: 3, SEQ ID NO: 5, SEQ ID NO: 7, SEQ ID NO: 9, SEQ ID NO: 11, SEQ ID NO: 16, SEQ ID NO: 18, SEQ ID NO:20, SEQ ID NO:22 or SEQ ID NO:24.

The present invention also provides isolated nucleic acid molecules encoding antibody fragments that are still capable of specifically binding to subtype H5 of avian influenza virus.

The present invention further provides isolated nucleic acid molecules encoding an antibody heavy chain variable region comprising the amino acid sequence set forth in SEQ ID NOs: 26-28, SEQ ID NOs: 32-34, SEQ ID NOs: 38-40, SEQ ID NOs: 44-46; SEQ ID NOs: 50-52, and SEQ ID NOs: 53-55. The present invention provides isolated nucleic acid molecules encoding an antibody light chain variable region comprising the amino acid sequence set forth in SEQ ID NOs: 29-31, SEQ ID NOs: 35-37, SEQ ID NOs: 41-43, SEQ ID NOs: 47-49, and SEQ ID NOs: 56-58.

The present invention provides recombinant expressing vectors comprising the isolated nucleic acid molecules of the invention. It also provides host cells transformed with die nucleic acid molecules. Furthermore, the present invention provides a method of producing antibodies of the invention comprising culturing the host cells under conditions wherein the nucleic acid molecules are expressed to produce the antibodies and isolating the antibodies from the host cells.

Antibody Polypeptide Sequences

The amino acid sequences of the variable regions of the heavy chain and light chain of monoclonal antibodies 8H5, 3C8, 10F7, 4D1, 3G4 and 2F2 have been deduced from their respective nucleic acid sequences. The amino acid sequences of the heavy chain variable regions of monoclonal antibodies 8H5, 3C8, 10F7, 4D1, 3G4 and 2F2 are set forth in SEQ ID NO:2, SEQ ID NO:6, SEQ ID NO: 10, SEQ ID NO:17, SEQ ID NO:21, and SEQ ID NO:23, respectively. The amino acid sequences of the light chain variable regions of monoclonal antibodies 8H5, 3C8, 10F7, 4D1, and 2F2 are set forth in SEQ ID NO:4, SEQ ID NO:8, SEQ ID NO:12, SEQ ID NO:19, and SEQ ID NO:25. In one aspect, the present invention provides anti-H5 antibodies comprising a heavy chain variable region comprising the amino acid sequences as set forth in SEQ ID NO:2, SEQ ID NO:6, SEQ ID NO: 10, SEQ ID NO: 17, SEQ ID NO:21, and SEQ ID NO: 23. In another aspect, the present invention provides anti-H5 antibodies comprising a light chain variable region comprising the amino acid sequences as set forth in SEQ ID NO:4, SEQ ID NO:8, SEQ ID NO:12, SEQ ID NO:19, and SEQ ID NO:25.

In another aspect, the present invention provides an antibody heavy chain comprising a variable region having at least 70% sequence identity, preferably at least 75% sequence identity, more preferably at least 80% sequence identity, more preferably at least 85% sequence identity, more preferably at least 90% sequence identity, most preferably at least 95% sequence identity to the amino acid sequences set forth in SEQ ID NO:2, SEQ ID NO:6, SEQ ID NO: 10, SEQ ID NO: 17, SEQ ID NO:21, and SEQ ID NO:23.

In another aspect, the present invention provides an antibody light chain comprising a variable region having at least 70% sequence identity, preferably at least 75% sequence identity, more preferably at least 80% sequence identity, more preferably at least 85% sequence identity, more preferably at least 90% sequence identity, most preferably at least 95% sequence identity to the amino acid sequences set forth in SEQ ID NO:4, SEQ ID NO:8, SEQ ID NO: 12, SEQ ID NO: 19, and SEQ ID NO:25.

The amino acid sequences of the CDRs of the variable regions of the heavy chain and light chain of monoclonal antibodies 8H5, 3C8, 10F7, 4D1, 3G4, and 2F2 have also been determined as follows:

The amino acid sequences of CDR1, CDR2 and CDR3 of the heavy chain of monoclonal antibody 8H5 are set forth in SEQ ID Nos:26-28, respectively. The amino acid sequences of CDR1, CDR2 and CDR3 of the light chain of monoclonal antibody 8H5 are set forth in SEQ ID Nos: 29-31, respectively.

The amino acid sequences of CDR1, CDR2 and CDR3 of the heavy chain of monoclonal antibody 3C8 are set forth in SEQ ID Nos:32-34, respectively. The amino acid sequences of CDR1, CDR2 and CDR3 of the light chain of monoclonal antibody 3C8 are set forth in SEQ ID Nos: 35-37, respectively.

The amino acid sequences of CDR1, CDR2 and CDR3 of the heavy chain of monoclonal antibody 10F7 are set forth in SEQ ID Nos:38-40, respectively. The amino acid sequences of CDR1, CDR2 and CDR3 of the light chain of monoclonal antibody 10F7 are set forth in SEQ ID Nos:41-43, respectively.

The amino acid sequences of CDR1, CDR2 and CDR3 of the heavy chain of monoclonal antibody 4D1 are set forth in SEQ ID Nos:44-46, respectively. The amino acid sequences of CDR1, CDR2 and CDR3 of the light chain of monoclonal antibody 4D1 are set forth in SEQ ID Nos: 47-49, respectively.

The amino acid sequences of CDR1, CDR2 and CDR3 of the heavy chain of monoclonal antibody 3G4 are set forth in SEQ ID Nos:50-52, respectively.

The amino acid sequences of CDR1, CDR2 and CDR3 of the heavy chain of monoclonal antibody 2F2 are set forth in SEQ ID Nos:53-55, respectively. The amino acid sequences of CDR1, CDR2 and CDR3 of the light chain of monoclonal antibody 2F2 are set forth in SEQ ID Nos: 56-58, respectively.

TABLE 1

Six strains of monoclonal antibody CDRs amino acid sequence.

| Monoclonal antibody strains | Antibody heavy chain CDRs amino acid sequence | | | Antibody light chain CDRs amino acid sequence | | |
|---|---|---|---|---|---|---|
| | CDR1 | CDR2 | CDR3 | CDR1 | CDR2 | CDR3 |
| 8H5 | GYTFSNYW (SEQ ID NO: 26) | ILPGSDRT (SEQ ID NO: 27) | ANRYDGYYFGLDY (SEQ ID NO: 28) | SSVNF (SEQ ID NO: 29) | YSS (SEQ ID NO: 30) | QHFTSSPYT (SEQ ID NO: 31) |
| 3C8 | GYSFTNYG (SEQ ID NO: 32) | INTHTGEP (SEQ ID NO: 33) | ARWNRDAMDY (SEQ ID NO: 34) | ESVDSSDNSL (SEQ ID NO: 35) | RAS (SEQ ID NO: 36) | QQSIGDPPYT (SEQ ID NO: 37) |
| 10F7 | GYTFTSYW (SEQ ID NO: 38) | IDPSDSYT (SEQ ID NO: 39) | ARGGTGDFHYAMDY (SEQ ID NO: 40) | QGISSN (SEQ ID NO: 41) | HGT (SEQ ID NO: 42) | QYVQFPYT (SEQ ID NO: 43) |
| 4D1 | GYTFTSYW (SEQ ID NO: 44) | IDPSDSFT (SEQ ID NO: 45) | ARGGPGDFRYAMDY (SEQ ID NO: 46) | QGISSN (SEQ ID NO: 47) | HGT (SEQ ID NO: 48) | VQYVQFPYT (SEQ ID NO: 49) |
| 3G4 | GYTFTDYA (SEQ ID NO: 50) | INTDYGDT (SEQ ID NO: 51) | ARSDYDYYFCGMDY (SEQ ID NO: 52) | | | |
| 2F2 | GFSLTGYG (SEQ ID NO: 53) | IWAEGRT (SEQ ID NO: 54) | AREVITTEAWYFDV (SEQ ID NO: 55) | QSISDY (SEQ ID NO: 56) | YAS (SEQ ID NO: 57) | QNGHTFPLT (SEQ ID NO: 58) |

In another aspect, the present invention provides an anti-H5 monoclonal antibody heavy chain or a fragment thereof, comprising the following CDRs: (i) one or more CDRs selected from SEQ ID NOs: 26-28; (ii) one or more CDRs selected from SEQ ID NOs: 32-34; (iii) one or more CDRs selected from SEQ ID NOs: 38-40; (iv) one or more CDRs selected from SEQ ID NOs: 44-56; (v) one or more CDRs selected from SEQ ID NOs: 50-52; or (vi) one or more CDRs selected from SEQ ID NOs: 53-55. In one embodiment, the anti-H5 monoclonal antibody heavy chain or a fragment thereof comprises three CDRs having the amino acid sequences set forth in SEQ ID NOs: 26-28, respectively. In another embodiment, the anti-H5 monoclonal antibody heavy chain or a fragment thereof comprises three CDRs having the amino acid sequences set forth in SEQ ID NOs: 32-34, respectively. In another embodiment, the anti-H5 monoclonal antibody heavy chain or a fragment thereof comprises three CDRs having the amino acid sequences set forth in SEQ ID NOs: 38-40. In another embodiment, the anti-H5 monoclonal antibody heavy chain or a fragment thereof comprises three CDRs having the amino acid sequences set forth in SEQ ID NOs: 44-46. In another embodiment, the anti-H5 monoclonal antibody heavy chain or a fragment thereof comprises three CDRs having the amino acid sequences set forth in SEQ ID NOs: 50-52. In another embodiment, the anti-H5 monoclonal antibody heavy chain or a fragment thereof comprises three CDRs having the amino acid sequences set forth in SEQ ID NOs: 53-55.

In another aspect, the CDRs contained in the anti-H5 monoclonal antibody heavy chains or fragments thereof of the present invention may include one or more amino acid substitution, addition and/or deletion from the amino acid sequences set forth in SEQ ID NOs: 26-28, 32-32-34, -38-40, 44-46, 50-52, and 53-55. Preferably, the amino acid substitution, addition and/or deletion occur at no more than three amino acid positions. More preferably, the amino acid substitution, addition and or deletion occur at no more than two amino acid positions. Most preferably, the amino acid substitution, addition, and or deletion occur at no more than one amino acid position.

In another aspect, the present invention provides an anti-H 5monoclonal antibody light chain or a fragment thereof, comprising the following CDRs: (i) one or more CDRs selected from SEQ ID NOs: 29-31; (ii) one or more CDRs selected from SEQ ID NOs: 35-37; (iii) one or more CDRs selected from SEQ ID NOs: 41-43; (iv) one or more CDRs selected from SEQ ID NOs: 47-49; (v) one or more CDRs selected from SEQ ID NOs: 56-58. In one embodiment, the anti-H5 monoclonal antibody light chain or a fragment thereof comprises three CDRs having the amino acid sequences set forth in SEQ ID NOs: 29-31, respectively. In another embodiment, the anti-H5 monoclonal antibody light chain or a fragment thereof comprises three CDRs having the amino acid sequences set forth in SEQ ID NOs: 35-37, respectively. In another embodiment, the anti-H5 monoclonal antibody light chain or a fragment thereof comprises three CDRs having the amino acid sequences set forth in SEQ ID NOs: 41-43. In another embodiment, the anti-H5 monoclonal antibody light chain or a fragment thereof comprises three CDRs having the amino acid sequences set forth in SEQ ID NOs: 47-49. In another embodiment, the anti-H5 monoclonal antibody light chain or a fragment thereof comprises three CDRs having the amino acid sequences set forth in SEQ ID NOs: 56-58.

In another aspect, the CDRs contained in the anti-H5 monoclonal antibody light chains or fragments thereof of the present invention may include one or more amino acid substitution, addition and/or deletion from the amino acid sequences set forth in SEQ ID NOs: 29-31, 35-37, 41-43, 47-49, and 56-58. Preferably, the amino acid substitution, addition and/or deletion occur at no more than three amino acid positions. More preferably, the amino acid substitution, addition and/or deletion occur at no more than two amino acid positions. Most preferably, the amino acid substitution, addition and/or deletion occur at no more than one amino acid position.

TABLE 2

The Amino Acid Sequences of the 7aa peptides that bind to 8H5 mAb or 3C8 mAb.

| Monoclonal Antibody | 7peptide sequences | Sequence No. |
|---|---|---|
| 8H5 | H G M L P V Y | SEQ ID No: 59 |
|  | P P S N Y G R | SEQ ID No: 60 |
|  | P P S N F G K | SEQ ID No: 61 |
|  | G D P W F T S | SEQ ID No: 62 |
|  | N S G P W L T | SEQ ID No: 63 |
| 3C8 | W P P L S K K | SEQ ID No: 64 |
|  | N T F R T P I | SEQ ID No: 65 |
|  | N T F R D P N | SEQ ID No: 66 |
|  | N P I W T K L | SEQ ID No: 67 |

The variants generated by amino acid substitution, addition and/or deletion in the variable regions of the above described antibodies or the above described CDRs maintain the ability of specifically binding to subtype H5 of avian influenza virus. The present inventions also include antigen-binding fragments of such variants.

Monoclonal antibody variants of the invention may be made by conventional genetic engineering methods. Nucleic acid mutations may be introduced into the DNA molecules using methods known to a person with ordinary skill in the art. Alternately, the nucleic acid molecules encoding the heavy and light chain variants may be made by chemical synthesis.

In another aspect, the screening method of the invention comprises the steps of (i) culturing a peptide display library under conditions suitable for peptide expression; (ii) contacting the culture solution with monoclonal antibodies of the invention; (iii) selecting the phage clones that specifically bind to said monoclonal antibodies. The monoclonal antibodies used for the screening may include without limitation the monoclonal antibodies 8H5, 3C8, 10F7, 4D1 and 3G4. Example 12 included herein describes in detail an assay that successfully screened short peptides that bind to the monoclonal antibodies of the invention using a peptide phage display libraries.

TABLE 3

The sequences of the 12aa peptides that bind to 8H5 mAb.

| Peptide section No. | Amino Acid Sequence | Base Sequence |
|---|---|---|
| 121 | MEPVKKYPTRSP (SEQ ID NO: 68) | ATGGAGCCGGTGAAGAAGTATCCGACGCGTTCTCCT (SEQ ID NO: 69) |

TABLE 3-continued

The sequences of the 12aa peptides that bind to 8H5 mAb.

| Peptide section No. | Amino Acid Sequence | Base Sequence |
|---|---|---|
| 122 | ETQLTTAGLRLL (SEQ ID NO: 70) | GAGACTCAGCTGACTACGGCGGGTCTTCGGCTGCTT (SEQ ID NO: 71) |
| 123 | ETPLTETALKWH (SEQ ID NO: 72) | GAGACGCCTCTTACGGAGACGGCTTTGAAGTGGCAT (SEQ ID NO: 73) |
| 124 | QTPLTMAALELF (SEQ ID NO: 74) | CAGACGCCGCTGACTATGGCTGCTCTTGAGCTTTTT (SEQ ID NO: 75) |
| 125 | DTPLTTAALRLV (SEQ ID NO: 76) | GATACTCCGCTGACGACGGCGGCTCTTCGGCTGGTT (SEQ ID NO: 77) |
| 126 | TPLTLWALSGLR (SEQ ID NO: 78) | ACGCCGCTTACGCTTTGGGCTCTTTCTGGGCTGAGG (SEQ ID NO: 79) |
| 128 | QTPLTETALKWH (SEQ ID NO: 80) | CAGACGCCTCTTACGGAGACGGCTTTGAAGTGGCAT (SEQ ID NO: 81) |
| 129 | QTPLTMAALELL (SEQ ID NO: 82) | CAGACGCCTCTGACTATGGCGGCTCTTGAGCTTCTT (SEQ ID NO: 83) |
| 130 | HLQDGSPPSSPH (SEQ ID NO: 84) | CAGACGCCTCTGACTATGGCGGCTCTTGAGCTTCTT (SEQ ID NO: 85) |
| 131 | GHVTTLSLLSLR (SEQ ID NO: 86) | GGGCATGTGACGACTCTTTCTCTTCTGTCGCTGCGG (SEQ ID NO: 87) |
| 132 | FPNFDWPLSPWT (SEQ ID NO: 88) | TTTCCGAATTTTGATTGGCCTCTGTCTCCGTGGACG (SEQ ID NO: 89) |
| 133 | ETPLTEPAFKRH (SEQ ID NO: 90) | GAGACGCCTCTTACGGAGCCGGCTTTTAAGCGGCAT (SEQ ID NO: 91) |

As used herein the term "Analyte" refers to the compound or composition to be detected or measured and which has at least one epitope or binding site. The analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42, the disclosure of which is incorporated herein by reference. Further descriptions and listings of representative analytes are found in U.S. Pat. Nos. 4,299,916; 4,275,149; and 4,806,311, all incorporated herein by reference. In some embodiments, the SCD or Test Device are configured to detect a plurality of different analytes (e.g., FIG. 26).

Labeled Reagents

"Labeled reagent" refers to a substance comprising a detectable label attached with a specific binding member (e.g., detection probe). The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the Test Device at a site upstream from the capture zone, it can be combined with the fluid sample to form a fluid solution, it can be added to the test device separately from the test sample, or it can be predeposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates, chromogens, catalysts, fluorescent or fluorescent like compounds and/or particles, magnetic compounds and/or particles chemiluminescent compounds and or particles, and radioactive labels. Other suitable labels include particulate labels such as colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing components at the detection sites.

Additional labels that can be utilized in the practice of the invention include, chromophores, electrochemical moieties, enzymes, radioactive moieties, phosphorescent groups, fluorescent moieties, chemiluminescent moieties, or quantum dots, or more particularly, radiolabels, fluorophore-labels, quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, $I^2$-galactosidase, alkaline phosphatase, β-galactosidase, or acetylcholinesterase and hapten conjugates such as digoxigenin or dinitrophenyl, or members of a binding pair that are capable of forming complexes such as streptavidin/biotin, avidin/biotin or an antigen antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, a luminescent material such as luminol; light scattering or plasmon resonant materials such as gold or silver particles or quantum dots; or radioactive material include $^{14}C$, $^{123}I$, $^{124}I$, $^{125}I$, $^{131}I$, Tc99m, $^{35}S$ or $^{3}H$, or spherical shells, and probes labeled with any other signal generating label known to those of skill in the art. For example, detectable molecules include but are not limited to fluorophores as well as others known in the art as described, for example, in Principles of Fluorescence Spectroscopy, Joseph R. Lakowicz (Editor), Plenum Pub Corp, 2nd edition (July 1999) and the $6^{th}$ Edition of the Molecular Probes Handbook by Richard P. Hoagland.

A number of signal producing systems may be employed to achieve the objects of the invention. The signal producing system generates a signal that relates to the presence of an analyte (i.e., target molecule) in a sample. The signal producing system may also include all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. In some embodiments, the signal producing system provides a signal detectable by external means, by use of electromagnetic radiation, desirably by visual examination. Exemplary signal-producing systems are described in U.S. Pat. No. 5,508,178.

In some embodiments, nucleic acid molecules can be linked to the detection probe (e.g., antibody-linked oligonucleotides), whereby the nucleic acid functions as a label by utilizing nucleic acid labels. For example, a reagent solution or substrate comprised in a SCD can comprise detection reagents—plurality of detection and capture specific binding agents ("SBA")—comprising a plurality of oligonucleotides functioning to provide a detectable signal, whereby for a given subpopulation of SBAs (specific for a particular analyte), conjugated oligonucleotides are pre-stained with a different stain as compared to another subpopulation of antibodies (specific for a different analyte) are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red). Other detectable markers include chemiluminescent and chromogenic molecules, optical or electron density markers, etc.

As noted above in certain embodiments, labels comprise semiconductor nanocrystals such as quantum dots (i.e., Qdots), described in U.S. Pat. No. 6,207,392. Qdots are commercially available from Quantum Dot Corporation. The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof, as well as nanocrystals of Group III-V semiconductors such as GaAs, InGaAs, InP, and InAs and mixed compositions thereof. The use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

In some embodiments, a fluorescent energy acceptor is linked as a label to a detection probe (i.e., binding moiety conjugated with a detector molecule). In one embodiment the fluorescent energy acceptor may be formed as a result of a compound that reacts with singlet oxygen to form a fluorescent compound or a compound that can react with an auxiliary compound that is thereupon converted to a fluorescent compound. Such auxiliary compounds can be comprised in buffers contained in an SCD and/or Test Device. In other embodiments, the fluorescent energy acceptor may be incorporated as part of a compound that also includes the chemiluminescer. For example, the fluorescent energy acceptor may include a metal chelate of a rare earth metal such as, e.g., europium, samarium, tellurium and the like. These materials are particularly attractive because of their sharp band of luminescence. Furthermore, lanthanide labels, such as europium (III) provide for effective and prolonged signal emission and are resistant to photo bleaching, thereby allowing Test Devices containing processed/reacted sample to be set aside if necessary for a prolong period of time.

Long-lifetime fluorescent europium(III) chelate nanoparticles have been shown to be applicable as labels in various heterogeneous and homogeneous immunoassays. See, e.g., Huhtinen et al., Clin. Chem. 2004 October, 50(10): 1935-6. Assay performance can be improved when these intrinsically labeled nanoparticles are used in combination with time-resolved fluorescence detection. In heterogeneous assays, the dynamic range of assays at low concentrations can be extended. Furthermore, the kinetic characteristics of assays can be improved by use of detection antibody-coated high-specific-activity nanoparticle labels instead of conventionally labeled detection antibodies. In homogeneous assays, europium(III) nanoparticles have been shown to be efficient donors in fluorescence resonance energy transfer, enabling simple and rapid highthroughput screening. Heterogeneous and homogeneous nanoparticle-label-based assays can be run with various sample matrixes, e.g., serum, heparin plasma, and mucus.

In some embodiments, a label (e.g., fluorescent label) disclosed herein, is comprised as a nanoparticle label conjugated with biomolecules. In other words, a nanoparticle can be utilized with a detection or capture probe. For example, a europium(III)-labeled nanoparticle linked to monoclonal antibodies or strepavidin (SA) to detect a particular analyte in a sample can be utilized in practice of the present invention (e.g., nanoparticle-based immunoassay). The nanoparticles serve as a substrate to which are attached the specific binding agents to the analyze and either the detection (i.e., label) or capture moiety.

In various embodiments of the invention, the label utilized is a lanthanide metal. Lanthanides include but are not limited to europium, samarium, terbium or dysprosium. Non-specific background fluorescence has a decay time of only about 10 ns, so that such background dies away before the sample fluorescence is measured. Furthermore, Lanthanide-chelates have large Stokes' shifts. For example, the Stokes' shift for europium is almost 300 nm. This big difference between excitation and emission peaks means that the fluorescence measurement is made at a wavelength where the influence of background is minimal. In addition, the emission peak is very sharp which means that the detector can be set to very fine limits and that the emission signals from different lanthanide chelates can be easily distinguished from each other. Therefore, in one embodiment, one or more different lanthanides can be utilized in the same assay.

Hard Standards. In one embodiment, a fluorescence reader is configured to comprise an integrated or permanent standard ("hard standard"). The term "hard standard" as referred to herein means that the device for reading a test sample in methods of detecting/quantifying one or more analytes comprises an internal, integrated or permanent standard, against which samples labeled with the same label as that used in the hard standard are read. In one embodiment, the hard standard and the test label comprise a lanthanide (e.g., Europium III) FIG. 33.

In one embodiment, the reader is an LED, comprising a lamp emitting UV A (400 to 315 nm) part of the spectrum. Emission is in the visible part of the spectrum. Some exemplary or conventional LEDs or photodiodes are disclosed in U.S. Pat. Nos. 7,175,086, 7,135,342, and 7,106,442, the disclosure of each of which is incorporated herein in its entirety.

In another embodiment, a reader comprises at least two hard standards of different amounts (e.g., low and high concentration of label), thus providing a two point check of the reader. For example, two (2) lanthanide hard standards (e.g., Europium) are mounted permanently on the reader slides and may be read during the course of each test read. As such, the two hard standards can be utilized to determine the lower detection limit (i.e. in a analyte quantification assay or for determining lowest detection threshold in qualitative assays). Here, fluorescence is read and plotted as percentage of fluorescence (y axis) against concentration (x axis). The straight line between the two reads for each of the hard standards on such a plot allows measuring the intercept of noise (no label) to give a measurement for the lowest detection limit.

In some embodiments, a Test Device comprises a chamber (compartment or liquid sac) that contains wash or running buffer, which functions to remove unbound label, to reduce or eliminating background noise. In various embodiments, devices comprising a hard standard(s) provide accurate qualitative as well quantitative measurement of analyte(s) present in a sample and labeled with label that is the same as that used in the hard standard(s).

Figure 33A:
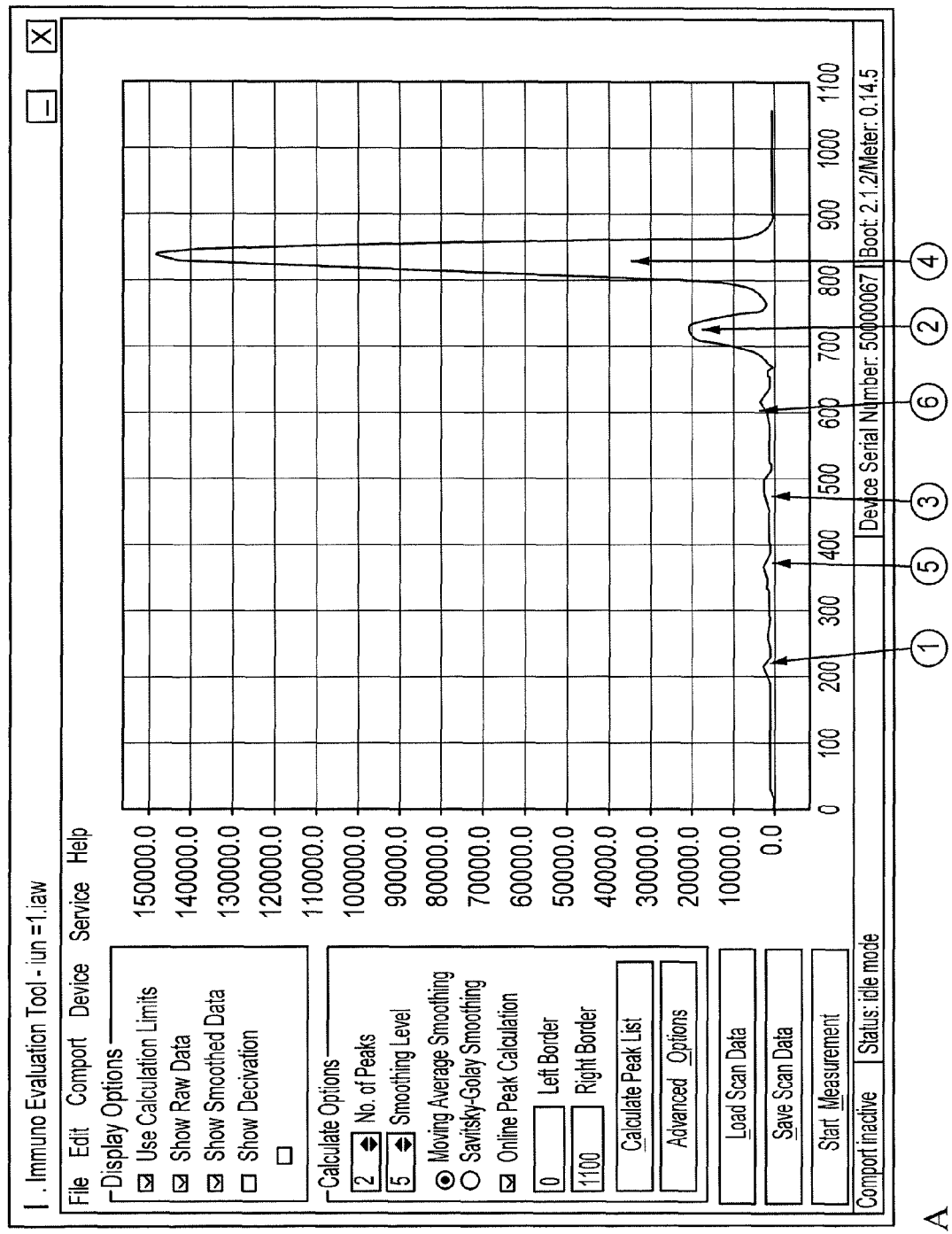
FIG. 33. Hard Standards; (A) graph of six different concentrations of Europium as read of an UV LED reader; (B) photo of the six hard standards; (C) graph for concentration #1; (D) graph for concentration of #5; (E) graph for concentration #3; (F) graph for concentration of #6; (G) graph for concentration of #2; (H) graph for concentration of #4.
Figure 33B:
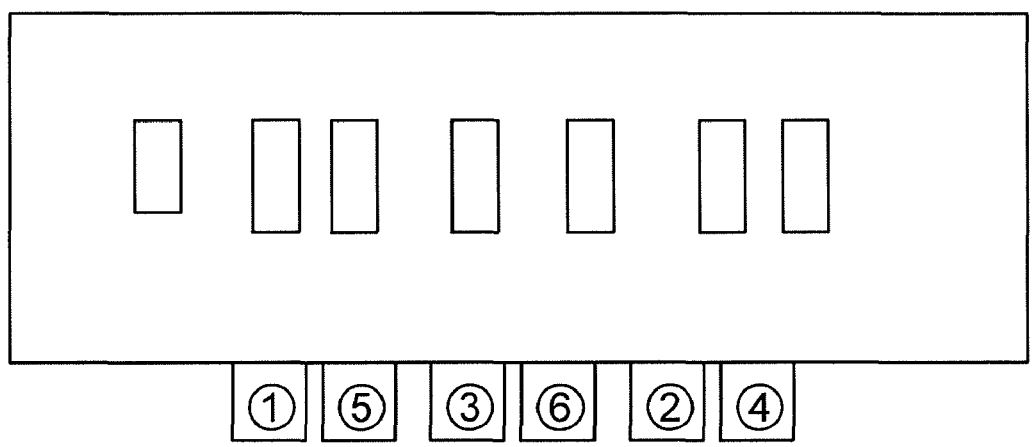
Figure 33C:
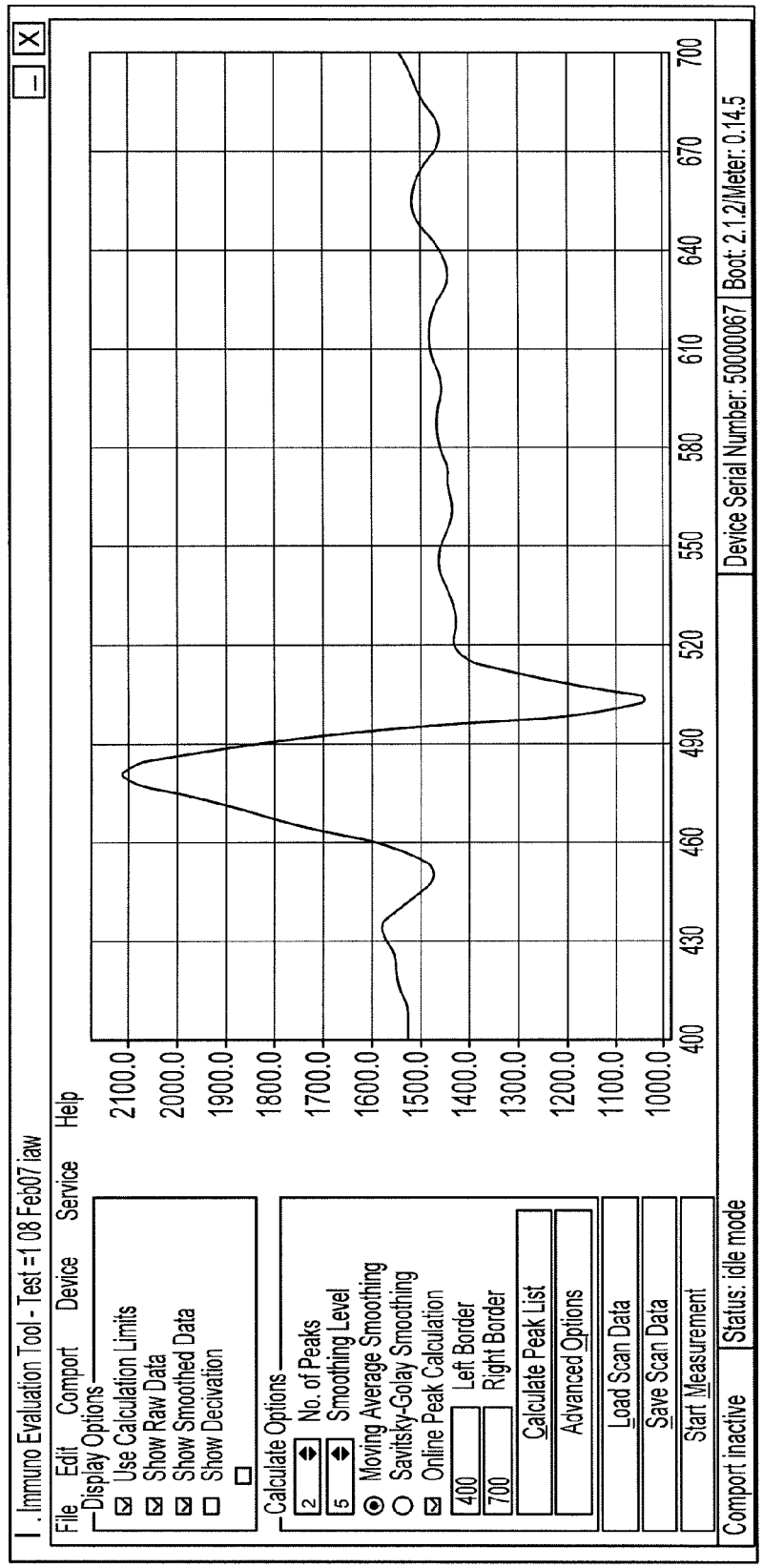
Figure 33D:
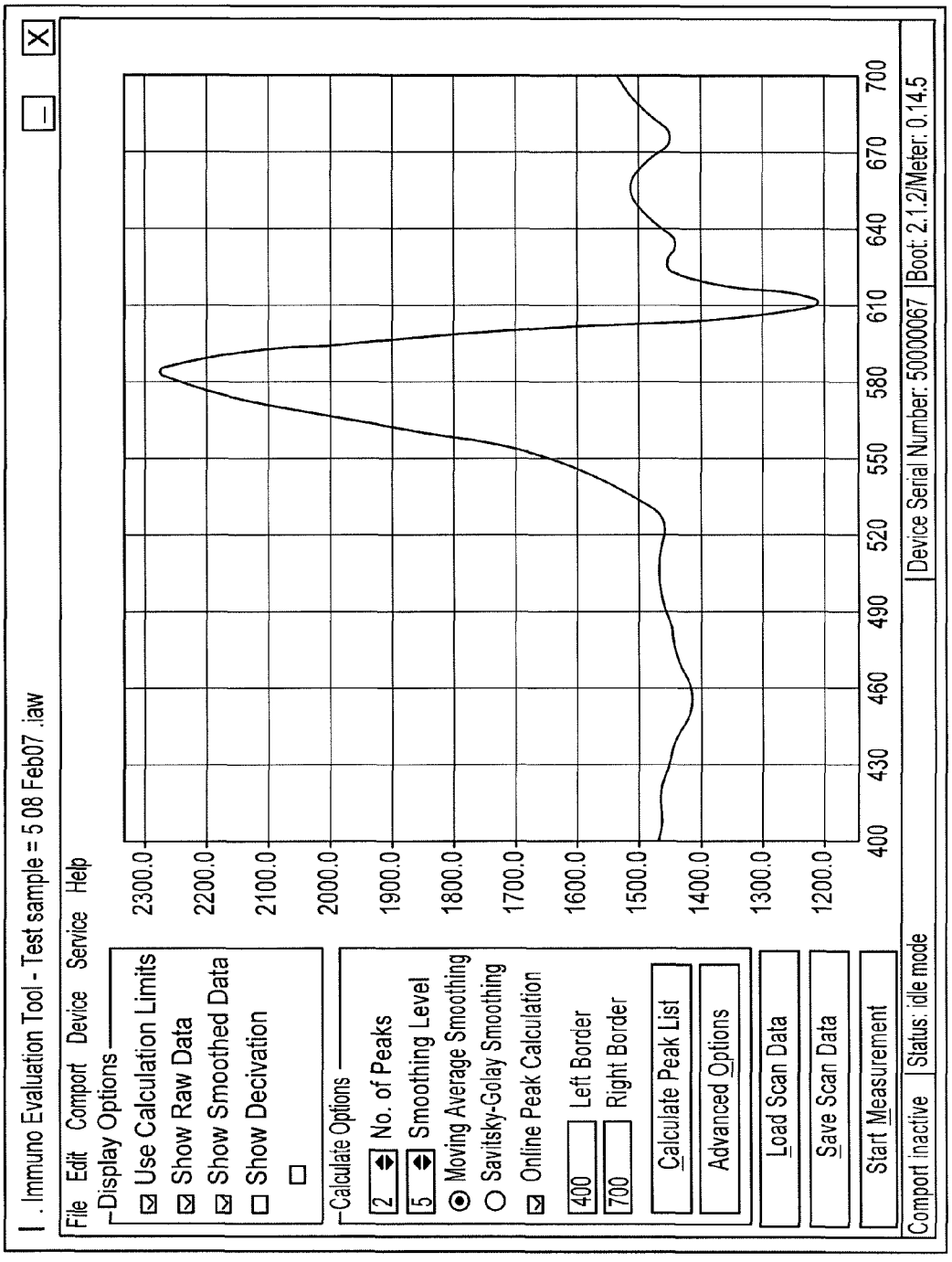
Figure 33E:
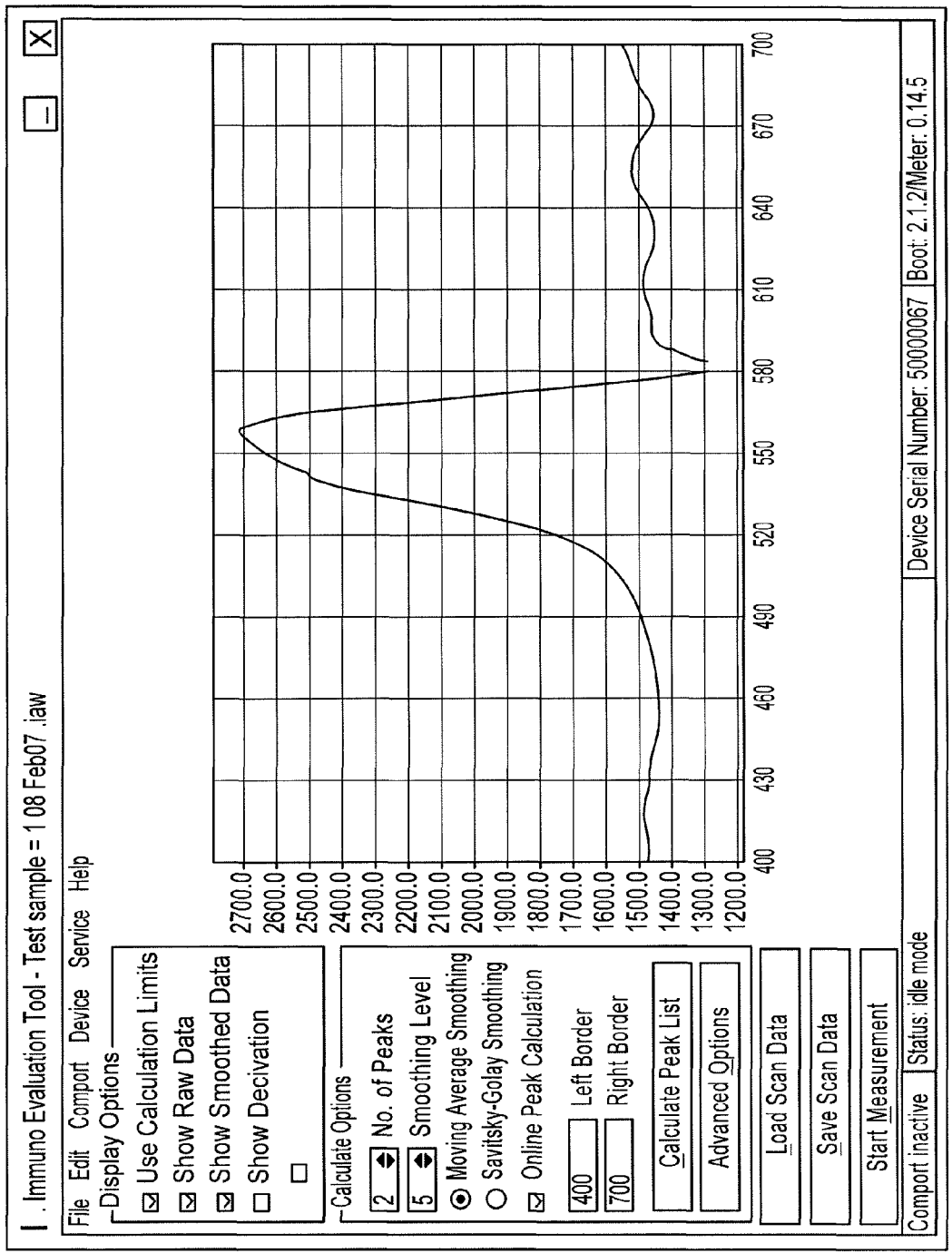
Figure 33F:
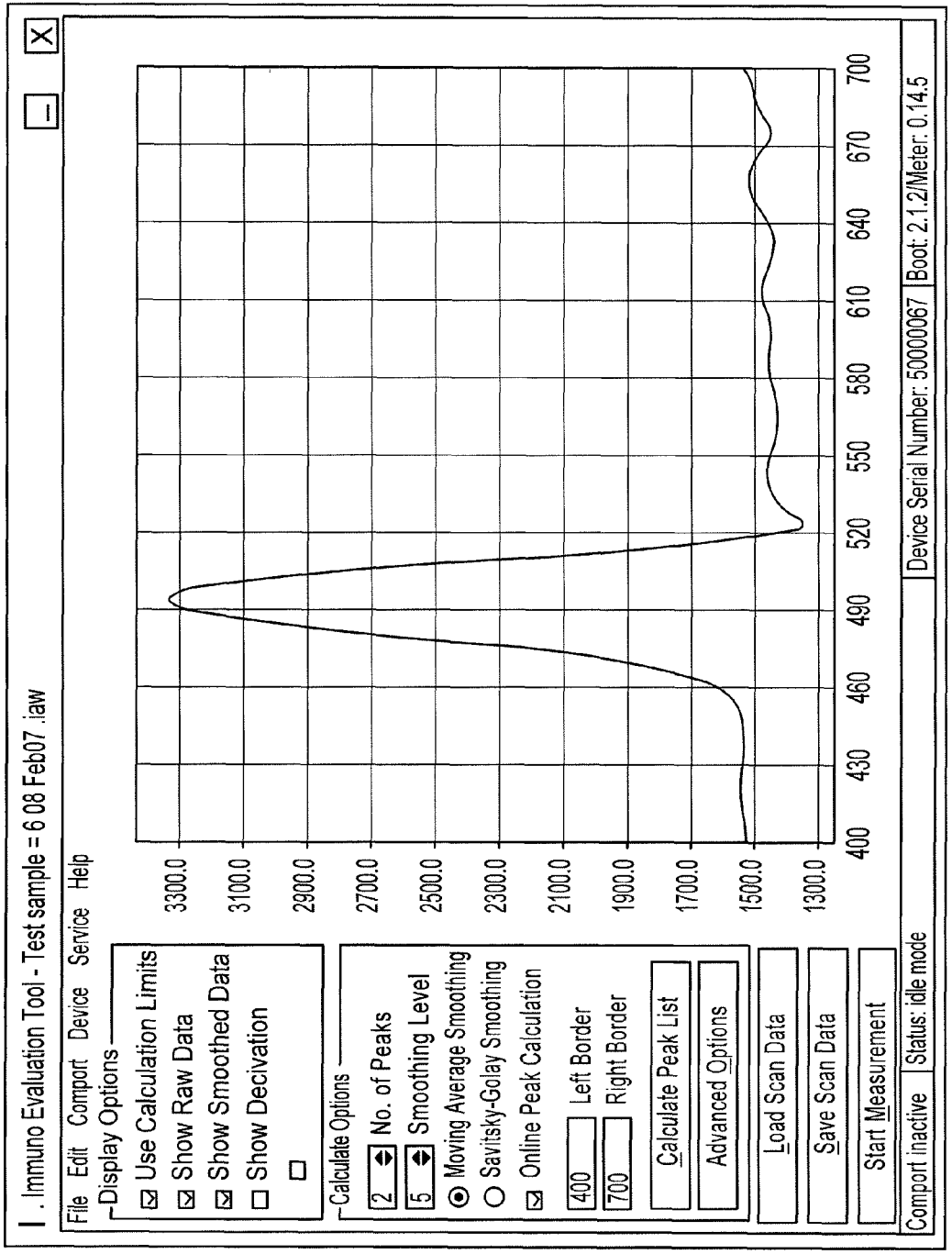
Figure 33G:
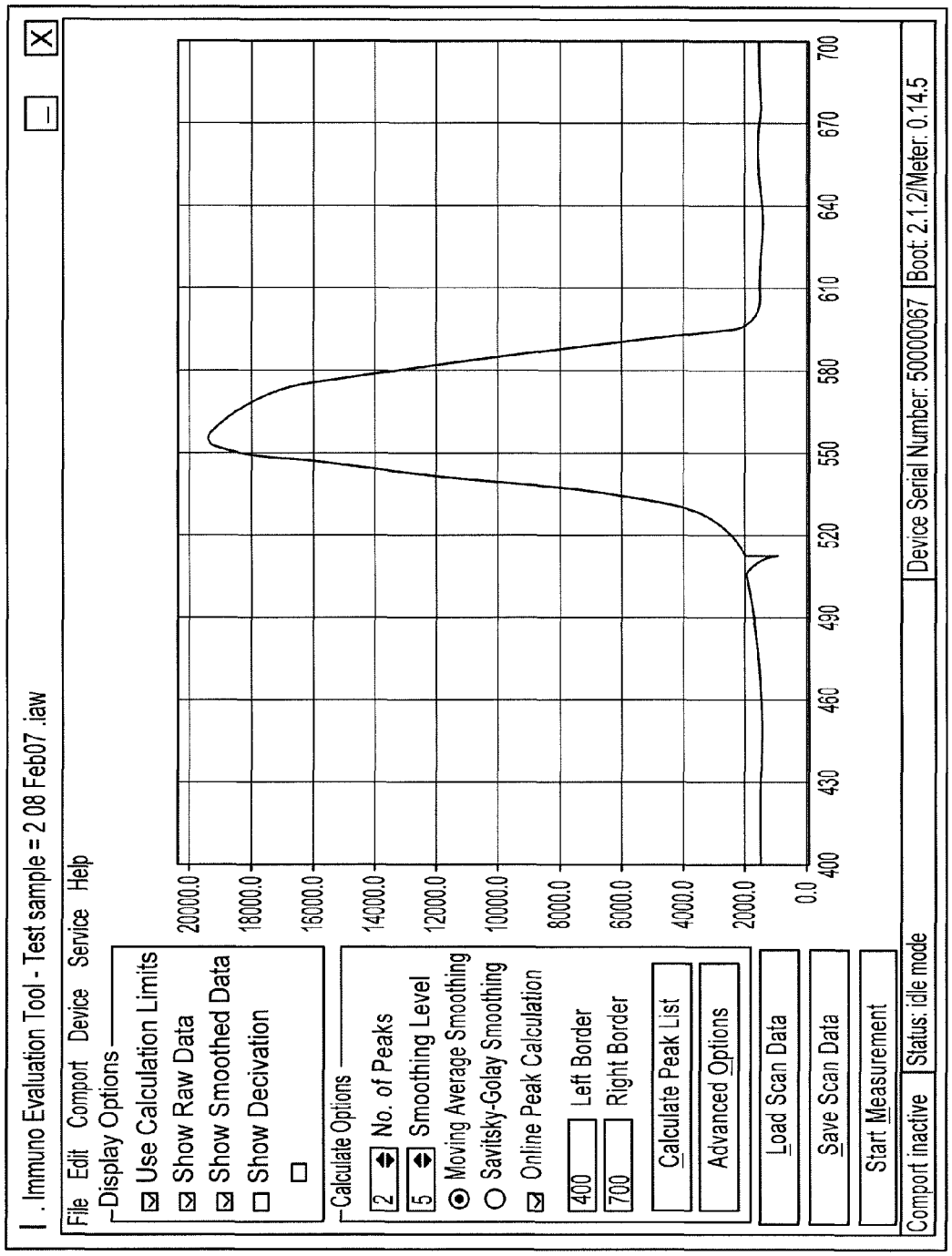
Figure 33H:
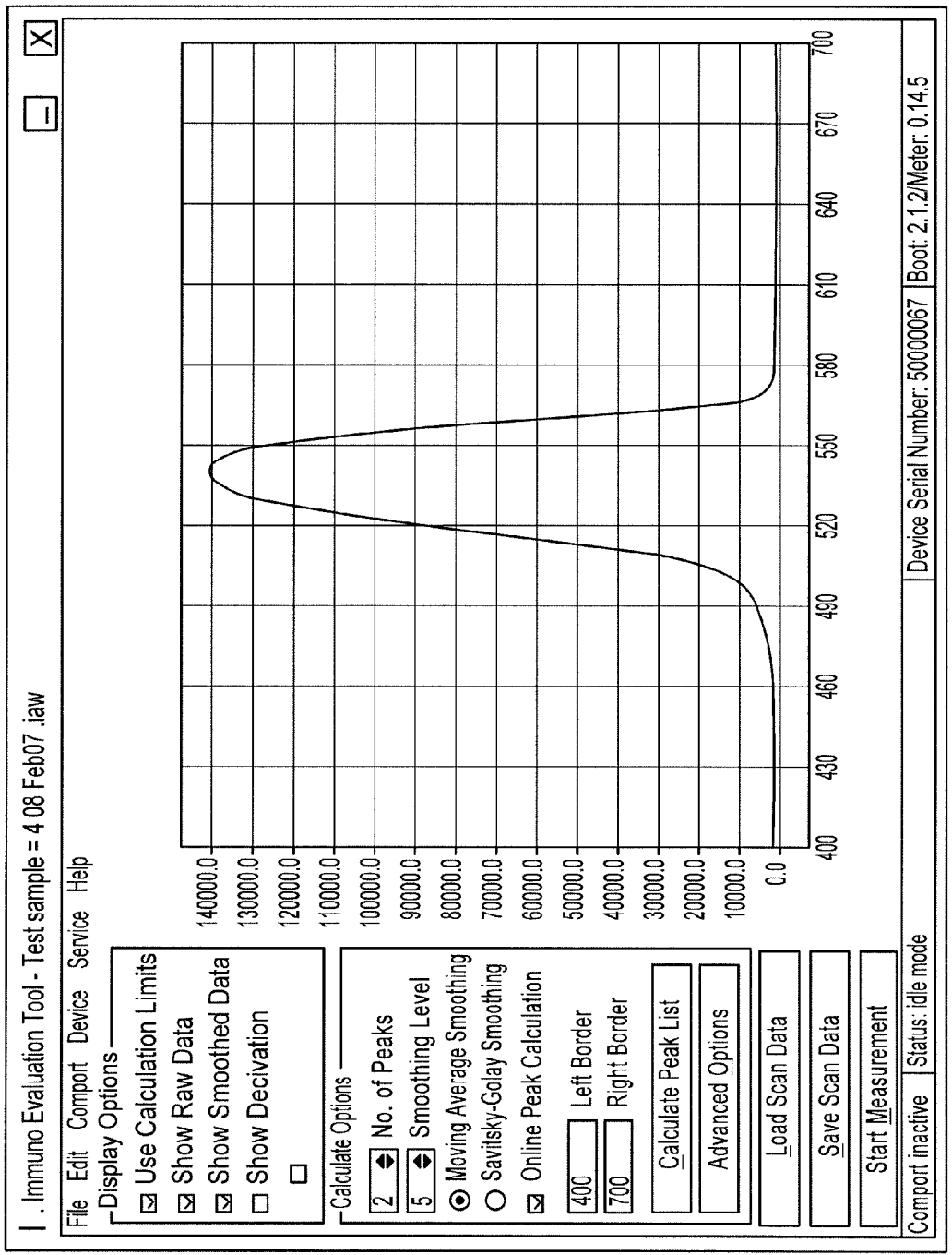

In some embodiments, hard standards are embedded or cast in a polymer material, including glass, plastic, vinyl, or acrylic FIG. 33B. Such embedded labels can be cast into appropriate shapes/sizes. Alternatively, such hard standards can be cut to appropriate sizes to be integrated into a reader. In one embodiment, hard standards are cut in rectangular, square, oblong, circular, or any polygon shape. In one embodiment, hard standards are cut into rectangular shapes, comprising dimensions for height of about 0.04, 0.045, 0.05, 0.055, 0.06, 0.065, 0.07, 0.075, 0.08, 0.085, 0.09, 0.095, 0.10, 0.11, 0.12, 0.125, 0.126, 0.127, 0.128, 0.129, 0.130, 0.135, 0.140, 0.150 inch; width of about 0.01, 0.02, 0.03, 0.035, 0.039, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 inch; and lengths of about 0.01, 0.02, 0.03, 0.035, 0.039, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 inch.

In one embodiment, a reader employing a hard standard as a reference is utilized for normalizing readers across a population, e.g., plotting subsequent reader performance against a pre-determined "Gold Standard" reader as illustrated in the following table:

TABLE 4

|  | Gold Std. | Test |
|---|---|---|
| S0 | 1000 | 900 |
| S1 | 5400 | 5000 |
| S2 | 10200 | 11000 |
| S3 | 19000 | 20000 |
| S4 | 22000 | 23000 |
| S5 | 50000 | 50000 |

Therefore, where y and x axis are Test reader and Gold Standard measurements respectively, the lower limit of detection is the intercept of the plotted line across the noise level (reading with no label).

In one embodiment, a Test Device comprises different pRNAs each patterned based on a specific analyte, a complementary SCD comprises a plurality of capture antibody linked to cognate pRNAs to those immobilized on the Test Device, and where said plurality comprising different subpopulation of antibodies specific for different analytes). Furthermore, the SCD reagent solution or substrate (e.g., lyophilized solid substrate) comprise detection probes, or a plurality of europium(III) labeled antibodies, consisting of the same subpopulations of antibodies specific for different analytes. Additional lanthanide labels that can be practiced in the present invention are known in the art, such as disclosed in U.S. Pat. No. 7,101,667. See also, e.g., Richardson F. S., "Terbium(III) and Europium(III) Ions as Luminescent probes and Stains for Biomolecular Systems," Chem. Rev., 82:541-552 (1982).

Therefore, depending on choice of labels, in some embodiments a signal is viewable by the unaided eye, while in other embodiments, a reader instrument is utilized in the practice of the present invention.

Capture Moieties.

In some embodiments, one member of a pair of complementary capture moieties will be bound to analyte-specific binding agent and the other member is immobilized on a line or spot FIG. 8A, respectively. As referred to herein, the terms "capture moiety" means a binding moiety that is specific for a partner or complementary capture moiety (e.g., pRNA specific for complementary pRNA, or avidin/streptavidin-bioin). In one embodiment, a Test Device comprises a combination of different capture moieties, wherein said capture moieties are comprise of different substances in number and/or type. For example, a test strip disposed in a Test Device can comprise one or more addressable test lines comprising pRNA, antibodies and specific binding members (e.g., avidin/biotin). Therefore, in various embodiments where two of the same type of capture moieties are disposed on a test strip, each will be specific for a different complementary partner molecule. For example, for two pRNA addressable lines, each line will comprise pRNA having different sequences which will specifically bind to pRNA of complementary sequences which are themselves bound to antibodies targeting a different analyte (e.g., Influenza A versus Influenza B). Furthermore, in such a configuration, additional test lines can comprise different capture moieties (e.g., antibodies or avidin) which themselves bind their cognate partner molecules. Thus in one embodiment, a test strip comprise 2, 3, 4, 5, 6, 7 or 8 addressable test lines, which can comprise any combination of 1, 2, 3 or 4 different types of capture moieties.

Where multiplexed (i.e., multianalyte) detection is desired, a plurality of capture moieties is utilized, antibodies specific for one analyte(s) will comprise a member of one specific pair of complementary capture moieties and antibodies that specifically bind a second and different analyte(s) will comprise a member of a second and different specific pair of complementary capture moieties, and so on. Thus, in one embodiment, a plurality of different analyte(s) can be detected, where the cognate member of a pair of capture moieties is immobilized in a discrete location on a test membrane comprised in the test implement. For example, a plurality of antibodies in an SCD is comprised of antibodies targeting different influenza virus strains and or subtypes, where said antibodies are comprised of pairs of detection antibody-capture antibody and where the capture antibody has a specific capture moiety. Further, each population of antibodies in the plurality of antibodies is defined by the particular target analyte to which the antibody binds. Thus, all capture antibodies directed to one specific target analyte will have the same capture moiety, for which cognate/complementary capture moieties are disposed in the Test Device.

In various embodiments, capture moieties are comprised of an oligonucleotide, avidin, streptavidin, pyranosyl RNA (pRNA), antigen-antibody binding pair selected for high affinity, aptamer or a combination thereof. In further embodiments, an oligonucleotide is DNA or RNA. Moreover, in some embodiments a combination of different capture moieties are utilized in the same detection system of the invention. For example, a capture moiety pair for one specific analyte comprises an oligonucleotide pair, while a capture pair for a different analyte comprises a capture moiety pair comprising pRNA, or avidin or streptavidin, etc. In other embodiments, a combination of different types of capture moieties is utilized in devices and assays of the invention to detect multiple analytes (e.g., plurality of capture antibodies whereby each population of capture antibodies specific for a single type of target analyte is linked to one type of capture moieties, and other analyte-specific antibodies are linked to others, such as aptamers, pRNA or streptavidin, etc.)

In one embodiment, all capture moieties are pRNAs, with multiple pairs of pRNA capture moiety and pRNA partner capture moiety (e.g., one is conjugated to a specific binding agent and the cognate pRNA is immobilized on the lateral flow membrane).

pRNA

Figure 32:
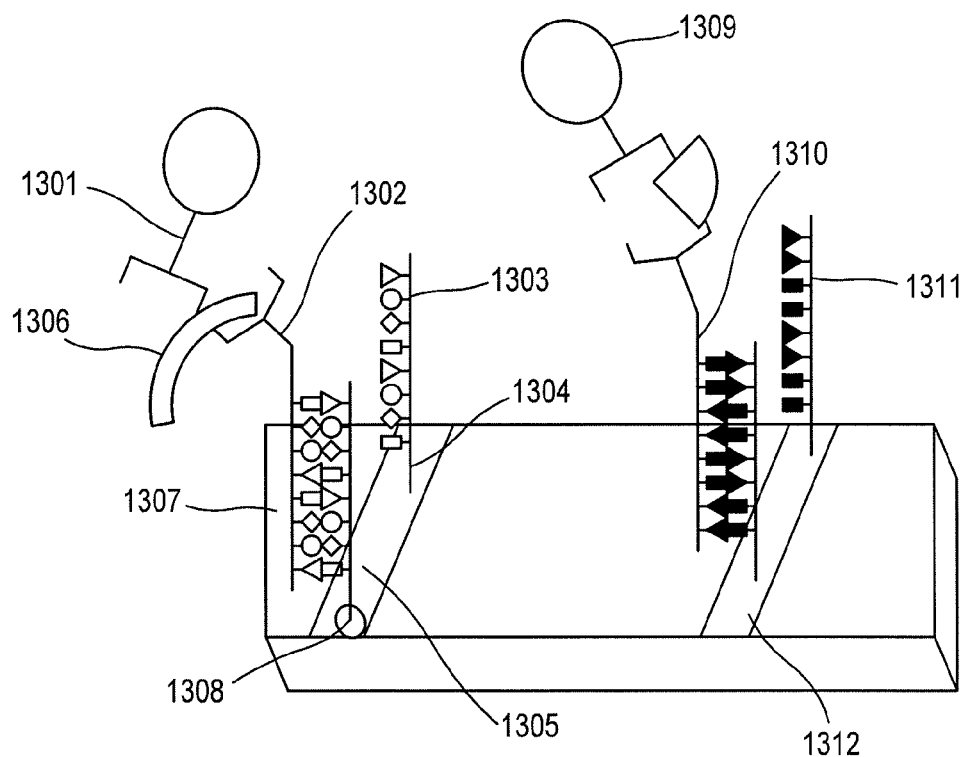
FIG. 32 provides a schematic of pRNA binding of multiple analytes on a test strip.

In one aspect of the invention, combinations of complementary pyranosyl RNA (pRNA) sequences are incorporated in the SCD/Test Devices of the invention enabling simultaneous specific detection of multiple analytes FIG. 32. In various embodiments one of a pair of homologous pRNA sequences is immobilized in a specific stripe or test zone in the Test Device, while the other of the pair of homologous pRNA sequences is conjugated to a binding moiety, which specifically binds to a target analyte. Thus in one embodiment, a target analyte is captured by the immobilized pRNA through interaction of the immobilized pRNA sequence with its binding pair pRNA. The analyte is detected by a detector molecule conjugated to a second binding moiety 1301 also specific for the same target analyte.

In some embodiments, pRNA binding partners are selected from but not limited to the following pRNAs

TABLE 5

| Name | 4'-2' | SEQ ID NO: |
|---|---|---|
| 102a10-3-NH2 | TAGAACGAAG | 92 |
| 102b10-3-NH2 | CTTCGTTCTA | 93 |
| 119a10-1-NH2 | TCAGTGGATG | 94 |
| 119b10-1-NH2 | CATCCACTGA | 95 |
| 3a10-1-NH2 | GTATTGCGAG | 96 |
| 3b10-1-NH2 | CTCGCAATAC | 97 |
| 102a8-2-NH2 | AACGATTC | 98 |
| 102b8-2-NH2 | GAATCGTT | 99 |
| 119a8-1-NH2 | AGTGGATG | 100 |
| 119b8-1-NH2 | CATCCACT | 101 |
| 3a8-1-NH2 | GTATTGCG | 102 |
| 3b8-1-NH2 | CGCAATAC | 103 |
| 4a8 | ATGCCTTC | 104 |
| 4b8 | GAAGGCAT | 105 |
| 5a8 | TGATGGAC | 106 |
| 5b8 | GTGCATCA | 107 |
| 6a8 | CAGTAGTG | 108 |
| 6b8 | CACTACTG | 109 |
| 7a8 | TTCCTGAG | 110 |
| 7b8 | CTCAGGAA | 111 |
| 8a8 | GACTCTCT | 112 |
| 8b8 | AGAGAGTC | 113 | all oligos with 4'-C12 amino and 2'-hexanol groups

Figure 26:
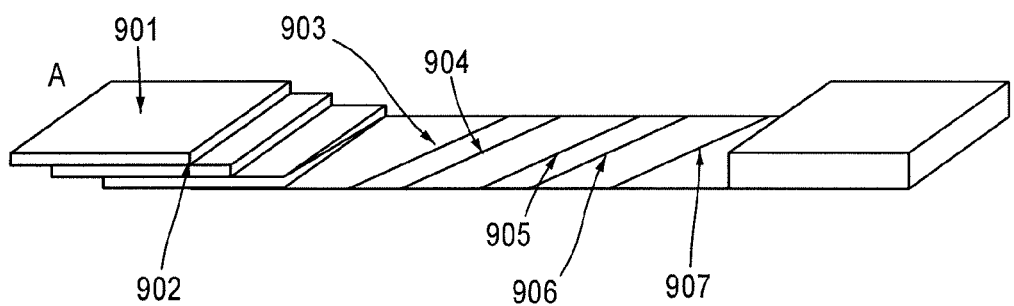
FIG. 26 illustrates a test device comprising multiple test lines for different type and subtypes of an analyte; 901 filter or sample pad onto which a sample is applied; 902 reagent pad; 903 test line for type 1 of an analyte/infectious agent; 904 type 2 of an analyte/infectious agent; 905 subtype of type 1 or type 2; 906 subtype of type 1 or type 2; 907 control line.

Therefore, where a plurality of capture probes (e.g., antibody linked to pRNA), each capture probe is linked to a capture moiety, for which a cognate capture probe is immobilized in a predetermined location on a test strip 310, 903, 904, 905, 906 comprised in a Test Device FIGS. 3, 26, 27. See also, FIG. 39-42, which illustrate the substantial sensitivity of pRNA capture.

Figure 30A:
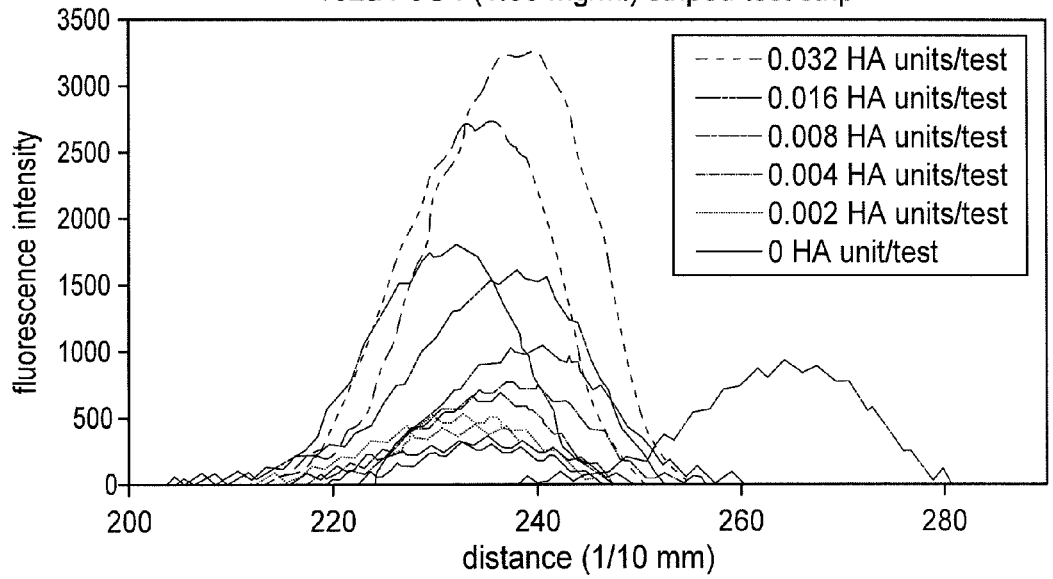
FIG. 30 illustrates (A) striped test strip results utilizing pRNA and (B) monoclonal antibodies.

Therefore, a sequence immobilized on a test strip at a specific addressable line will bind specifically to the complimentary pRNA conjugated with anti-analyte binding moieties (e.g., anti-virus antibody). The efficacy of such specificity is demonstrated in Example 6 (e.g., FIG. 30).

In some embodiments, a Test Device incorporating one or more pRNA binding pairs, provides sensitivity of about 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.2, 1.5, 1.7, 2.0, 2.5, 3.0, 3.5, 4.0, 4.5, 5.0, 5.5, 6.0, 6.5, 7.0, 7.5, 8.0, 8.5, 9.0, 9.5, 10.0, 15, 20, 30, 40 or 50 ng/mL.

In some embodiments pRNA is attached to a membrane (i.e., test strip) utilizing a protein linker. For example, pRNA can be conjugated to a hydrophilic protein. In one embodiment, the linker protein has a molecular weight of at least from about 500, 600, 700, 800, 900, 1000, 1500, 2000, 2500, 3000, 3500, 4000, 4500, 5000, 5500, 6000, 6500, 7500, 8000, 9000, 10000, 20000, 30000, 40000, 50000, 60000, 70000, 80000, 90000, 100000, 110000, 120000, 130000, 140000, 150000, 160000, 170000, 180000, 190000, 200000, 225000, 250000, 300000, 350000 to about 450000. Such a linker can range in size from about s about 5 to 10, 6 to 11, 7 to 12, 8 to 13, 9 to 14, 10 to 15, 11 to 16, 12 to 17, 13 to 18, 14 to 19, 15 to 20, 16 to 21, 17 to 22, 18 to 23, 19 to 24, 20 to 25, 21 to 26, 22 to 27, 23 to 28, 24 to 29, 25 to 30, 35, 40, 45 or 50 AA long. The linker can be a peptide or polypeptide. In one embodiment, the linker is BSA or IgG.

In one embodiment, pRNA is coupled to a hydrophilic protein/peptide via a covalent bond between the pRNA molecule and the hydrophilic protein. A solution containing the pRNA-protein complex is applied to defined regions on a test membrane (e.g., nitrocellulose), whereby the protein anchor binds to the membrane in a an irreversible. The pRNA is then available for use in the assay. In one embodiment, the anchor/linker protein is a hydrophilic protein and the test membrane is nitrocellulose.

As indicated previously, a Test Device can comprise addressable test lines utilizing different types of capture moieties (e.g., a combination of antibodies, nucleic acids, pRNA, avidin/streptavidin/biotin). In one embodiment (e.g., FIG. 32), at least one addressable line or specific capture zone 1305, 1312 comprises a pRNA 1304, 1311 sequence that is bound to a solid support 1308 (e.g., nitrocellulose, polystyrene, glass, plastic, metal, etc.) and is specific in binding for a homologous pRNA sequence conjugated to a second binding moiety 1302, 1310 that is specific for a particular target analyte 1306. Furthermore, a first binder molecule is a partner to the first binder molecule and said second binder molecule is conjugated to a detector molecule 1301, 1309 (e.g., fluorescent label). As demonstrated in Example 6 herein, pRNA is effectively immobilized and can specifically bind a complementary sequence to allow detection of an analyte. As such, pRNA provides a novel tool for detecting multiple analytes based on the great specificity and avidity of pRNA molecules.

In one embodiment, pRNA molecules are disposed on 1, 2, 3, 4, 5, 6, or 7 distinct addressable lines (i.e., capture zones) in a Test Device. In other embodiments, pRNA are utilized in combination with antibodies, nucleic acid binding pairs, and avidin/streptavidin, digoxin/anti-digoxin. For example, a Test Device comprise a test strip with 5 addressable test/capture zones, wherein each test zone is specific for a distinct analyte (e.g., influenza type A or B) and/or subtype (e.g., influenza A pandemic and non-pandemic subtypes). Thus, for example, two test zones utilized pRNA binding, while one utilizes strepavidin/avidin-biotin, while another utilizes fixed antibody, and yet another utilizes DNA/RNA. In this example, for each type of binding system, there is a complementary binding partner that is specific for the target analyte which is "captured" on the particular test zone. Further, as described herein, the analyte is also bound by a binder that is conjugated to a detector molecule/label (e.g., fluorescence label). As such, the once the analyte-detector-binding partner complex flows through the Test Device, the complex is captured at the distinct test zone having the immobilized binding partner.

As such a central aspect of the present SCD/Test Devices of the invention is that they can be configured to detect multiple analytes, including cells, cell components (e.g., cell markers, cell surface markers), proteins (e.g., enzymes) and the such.

In one embodiment, SCD/Test Devices of the invention can be used in a method to assay for any pathogenic conditions for which particular corresponding analytes are know or are identified in future. The SCD and Test Device can be configured to provide any combination of the detection reagents disclosed herein (e.g., pRNA, nucleic acids, antibodies, specific binding partners, e.g., avidin/biotin). For example, multiple analytes corresponding to myocardial infarction (MI) can be identified in detecting/diagnosing MI. Markers for various conditions are known in the art, such as for cardiac markers disclosed in U.S. Pat. Nos. 5,604,105; 5,710,008; 5,747,274, 5,744,358 and 5,290,678, the disclosures of each of which is incorporated by reference herein in its entirety.

In one embodiment, the devices of the invention provide a three in one assay for protein based cardiac markers of myocardial infarction would be designed (See Example 10).

In one embodiment, a sample is applied in a way that enables mixing with a mixture (in series or in parallel) of a first binder conjugated to a detector reagent (e.g., combinations of gold microparticles and fluorescent label) and with a second binder conjugated to a first member of a pRNA homologous binding pair which may or may not contain materials to enable an immune binding reaction and/or specific binding of pRNA homologous binding pairs.

If desired a pre-incubation is designed into the system whereby the first and second binders are allowed to attach to and bridge the analyte forming complex, and such a step can be during the flow of reagents to the test or capture zone. Alternatively, the flow may be stopped to allow for the reaction to come closer to completion. In yet another embodiment, the reagent mix in an SCD of the invention prior to be applied to a Test Device.

A mixture flows via capillary action or hydrostatic pressure from any of several mechanism or other non-capillary action along the surface of or within a matrix of a solid material/substrate (e.g., test strip) a flowing the first and second homologous binding pairs to come into contact as the reaction mixture passes over/through the test capture zone. If the first and second binder have bridged the analyte FIG. 32 the detector reagent (e.g., Europium) will accumulate at die test/capture zone yielding a signal that can be interpreted visually or using an instrument reader.

In embodiments where multiple different analytes are sought to be detected, different detector reagents are used for each analyte and each different analyte is captured in a single detection/capture zone. An instrument reader is used to distinguish between the signal for each analyte. In one embodiment, the instrument reader can detect a single to provide for qualitative and quantitative measurement.

In another embodiment, unique pRNA homologous binding pairs are utilized for each target analyte.

In another embodiment a wash buffer or reagent buffer is released through the flow path (as described herein) where said buffer can comprise a reagent that yields the release of energy in any of several forms that can be detected with an instrument, reader or visually. For example, the reaction can result in release of light, electrons or can require the input of electrons plus a substrate yielding the release of light. Such reactions are known to one of skill in the art.

Such reactions can result in enablement of a fluorescent compound to fluoresce after coming into contact with the running/wash buffer, resulting in release of electrons, protons, neutrons, which can be detected by an instrument or reader as described herein.

Aptamers.

In some embodiments, capture moieties are aptamer molecules that are can be interchangeably utilized with a capture probe or as an immobilized capture moiety included in the Test Device axial flow membrane. Aptamers include nucleic acids that are identified from a candidate mixture of nucleic acids. In a preferred embodiment, aptamers include nucleic acid sequences that are substantially homologous to the nucleic acid ligands isolated by the SELEX method. Substantially homologous is meant a degree of primary sequence homology in excess of 70%, most preferably in excess of 80%. The "SELEX" methodology, as used herein, involves the combination of selected nucleic acid ligands, which interact with a target analyte in a desired action, for example binding to a protein, with amplification of those selected nucleic acids. Optional iterative cycling of the selection/amplification steps allows selection of one or a small number of nucleic acids, which interact most strongly with the target antigen/biomarker from a pool, which contains a very large number of nucleic acids. Cycling of the selection/amplification procedure is continued until a selected goal is achieved. The SELEX methodology is described in the following U.S. patents and patent applications: U.S. patent application Set. No. 07/536,428 and U.S. Pat. Nos. 5,475,096 and 5,270,163.

Infectious Agents.

In various embodiments of the present compositions and methods, an infectious agent can be any pathogen including without any limitation bacteria, yeast, fungi, virus, eukaryotic parasites, etc. In some embodiments, the infectious agent is influenza virus, parainfluenza virus, adenovirus, rhinovirus, coronavirus, hepatitis viruses A, B, C, D, E, etc, HIV, enterovirus, papillomavirus, coxsackievirus, herpes simplex virus, or Epstein-Barr virus. In other embodiments, the infectious agent is *Mycobacterium, Streptococcus, Salmonella, Shigella, Staplhylcococcus, Neisseria, Clostidium*, or *E. coli*. It will be apparent to one of skill in the art that the compositions and methods of the invention are readily adaptable to different infectious agents, by utilizing a different panel of binding agents (e.g., antibodies) that are specific for type(s) or subtype(s) of an infectious agents).

Usually the general type of an infectious agent can be the genus type of an infectious agent or any primary or first instance typing or identification of an infectious agent. A subtype of an infectious agent can be the species or strain type of an infectious agent or any secondary or subsequent typing of an infectious agent. According to the present invention, identification of the general type or subtype of an infectious agent can be carried out via various suitable test set ups. For example, identification of the general type of an infectious agent can include one or more screening tests for 1) a specific general type of an infectious agent, 2) certain desired or selected general types of an infectious agent, or 3) all or substantially all relevant general types of an infectious agent, or a combination thereof. Similarly identification of the subtype of an infectious agent can include one or more screening tests for 1) one or more specific subtypes of an infectious agent, 2) one or more specific subtypes of a particular general type of an infectious agent, 3) one or more specific subtypes of an infectious agent selected based on additional information associated with the subject being tested, e.g., one or more suspected or expected subtypes for a particular population or geographic location or 4) one or more potentially pandemic or epidemic subtypes of an infectious agent that is identical to or associated with the infectious agent tested for the general type, or a combination thereof.

According to another aspect of the present invention, the method provided by the present invention can optionally or additionally include identification of the general and/or subtype(s) of a second infectious agent that is closely related to the first infectious agent, or alternatively the infection of the second infectious agent is associated or likely coupled with the infection of the first infectious agent. In one embodiment, the method provided by the present invention includes identification of the general and subtype(s) of a virus as well as a bacterium. For example, HIV infection can be associated with certain bacterial infection therefore it will be useful to identify the general and subtype(s) of HIV as well as Mycobacterium and/or Pneumocystis carina. Specifically the method provided by the present invention includes identification of HIV and one or more species of Mycobacterium and or Pneumocystis carina.

In another embodiment, the method provided by the present invention includes identification of the general and subtype(s) of a first virus as well as a second virus. For example, the method provided by the present invention can include identification of the general and subtype(s) of HIV as well as hepatitis virus or alternatively the general and subtype(s) of HIV as well as the general type of hepatitis virus or certain strains of hepatitis virus. In one embodiment, the methods and compositions of the invention can be utilized in assays to detect *E. coli* 0157 (a very dangerous, often fatal infectious strain) in the presence of other enteric or infective strains. Another example would be in testing patients for influenza infection, where mutation or variation of the strains within subtypes is known to occur and some forms of influenza are far more pathogenic than others. A further example is detection of different types of HIV, for example HIV-1 and HIV-2. In one aspect identification of the general type of human immunodeficiency virus (HIV) can include screening for the presence of HIV whereas identification of the subtype of HIV can include screening for HIV-1, HIV-2, and/or other subtypes of HIV. Similarly identification of the general type of herpes virus such as simplex virus (HSV) can include screening for the presence of HSV whereas identification of the subtype of HSV can include screening for HSV type 1 and/or HSV type 2 or for Epstein-Barr virus and subtypes of EBV.

In still another particular aspect, identification of the general type of enterovirus can include screening for the presence of one or more enteroviruses, e.g., poliovirus, coxsackievirus, echovirus, designated enterovirus, etc. whereas identification of the subtype of enterovirus can include screening for poliovirus, e.g., serotype 1-3, coxsackievirus A, e.g., serotype 1-22 and 24, coxsackievirus B, e.g., serotype 1-6, echovirus, e.g., serotype 1-9, 11-27, 29-31, and designated enterovirus, e.g., enterovirus 68-71, etc.

In general, with respect to a bacterial infectious agent identification of the general and subtype of a bacterial infectious agent includes screening for the genus and one or more species or strains of the bacterial infectious agent that are relevant to the infection and/or the agent's antimicrobial resistance. In one embodiment, identification of the general and subtype of a bacterial infectious agent includes screening for *Mycobacterium* and one or more species of *Mycobacterium* including without limitation tuberculosis, avium, bovis, chelonei, fortuitum, intracellulare, kanisasii, leprae, etc. In another embodiment, identification of the general and subtype of a bacterial infectious agent includes screening for *Salmonella* and one or more species of *Salmonella* including without limitation typhi, enteritidis, etc. In yet another embodiment, identification of the general and subtype of a bacterial infectious agent includes screening for *Shigella* and one or more species of *Shigella* including without limitation dysenteriae. In yet another embodiment, identification of the general and subtype of a bacterial infectious agent includes screening for *Streptococcus* and one or more species of *Streptococcus* including without limitation pneumonia, pyogenes (group A), etc. In still yet another embodiment, identification of the general and subtype of a bacterial infectious agent includes screening for *E. coli* and one or more strains of *E. coli* including without limitation enterotoxigenic strains.

According to the present invention, screening test(s) used for the identification of the general and subtype(s) of an infectious agent can be any suitable tests known or later discovered in the field. For example, the screening tests of the present invention can be a non-nucleic acid based test including without any limitation a protein, peptide, amino acid, ligand, or chemistry based test. In one embodiment, the screening test of the present invention is a test based on the presence or absence of one or more structural proteins of an infectious agent, e.g., glycoproteins, envelop proteins, polysaccharides, etc. In another embodiment, the screening test of the present invention is a test based on the presence or absence of one or more antigens or epitopes, or antibodies to an infectious agent. In yet another embodiment, the screening test of the present invention is a test based on the presence or absence of one or more substances that is released or metabolized by an infectious agent. In still yet another embodiment, the screening test of the present invention is a test based on the presence or absence of one or more substances derived from a host cell associated with or generated by the infection of an infectious agent.

In one particular aspect, the non-nucleic acid based screening test of the present invention includes the commonly used ligand binding or immunoassays, e.g., ligand or immunochromatographic assays. Many of these assays are based on the highly specific interactions between specific binding pairs. Examples of such binding pairs include antigen antibody, hapten/antibody, lectin carbohydrate, apoprotein/cofactor and biotin/(strept)avidin. Furthermore, many of these assays involve devices (e.g., solid phase, lateral-flow test strips, flowthrough tests) with one or more of the members of a binding pair attached to a mobile or immobile solid phase material such as latex beads, glass fibers, glass beads, cellulose strips or nitrocellulose membranes (U.S. Pat. Nos. 4,703, 017; 4,743,560; 5,073,484).

In one embodiment, the methods and apparatus of the invention are utilized to detect or identify an influenza type A subtype and/or influenza type B and/of influenza type C.

Influenza virus belongs to the genus orthomyxovirus in the family of *Orthomyxoviridae*. ssRNA enveloped viruses with a helical symmetry. Enveloped particles 80-120 nm in diameter. The RNA is closely associated with the nucleoprotein (NP) to form a helical structure. The genome is segmented, with 8 RNA fragments (7 for influenza C). There are 4 principle antigens present, the hemagglutinin (H), neuraminidase (N), nucleoprotein (NP), and the matrix (M) proteins. The NP is a type-specific antigen which occurs in 3 forms, A, B and C, which provides the basis for the classification of human and non-human influenza viruses. The matrix protein (M protein) surrounds the nucleocapsid and makes up 35-45% of the particle mass. Furthermore, 2 surface glycoproteins are seen on the surface as rod-shaped projections. The hemagglutinin (H) is made up of 2 subunits, H1 and H2. Hemagglutinin mediates the attachment of the virus to the cellular receptor. Neuraminidase molecules are present in lesser quantities in the envelope. The antigenic differences of the hemagglutinin and the neuraminidase antigens of influenza A viruses provide the basis of their classification into subtypes. e.g., A/Hong Kong/1/68 (H3N2) signifies an influenza A virus isolated from a patient in 1968, and of subtype H3N2.

In various embodiments, the methods and apparatus of the invention are directed to detecting or identifying influenza virus type A which is defined by HxNy where x is 1-16 and is 1-9, or any combination of xy thereof. For example, in one embodiment, the methods and apparatus of the invention is utilized to detect influenza A subtype H1N5. Thus, a plurality of detection probes and capture probes targeting different subtypes of influenza virus are disposed in an SCD of the invention. In one embodiment, the assay is utilized to detect Influenza A (with subtypes H1/H3, and a pandemic subtype H5) and Influenza B.

In particular, the general type of an influenza virus can be any type designated based on antigenic characteristics of the nucleoprotein and matrix protein antigens, e.g., type A, B, or C influenza virus, whereas the subtype can be one or more subdivided types of an influenza virus on the basis of an antigen, e.g. one or more subtypes of influenza type A or type B virus characterized by a surface antigen such as hemagglutinin (H) or neuraminidase (N).

In one embodiment, identification of the general type of influenza virus includes screening for type A, type B, and/or type C influenza virus whereas identification of the subtype of influenza virus, e.g., type A virus includes screening for one or more expected subtypes of type A, e.g., subtypes expected to be present in the population at the time of testing, and optionally one or more suspected subtypes, e.g., subtypes under surveillance for an outbreak such as epidemic or pandemic outbreak. In another embodiment, identification of the general type of influenza virus includes screening for type A and type B influenza virus whereas identification of the subtype of influenza virus, e.g., type A virus includes screening for one or more subtypes used for the production of the influenza vaccine, e.g., current vaccine subtypes(s) or strain(s) for the testing season including subtypes and/or strains expected to be in circulation during the next influenza season. In yet another embodiment, identification of the general type of influenza virus includes screening for type A and type B influenza virus whereas identification of the subtype of influenza virus, e.g., type A includes screening for one or more subtype(s) or strain(s) used for the production of the influenza vaccine and one or more subtype(s) or strain(s) suspected for the cause of a pandemic outbreak, e.g., one or more avian subtype(s) or strain(s) such as H5N1 or the derivatives thereof.

In yet another embodiment, identification of general type of influenza virus includes screening for type A and type B influenza virus whereas identification of the subtype of an influenza virus, e.g., type A includes screening for one or more common or expected subtypes in circulation including, without any limitation, a) $H_1$ and $H_3$, b) $H_1$, $H_3$, and $H_2$, c) $H_1$, $H_2$, $H_3$, and $H_9$, d) $H_1$, $H_3$, and $N_1$, e) $H_1$, $H_3$, $N_1$, and $N_2$, f) $H_1$, $H_3$, and $N_2$, g) $N_2$, and h) $N_1$ and $N_2$. For example, a screening test for the subtype identification of type A influenza virus can be directed to the identification of the presence of any one of the subtypes listed in the subtype group of a), b), c), d), e), f), g), or b) e.g., without necessarily identifying the presence of a specific subtype in a subtype group. Alternatively screening test for the subtype identification of type A influenza virus can be directed to the identification of the presence or absence of each and everyone of the subtypes listed in a), b), c), d), e), f), g), or h) e.g., identifying the presence of a specific subtype in a subtype group.

In still another embodiment, identification of general type of influenza virus includes screening for type A and type B influenza virus whereas identification of the subtype of an influenza virus, e.g., type A includes screening for one or more pandemic or un-expected subtypes in circulation including, without any limitation, a) $H_5$, b) $H_5$ and $H_7$, c) $H_5$, $H_7$, and $H_9$, d) $N_2$, $N_7$, and $N_8$, e) $H_5$ and $N_2$, f) $H_5$ and $N_1$, g) $H_5$ and $N_8$, h) $H_5$, $N_8$, $H_7$, and $N_7$, i) $H_5$, H7, $H_9$, $N_7$, and $N_8$. For example, a screening test for the subtype identification of type A influenza virus can be directed to the identification of the presence of any one of the subtypes listed in the subtype group of a), b), c), d), e), f), g), h), or i) e.g., without necessarily identifying the presence of a specific subtype in a subtype group. Alternatively screening test for the subtype identification of type A influenza virus can be directed to the identification of the presence or absence of each and everyone of the subtypes listed in a), b), c), d), e), f), g), h), or i), e.g., identifying the presence of a specific subtype in a subtype group.

In another particular aspect, the general type of hepatitis virus can be A, B, and C virus with each virus possibly having several subtypes including mutant strains. In one embodiment, identification of the general type of hepatitis virus includes screening for A, B, and/or C hepatitis virus whereas identification of the subtype of hepatitis virus includes screening for subtypes or mutant strains of A, B, and C hepatitis viruses, respectively. In another embodiment, identification of the general type of hepatitis virus includes screening for hepatitis B virus whereas identification of the subtype of hepatitis virus includes screening for one or more subtypes and/or mutant strains of hepatitis B virus. In yet another embodiment, identification of the general type of hepatitis virus includes screening for hepatitis C virus whereas identification of the subtype of hepatitis virus includes screening for one or more of subtypes 1-9 of type C hepatitis virus.

In various embodiments, methods and apparatus of the invention can detect one or more different infectious agents. For example, a sampling implement can comprise a plurality of different antibodies, wherein multiple subgroups of antibodies are present, whereby each subgroup of antibodies specifically binds a different infectious agent. For example, a plurality of antibodies can comprise 2, 3, 4, 5, 6, 7, 8, 9 or 10 subgroups, wherein each subgroup of antibodies in the plurality of antibodies specifically binds a different infectious agent. In some embodiments, methods and apparatus of the invention detect a pandemic and non-pandemic infectious agent. In one embodiment, the pandemic and non-pandemic infectious agents are influenza virus.

The explosive nature of epidemic influenza and the specific clinical features of this disease have given reliable epidemiological records of this infection since the beginning of the nineteenth century. Several epidemics were recorded during the nineteenth century but the first pandemic was not accurately recorded until 1889-92. A second pandemic, probably originating in Europe, occurred in 1918-19, and is known as Spanish Influenza, which was responsible for 20-25 million deaths, principally in young adults.

Pandemics continued to occur regularly after the Spanish influenza, in 1932-33, 1947-48, 1957 and 1968. The next pandemic is thought to be overdue. These latter pandemics resembled the pandemic of 1890, affecting millions of people with a mild URTI and a small number of deaths. The H1N1 (swine) viruses probably appeared in 1918 and continued to circulate until 1957, at which time they were supplanted by the H2N2 (Asian) viruses. The H2N2 viruses were prevalent until 1968, when H3N2 (Hong Kong) strains appeared. The H1N1 virus reappeared in 1977 and did not replace the H3N2 subtype and both subtypes continued to cocirculate. Therefore, it is imperative that subjects are screened in an effective and accurate manner to determine with what strain and/or subtype an individual is infected. Furthermore, in some circumstances such sample collection and processing will necessarily occur in a point-of-care setting (e.g., in the field, without large numbers of subjects to sample and process, and with limited man power to effect such sampling).

As such, in one embodiment, the methods and apparatus of the invention are utilized in processing a large number of samples, in a point-of-care setting, where test results may be visualized (i.e., read) some period of time after the test is complete. For example, the period of time can be 30 minutes, 1 hour, 1.5 hour, 2 hours, 2.5 hours, 3 hours, 4 hours or 5 hours. In some embodiments, methods and apparatus in conjunction with the reagents disclosed herein provide high sensitivity and specificity where the fluorescent result can be read with very similar results over a long period of time. Thus, in some embodiments biological samples can be collected and processed, but set aside to be read a significant time later, which is greatly advantageous in point-of-care settings or where a large number of samples are collected with limited manpower or time to further process samples.

In yet another aspect of the invention, the compositions and methods of the invention are directed to detecting any one or more analytes present in a sample. As indicated above, for example, by utilizing different binding moieties that specifically bind markers associated with a condition, one or more analytes associated with MI can be detected. Therefore, an SCD and Test Device can comprise the necessary reagents to diagnose a disease or pathological condition, other than infectious diseases.

In some embodiments, the one or more analytes are markers associated with a pathological condition or disease. In another embodiment, the one or more analytes are polypeptides associated with a nutrional state or condition. In yet other embodiments, the one or more analytes are cell markers associated with cell cycle and growth. In another embodiment, the one or more analytes are associated with cell proliferation and differentiation. In one embodiment, cell markers are associated with cancer.

EXAMPLES

Example 1

Assay Volume and Chasing Buffer

To explore the optimal assay sample volume that will give the best sensitivity and to investigate if a chasing buffer will also increase the sensitivity and performance of the test strip.

Materials: Nitrocellulose Membrane: Millipore HiFlow 135 membrane, 2.5 cm in width. Cat. No. SHF1350425, Lot No. R68N46849, Code No. RK04414, roll No. 04OLI. Membrane was striped with monoclonal anti-H5N1 antibody, clone 3C8 at 1.0 mg/ml. Control line was striped with 1.5 mg/ml rabbit anti-mouse antibody. Wicking pad: 0.05% Tween-20 treated polyester pad, Ahlstrom grade 6613. Prepared Absorbent pad: Ahlstrom Grade 222 paper, 3.5 cm in width, purchased from Fisher, Cat. # 2228-1212, lot# 6150502. Anti-H5 3G4 gold conjugate was prepared by Nanogen POC at Toronto, Canada, OD of 3G4 gold conjugate at maximal absorbent peak was 112.54. Extraction buffer: 50 mM Tris-Cl, pH 8.15, 0.75 M NaCl, 1% BSA, 0.1% pluronic F68, 0.05% digested casein, 2 mM TCEP and 0.02% NaN$_3$, Recombinant H5 hemagglutinin (0.2 mg/mL) was provided by Nanogen POC, Toronto, Canada Protocol: Preparation of lateral flow test strip. Nitrocellulose membrane striped with antibodies was laminated on plastic card with 1-2 mm overlap with wicking pad and absorbent pad. No cover tape was applied on any components. Strips were cut in 5 mm in width.

Test: Extraction buffer ranged from 50-100 μL was mixed with 1.1 μL 3G4 gold conjugate and with or without 2 μL recombinant H5 hemagglutinin. Test was started by inserting strip into extraction buffer and result was scanned at 15 min, 20 min, 25 min and 30 min. For experiment with chasing buffer, see result for detail.

Result: FIG. 9 Test the strips with different volume of Extraction Buffer, at 15, 20, 25 and 30 minutes. FIG. 9A Test strips were tested in different volume of Extraction Buffer. At the 15, 20, 25 and 30 min, strips were taken out and scanned with Bio-Rad GS-800 Calibrated Densitometer. Lane 1, 2: 50 μL Extraction Buffer; Lane 3, 4: 60 μL Extraction Buffer; Lane 5, 6: 70 μL Extraction Buffer; Lane 7, 8: 80 μL Extraction Buffer; Lane 9, 10: 100 μL Extraction Buffer; FIG. 9B Compare the test line intensity of test strip with different volume of Extraction Buffer at different reading time.

TABLE 6

Data analysis of FIG. 9 with Quantity One.

| Lane Number | Extraction Buffer (μl) | Peak Intensity 15 min | 20 min | 25 min | 30 min |
|---|---|---|---|---|---|
| 1 | 50 | 55.6 | 62.3 | 63.1 | 62.5 |
| 2 | | 51.1 | 57.3 | 55.4 | 62.6 |
| 3 | 60 | 53.5 | 65.7 | 68.5 | 68.9 |
| 4 | | 51.6 | 63.8 | 66.2 | 66.5 |
| 5 | 70 | 45.6 | 57.9 | 60.4 | 60.7 |
| 6 | | 42.1 | 57.0 | 61.7 | 63.9 |
| 7 | 80 | 39.6 | 53.7 | 59.8 | 61.5 |
| 8 | | 42.9 | 57.9 | 64.7 | 65.4 |
| 9 | 100 | 35.2 | 49.2 | 54.6 | 55.6 |
| 10 | | 30.8 | 44.9 | 49.3 | 49.8 |

FIG. 10A Test Strip #3 with various amount of extraction buffer and effect of background clean-up on their negative control result.

TABLE 7

Data analysis of FIG. 10 with software Quantity One

| Lane Number | Extraction Buffer (μl) | Peak Intensity 15 min | 20 min |
|---|---|---|---|
| 1 | 50 | 3.8 | 5.4 |
| 2 | | 4.1 | 4.6 |
| 3 | 60 | 3.4 | 4.8 |
| 4 | | 3.4 | 5.5 |
| 5 | 70 | 3.4 | 2.9 |
| 6 | | 2.7 | 4.1 |

To various amount of extraction buffer, 1.1 μL 3G4 gold conjugate was added. Test was started by inserting snip to the assay solution and scanned at 15 min. (First roll). Then all the strips were transferred to tubes containing extraction buffer only and ran for 5 more minutes. The strips were scanned again. (Second roll).

FIG. 10B rest Strip #3 in various amount of extraction buffer and effect of background clean-up on their sensitivity.

To various amount of Extraction Buffer, 1.1 μL 3G4 gold conjugate and 2 μL recombinant H5 hemagglutinin was added. Test was started by inserting strip to the assay solution and scanned at 15 min. (First roll). Then all the strips were transferred to tubes containing extraction buffer only and ran for 5 more minutes. The strips were scanned again. (Second roll).

TABLE 8

Data analysis of FIG. 4 with software Quantity One

| Lane Number | Extraction Buffer (μL) | Peak Intensity 15 min | 20 min | Intensity change |
|---|---|---|---|---|
| 1 | 50 | 56.9 | 88.7 | 56% |
| 2 | | 57.8 | 94.4 | 63% |
| 3 | 60 | 50.2 | 78.3 | 56% |
| 4 | | 51.2 | 77.4 | 51% |
| 5 | 70 | 46.8 | 67.1 | 43% |
| 6 | | 47.9 | 73.4 | 53% |

Discussion. In the design of most of the rapid lateral flow tests for point-of-care, antibody conjugate usually is dried on a conjugate pad which is interfaced with nitrocellulose membrane. The disadvantage of this design is that dried conjugate may not release evenly and consistently from strip to strip, and from time to time due to materials for conjugate pad. Conversely, if antibody conjugate is premixed with assay solution, as long as the liquid flow is consistent, which is more likely to occur because once the wicking pad is wet, the flow speed actually is controlled by the membrane rather than the wicking material, the flow of antibody conjugate should be more consistent and even. Therefore in the above example, antibody gold conjugate was directly mixed with assay solution.

Initially, 100 μL Extraction Buffer was used for each test and the reading time of the assay was set at 15 min. It was found that at the end of 15 min, not all assay solutions were consumed. There was a waste of both analyte and gold conjugate. Experiment was designed to investigate what the optimal assay volume is in a relatively short reading time ranges. FIG. 9B and table 2 showed that with larger volume, such as 100 μL, of assay solution, longer time is required to get better sensitivity. However, with 50 μl of assay buffer, the color intensity of the test line does not increase much over different reading time after 15 min indicating that most of the analyte and gold conjugate have passed the capture line at 15 min. Although at 30 min the color intensity of the stripes tested with 100 μL assay solution almost reach the same level as those tested with low volume assay solution at 15 min, it is obvious that a 15 min test is more competitive than a 30 min test in the market.

However, due to the higher concentration of gold conjugate in a relatively small volume of assay solution, the background of test strips showed significant red background which reduced the contrast between the test line and the background and was cosmetically unattractive. FIG. 10B showed that running a chasing buffer after 15 men could significantly clean up the background; hence increase the sensitivity of the test by 43%-63%. The data also demonstrated again that a small assay volume, 50 μL, is a better choice for the test.

Example 2

Europium Bead Versus Prior Art System

Materials: Inactivated influenza A virus: Texas 1/77 (H3N2) from Microbix Biosystems, Inc. Cat.# EL-13-02, lot#13037A3; Inactivated influenza B virus: Hong Kong 5/72 from Microbix Biosystems, Inc. Cat.# EL-14-03, lot# 14057A2; Qiuidel QuickVue A+B Test, lot# 702391

Protocol: Virus dilution—Influenza A and influenza B viral preparations were diluted with saline to 4096 HA/mL and 409.6 HA/mL, respectively, before use. Assay procedure. Procedures described in the package insert of the Quidel test kit were followed and briefly reviewed here, Dispense all of the Extraction Reagent Solution from the reagent tube. Gently swirl the tube to dissolve its content. Spike virus into the tube. Place the swab into the Extraction Tube. Roll the swab at least three times while pressing the head against the bottom and side of the Extraction Tube. Leave the swab in the tube for 1 min. Roll the swab head against the inside of the tube as you remove it. Place the test strip into the Extraction Tube. Read result at 10 min.

Figure 11:
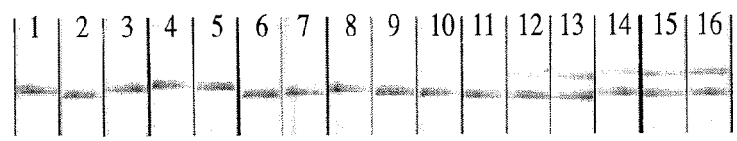
FIG. 11 illustrates two different tests for detection of influenza A.

Result: FIG. 11 Test QuickVue Flu A+B with different amount of influenza A virus, Texas 1/77. The test line is shown above the control line.

TABLE 9

Visual read result and data analysis of FIG. 4 with software Quantity One.

| Flu A virus (HA/test) | Lane No. | Peak intensity | Visual read result |
|---|---|---|---|
| 0 | 1 | 2.5 | − |
|  | 2 | 1.9 | − |
| 1.0 | 3 | 3.1 | − |
|  | 4 | 3.1 | − |
| 2.0 | 5 | 3.0 | − |
|  | 6 | 3.9 | − |
| 4.1 | 7 | 7.2 | + |
|  | 8 | 8.7 | + |
| 8.2 | 9 | 18.2 | + |
|  | 10 | 14.3 | + |
| 16.4 | 11 | 21.1 | + |
|  | 12 | 31.9 | + |
| 32.8 | 13 | 66.2 | + |
|  | 14 | 48.1 | + |
| 65.5 | 15 | 56.8 | + |
|  | 16 | 74.0 | + |

Peak intensity was analyzed with software Quantity One. Values were given by the software. Any values below 4 will be read as a negative with eyes.

Figure 12:
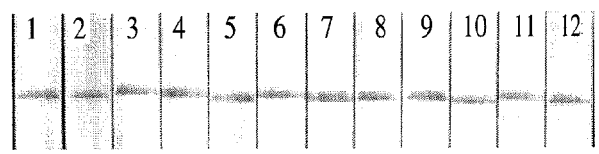
FIG. 12 illustrates two different tests for detection of influenza A and influenza B.

FIG. 12 Test QuickVue Flu A+B with different amount of influenza B virus, Hong Kong 5/72.

The test line for Type B is below the control line.

TABLE 10

Visual read result and data analysis of FIG. 4 with software Quantity One.

| Flu B virus (HA/test) | Lane No. | Peak Intensity | Visual read result |
|---|---|---|---|
| 0 | 1 | 2.9 | − |
|  | 2 | 0.2 | − |
| 0.41 | 3 | 1.6 | − |
|  | 4 | 1.9 | − |
| 0.82 | 5 | 2.3 | − |
|  | 6 | 3.5 | − |
| 1.64 | 7 | 4.2 | ± |
|  | 8 | 6.3 | + |
| 3.28 | 9 | 2.0 | − |
|  | 10 | 8.1 | + |
| 6.55 | 11 | 16.3 | + |
|  | 12 | 14.0 | + |

Peak intensity was analyzed with software Quantity One. Values were given by the software. Any values below 4 will be yield a negative result with a visual read.

TABLE 11

Test Quidel QuickVue Flu A + B with different amount of influenza B virus, Hong Kong 5/72

| | Virus (HA/test) | | | | | | |
|---|---|---|---|---|---|---|---|
| | 0 | | 0.41 | | 0.82 | | 1.64 |
| | | | | No. | | | |
| | 1 | 2 | 1 | 2 | 1 | 2 | 1 | 2 |
| Visual Result | − | − | ± | ± | ± | ± | + | + |

Example 3

Test the Detection Limit of Influenza A and B Test Using Gold Label

Materials: Anti-Flu A M4090913 gold conjugate was prepared by Nanogen POC at Toronto, Canada. OD was 102.69 at maximal absorbent peak. Anti-Flu B antibody 2/3 gold conjugate was prepared by Nanogen POC at Toronto, Canada. OD was 94.78 at maximal absorbent peak. See above for nitrocellulose membrane, wicking pad and absorbent pad. Membrane striped with anti-Flu B M2110171 antibody at 1.5 mg/ml and rabbit anti-mouse antibody at 1.5 mg/ml was prepared by Nanogen POC at Toronto, Canada, Membrane striped with anti-Flu A 7304 antibody at 1.5 mg/ml and rabbit anti-mouse antibody at 1.5 mg/ml was prepared by Nanogen POC at Toronto, Canada. Inactivated influenza A H3N2, Texas 1/77 was purchased from Microbix Biosystems, Inc. lot#13037A3, 40960 HA/mL.

Inactivated influenza B, Hong Kong 5/72 was purchased from Microbix, Biosystems, Inc., lot#14057A2, 40960 HA/mL; Molecular Biology Water, lot# 318105; 3× extraction buffer containing 0.15 M Tris-Cl, pH 8.0, 2.25 M NaCl, 0.3% Pluronic F68, 3% BSA, 6 mM TCEP, 1.5% digested casein and 0.06% $NaN_3$; 2× extraction buffer containing 0.1 M Tris-Cl, pH 8.0, 1.5 M NaCl, 0.2% Pluronic F68, 2% BSA, 4 mM TCEP, 1% digested casein and 0.04% $NaN_3$; 1× extraction buffer, lot# 2232-003.

Protocol: Preparation of lateral flow test strip (See above); Virus dilution: Inactivated influenza A, Texas 1/77 was diluted to 409.6 HA/mL with 10 mM PBS with 1% BSA. Inactivated influenza B, Hong Kong 5/72 was diluted to 40.96 HA/mL with the same buffer before use. Influenza A and B test with gold conjugate: For influenza A test, 16.7 µL 3× extraction buffer, 1.95 µL M4090913 gold conjugate and different amount of inactivated influenza A virus were added to a tube. $H_2O$ was added to a final volume of 50 µL. For influenza B test, 25 µL 2× extraction buffer, 2.12 µL 2/3 gold conjugate and different amount of virus were added to a tube, $H_2O$ was added to a final volume of 50 µL. Test was started by inserting the test strip into the assay solution. At 15 min, 50 µL 1× Extraction Buffer was added to the same tube and test was carried on for 5 more minutes. Results on strips were read with eyes and also analyzed with software Quantity One after strips were scanned with Bio-Rad GS-800 Calibrated desitometer.

Figure 13:
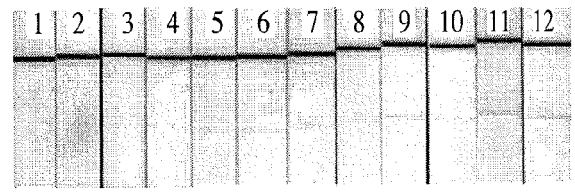
FIG. 13 illustrates the detection of influenza A using gold as label.

Result: FIG. 13. Test the limit of detection of influenza A test using gold as label.

TABLE 12

Figure 7:
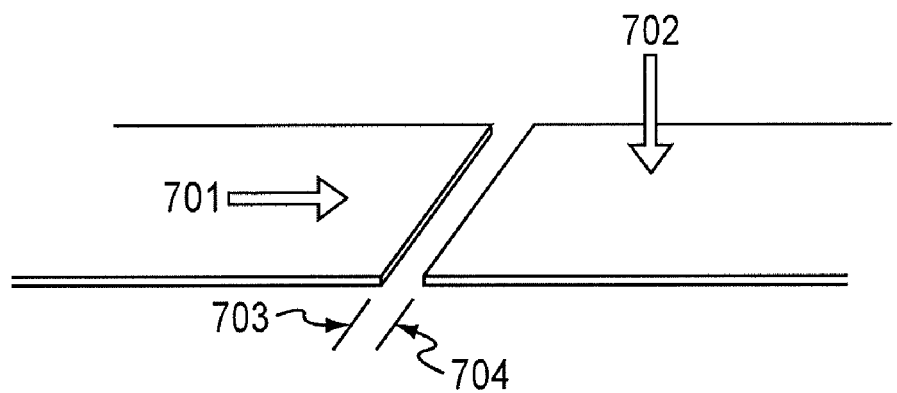
FIG. 7 illustrates a test device comprising a gap means.

Data analysis of FIG. 7 with software Quantity One and visual read result

| Virus HA/test | Lane No. | Peak Intensity | Peak Intensity(avg) | Visual read |
|---|---|---|---|---|
| 0 | 1 | 0 | 0 | − |
|  | 2 | 0 |  |  |
| 0.105 | 3 | 2.2 | 2.8 | − |
|  | 4 | 3.3 |  |  |
| 0.21 | 5 | 4.8 | 6.7 | + |
|  | 6 | 8.6 |  |  |
| 0.41 | 7 | 13.2 | 11.2 | + |
|  | 8 | 9.1 |  |  |
| 0.82 | 9 | 14.8 | 14.1 | + |
|  | 10 | 13.5 |  |  |
| 1.64 | 11 | 26.4 | 24.5 | + |
|  | 12 | 22.5 |  |  |

Values of peak intensity are the analysis result with Quantity One.

Figure 14:
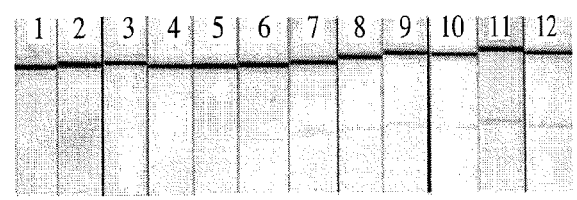
FIG. 14 illustrates the detection of influenza B using gold as label.

FIG. 14 Test the limit of detection of influenza B test using gold as label.

TABLE 13

Figure 9A:
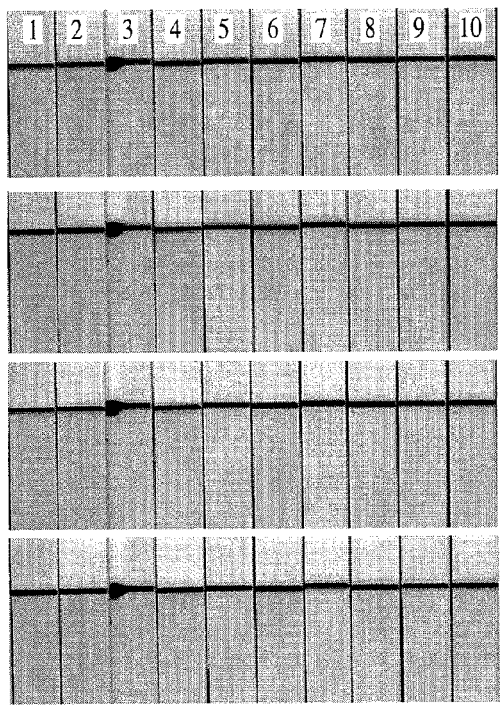
FIGS. 9A and 9B illustrates test strips tested with different volume of extraction buffer.
Figure 9B:
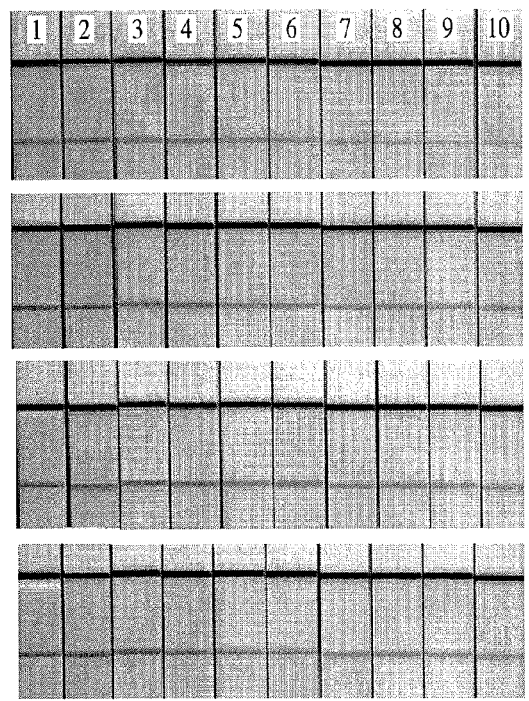
Figure 10A:
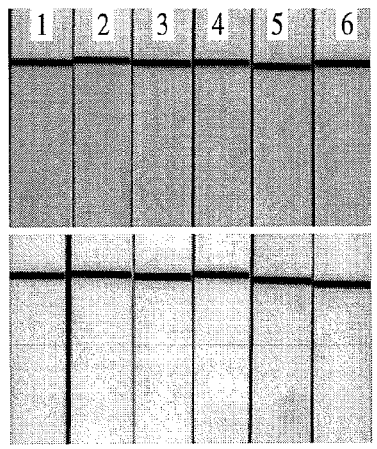
FIGS. 10A and 10B illustrate effects of background cleanup and various amounts of extraction buffer.
Figure 10B:
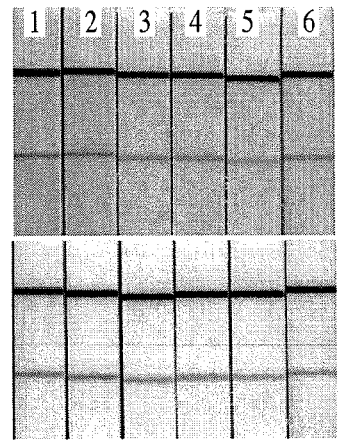

Data analysis of FIG. 9 with software Quantity One and visual read result

| Virus HA/test | Lane No. | Peak Intensity | Peak Intensity(avg) | Visual read |
|---|---|---|---|---|
| 0 | 1 | 2.2 | 2.18 | − |
|  | 2 | 2.2 |  |  |
| 0.021 | 3 | 2.8 | 2.78 | − |
|  | 4 | 2.7 |  |  |
| 0.041 | 5 | 4.8 | 4.67 | ± |
|  | 6 | 4.6 |  |  |
| 0.082 | 7 | 7.3 | 7.76 | + |
|  | 8 | 8.2 |  |  |
| 0.164 | 9 | 14.4 | 13.83 | + |
|  | 10 | 13.3 |  |  |

Values of peak intensity are the analysis result with Quantity One.

Values of peak intensity are the analysis results with Quantity One.

Example 4

Test the Detection Limit of Influenza A and B Test Using Fluorescent Europium Conjugate Materials: Wicking pad: 0.05% tween-20 treated polyester pad, 1.4 cm in width provided by Nanogen POC in Toronto, Canada; Absorbent pad: Ahlstrom Grade 222 paper, 3.5 cm in width, purchased from Fisher, Cat. # 2228-1212, lot# 6150502; Nitrocellulose Membrane Millipore HiFlow 135 membrane, 2.5 cm in width. Cat. No. SHF 1350425, Lot No. R68N46849, Code No. RK04414, roll No. 04OLI; Flu A membrane: 1.5 mg/ml anti-Flu A Medix 7304 antibody on test line and 1.5 mg/ml rabbit anti-mouse IgG on control line striped in Nanogen POC, Toronto, Canada; Anti-Flu A Fitzgerald M4090913—Europium conjugate at 1% beads concentration was prepared in Nanogen POC, Toronto, Canada; Flu B membrane: 1.5 mg/ml anti-Flu B Medix 9901 antibody on test line and 1.5 mg/ml rabbit anti-mouse IgG on control line striped in Nanogen POC, Toronto, Canada; Flu B membrane: 1.5 mg/ml anti-Flu B M2110171 antibody on test line and 1.5 mg/ml rabbit anti-mouse IgG on control line striped in Nanogen POC, Toronto, Canada; Anti-Flu B HyTest 2/3—Europium conjugate at 1% beads concentration was prepared in Nanogen POC, Toronto, Canada; Inactivated influenza A virus: Texas 1/77 (H3N2) from Microbix Biosystems, Inc. Cat.# EL-13-02, lot#13037A3; Inactivated influenza B virus: Hong Kong 5/72 from Microbix Biosystems Inc. Cat.# EL-14-03, lot# 14057A2; 3× extraction buffer containing 0.15 M Tris-Ct, pH 8.0, 2.25 M NaCl, 3%, BSA, 0.3% pluronic, 0.06% NaN3, 1.5% digested casein and 6 mM TCEP, was prepared in Nanogen, San Diego. Lot# 2232-001; Virus dilution buffer: 10M PBS with 1% BSA; Antibody-europium conjugate dilution buffer: 10 mM PBS, 1% BSA and 0.2% tween-20.

Protocols. Preparation of the lateral flow test strip: Nitrocellulose membrane striped with antibodies was laminated on a plastic card with 1-2 mm overlap between the wicking pad and at the end of the nitrocellulose strip with the absorbent pad. No cover tape was applied on any components. Strips were cut in 5 mm widths. Viruses dilution: Inactivated influenza A and influenza B positive controls were diluted to 409.6 HA unit/mL and 40.96 HA unit/mL, respectively for assay with the influenza test.

Antibody-Europium conjugate pretreatment; 1% Antibody-Europium conjugate was sonicated in a bath sonicator for 4 min. An amount of conjugated beads was then diluted to 0.04% with antibody-europium dilution buffer and sonicated for another 4 min.

Influenza A and B test procedure with antibody Europium conjugate: To 16.67 μL 3× Extraction Buffer in a test tube, add 5 mL 0.04% antibody-europium conjugate and different amount of virus. Add water to a final volume of 50 μL. Insert a lateral flow test strip in the assay solution, Wait 15 min at room temperature. Add 50 μL 1× extraction buffer to the same test tube. Wait for 5 min at room temperature. Place the lateral flow test strip in a tray and measure the fluorescence intensity. Each test condition was run with 5 replicates.

Figure 15:
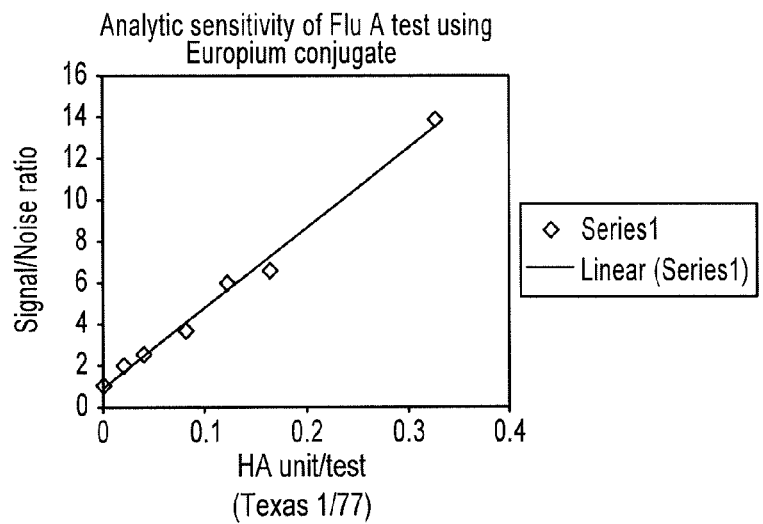
FIG. 15 illustrates the detection of influenza A using Europium conjugate.

Results: FIG. 15 Analytic sensitivity of Flu A test using Europium conjugate

TABLE 14

Statistic analysis of raw data for analytic sensitivity of Flu A test using Europium conjugate

| HA units | Replicates | | | | | AVG | CV |
| | 1 | 2 | 3 | 4 | 5 | | |
|---|---|---|---|---|---|---|---|
| 0 | 568 | 677 | 629 | 620 | 650 | 629 | 6.4% |
| 0.021 | 1350 | 1241 | 1256 | 1308 | 1216 | 1274 | 4.2% |
| 0.041 | 1777 | 1535 | 1727 | 1595 | 1364 | 1600 | 10.2% |
| 0.082 | 2171 | 2336 | 2438 | 2114 | 2336 | 2279 | 5.8% |
| 0.123 | 4176 | 3745 | 3558 | 3410 | 3765 | 3731 | 7.7% |
| 0.164 | 3989 | 3917 | 3963 | 4050 | 4489 | 4082 | 5.7% |
| 0.328 | 8866 | 9979 | 8497 | 8304 | 7783 | 8686 | 9.5% |

Figure 16:
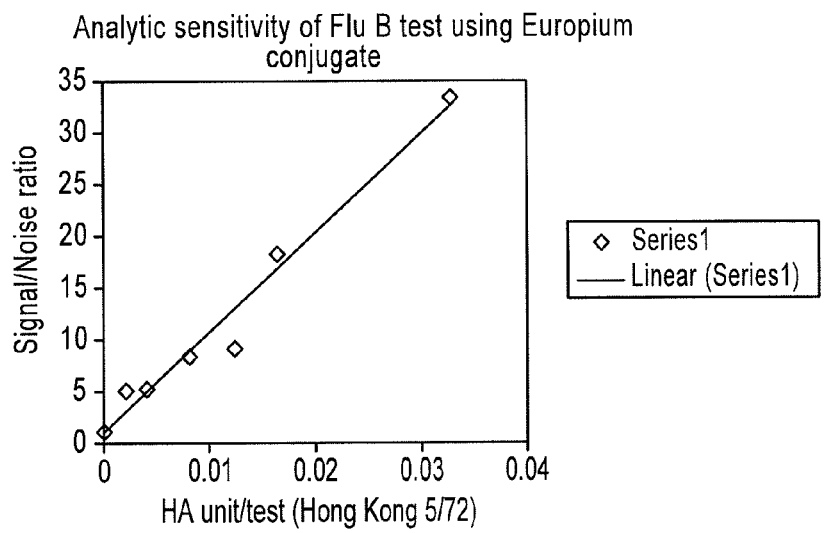
FIG. 16 illustrates the detection of influenza B using Europium conjugate.

FIG. 16 Test the analytic sensitivity of Flu B test using Europium conjugate and Medix 9901 on the membrane

TABLE 15

Statistic analysis of raw data for analytic sensitivity of Flu B test using Europium conjugate

| HA units | Replicates | | | | | AVG | CV |
| | 1 | 2 | 3 | 4 | 5 | | |
|---|---|---|---|---|---|---|---|
| 0 | 284 | 196 | 330 | 360 | 331 | 300 | 21.4% |
| 0.0021 | 1419 | 1361 | 1572 | 1600 | 1496 | 1490 | 6.8% |
| 0.0041 | 1430 | 1467 | 1611 | 1746 | 1626 | 1576 | 8.1% |
| 0.0082 | 2321 | 2520 | 2539 | 3312 | 1690 | 2476 | 23.4% |
| 0.0123 | 2580 | 2791 | 2661 | 2737 | 2781 | 2710 | 3.3% |

TABLE 15-continued

Statistic analysis of raw data for analytic sensitivity of Flu B test using Europium conjugate

| HA units | Replicates | | | | | AVG | CV |
|---|---|---|---|---|---|---|---|
| | 1 | 2 | 3 | 4 | 5 | | |
| 0.0164 | 5590 | 5111 | 5058 | 5639 | 5809 | 5441 | 6.2% |
| 0.0328 | 8699 | 10903 | 10047 | 10491 | 9796 | 9987 | 8.4% |

Figure 17:
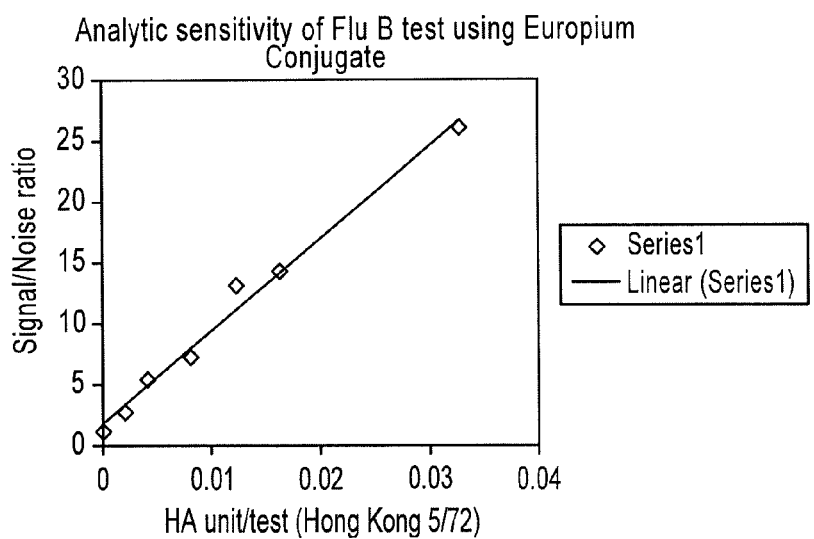
FIG. 17 illustrates sensitivity of Europium conjugate in detection of influenza B.
Figure 18:
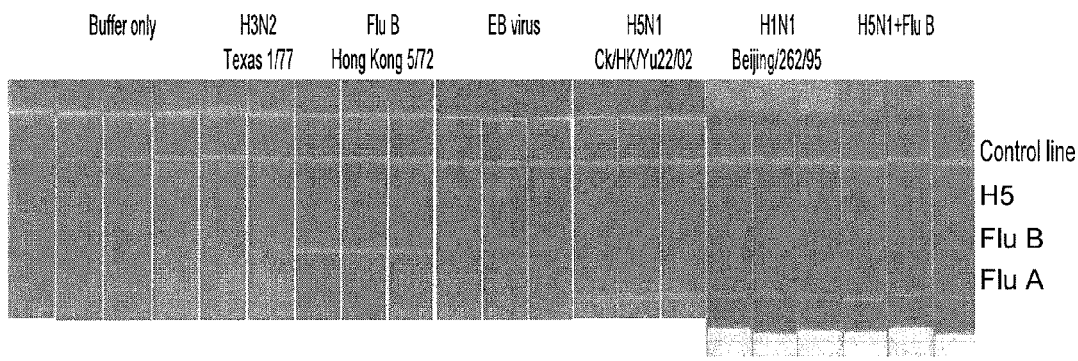
FIG. 18 illustrates strips tested with influenza A subtypes.
Figure 19:
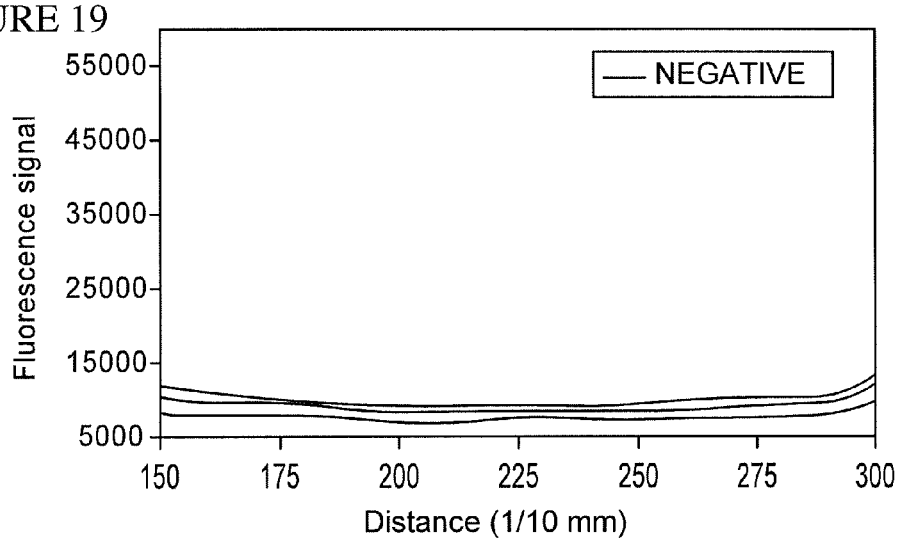
FIG. 19 illustrates buffer only control.
Figure 20:
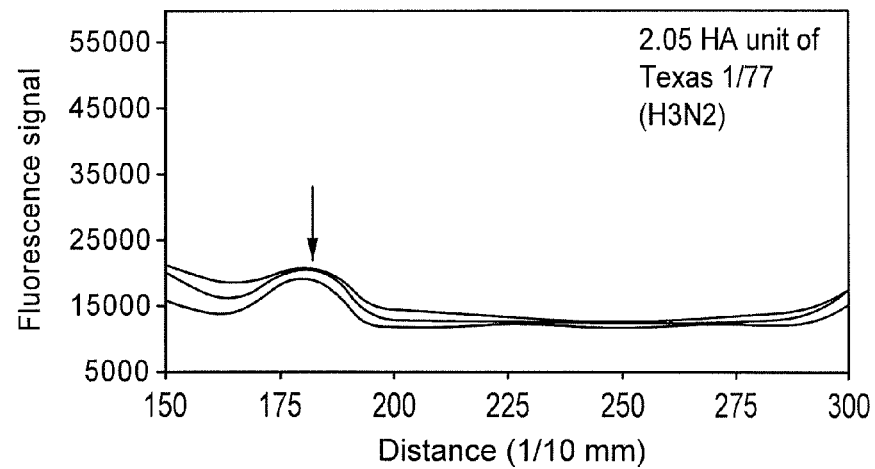
FIG. 20 illustrates test for influenza A and subtype H3N2.
Figure 24:
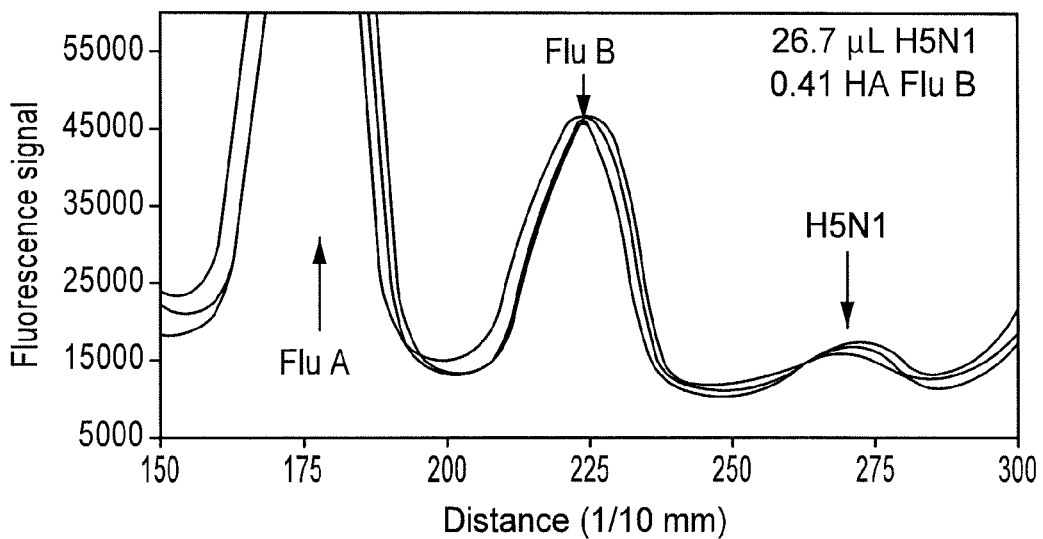
FIG. 24 illustrates test for influenza B and influenza A subtype H5N1
Figure 25:
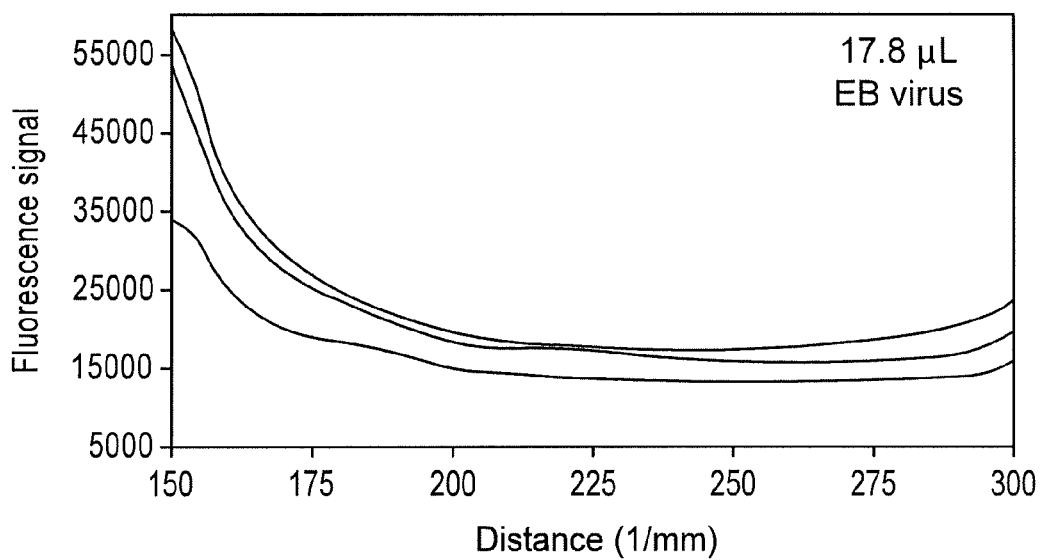
FIG. 25 illustrates test for Epstein-Barr virus

FIG. 17 Test the analytic sensitivity of Flu B test using Europium conjugate and M2110171 on the membrane

TABLE 16

Statistic analysis of raw data for analytic sensitivity of Flu B test using Europium conjugate

| HA units | 1 | 2 | 3 | 4 | 5 | AVG | CV |
|---|---|---|---|---|---|---|---|
| 0 | 511 | 501 | 532 | 481 | 446 | 494 | 6.6% |
| 0.0021 | 1368 | 1280 | 1458 | 1420 | 1395 | 1384 | 4.9% |
| 0.0041 | 2697 | 2535 | 2708 | 2677 | 2711 | 2666 | 2.8% |
| 0.0082 | 3412 | 3198 | 3817 | 3930 | 3609 | 3593 | 8.3% |
| 0.0123 | 6531 | 6560 | 6294 | 7290 | 6055 | 6546 | 7.1% |
| 0.0164 | 6707 | 7328 | 6679 | 6853 | 8098 | 7133 | 8.4% |
| 0.0328 | 12016 | 13162 | 12597 | 12907 | 13555 | 12847 | 4.5% |

Results: Table 5-7 show that the current market leader of rapid influenza immunoassay, the Quidel QuickVue Flu A+B test has a detection limit of 4.1 HA units for influenza A Texas 1/77 and 1.6 HA units for influenza B Hong Kong 5/72. When gold label is used, the present invention's influenza rapid test can detect at least 0.41 HA influenza A Texas 1/77 and 0.082 HA influenza B Hong 5/72 when limited assay volume and chasing buffer were used. This is 10 and 20 times more sensitive than Quidel's QuickVue Flu A×B in detecting influenza A Texas 1/77 and influenza B Hong Kong 5/72, respectively. By applying fluorescent Europium conjugate, the present influenza rapid test is able to detect as low as 0.021 HA unit of Influenza A Texas 1/77 with a Signal/noise (S/N) ratio of 2.03 and 0.0021 HA unit of Influenza B Hong Kong 5/72 with an S/N ratio of 4.96. If a S/N ratio of 2 is considered the limit of detection for the Europium based assay, Flu B would be able to detect down to 0.001 HA units/test. Or an improvement in sensitivity over the Quidel assay for Type B of about 1600 fold. This study clearly demonstrated that the improvements made to nitrocellulose assay technology does yield significant improvement in POC assay performance.

Example 5

Laboratory testing results to demonstrate preliminary proof of principle that influenza H5N1 can be differentiated from seasonal human influenza viruses using the proposed product design and instruments.

Materials: 3× Extraction Buffer containing 0.15 M Tris-Cl, pH 8.0, 2.25 M NaCl, 0.3% Pluronic F68, 3% BSA, 1.5% casein and 0.06% $NaN_3$, lot# 2232-001; 1× Extraction Buffer, lot# 2232-003; 0.2 M Tris(carboxyethyl)phosphine hydrochloride (TCEP), lot# 2232-078; Molecular Biology Water, lot# 318105; Europium dilution buffer, lot# RC 6-8-06; 10 mM PBS, pH 7.2 with 1% BSA, lot# HR 7-19-06; 1% HyTest 2/3 Europium conjugate with 0.025 mg antibody, lot# E2/3-270706-2; 1% M4090913 Europium conjugate with 0.025 mg antibody, lot# E13-270706-2; 1% 3C8 Europium conjugate with 0.1 mg antibody, lot#E3C8-180806; Nitrocellulose membrane striped with anti-Flu A A60010044P, anti-Flu B 9901, anti-H5 3G4 and rabbit anti-mouse antibody was prepared by Nanogen POC, Toronto, Canada. The antibody coating concentration was 2.0 mg/ml for all three test lines. The antibody coating concentration for the control line was 1.5 mg/ml. The distance between each test line, and test line and control line is 5 mm±0.5 mm; Wicking pad. 0.05% tween-20 treated polyester pad, 1.4 cm in width provided by Nanogen POC in Toronto, Canada; Absorbent pad: Ahlstrom Grade 222 paper, 3.5 cm in width, purchased from Fisher, Cat. # 2228-1212, lot# 6150502; Inactivated influenza A H1N1, Beijing/262/95 was purchased from NIBSC, 40 μg HA activity/ampoule: Inactivated influenza A H3N2, Texas 1/77 was purchased from Microbix Biosystems, Inc. lot#13037A3, 40960 HA/mL; Inactivated influenza H5N1, Ck HK Yu22/02 from Wantai at China; Inactivated influenza B, Hong>Kong 5/72 was purchased from Microbix, Biosystems, Inc., lot#14057A2, 40960 HA/mL; Epstein-Barr virus purchased from ATCC, VR-1491, strain B98-8, lot# 3605034

Procedures: Preparation of influenza test strips with multiple test line: Nitrocellulose membrane striped with antibodies was laminated on plastic card with 1-2 mm overlap with wicking pad and absorbent pad. No cover tape was applied on any components. Strips were cut in 5 mm in width; Inactivated influenza A H3N2, Texas 1/77 and influenza B, Hong Kong 5/72 were diluted 10 and 100 times, respectively, with 10 mM PBS/1% BSA; Inactivated H1N1 Beijing 262/95 was reconstituted with 1 mL $H_2O$; 1% antibody Europium conjugate was sonicated for 4 min with Branson 1210 bath sonicator. The individual conjugate was then diluted to 0.04% with Europium conjugate dilution buffer and sonicated 3 times with 4 min each time in ice bath. In some experiments, all three Europium conjugates were diluted together into the same tube. In this case, each antibody Europium conjugate concentration was still 0.04% bead; Assay preparation:

For each assay, following components were added to a tube: 16.67 μL 3× Extraction Buffer; 0.5 μL 0.2 M TCEP; 5 μL diluted Europium conjugate if all europium conjugate were diluted into the same tube or 15 μL Europium conjugate (5 μL each if individual Europium conjugate was diluted separately); Virus as indicated in the figures; Adjust the final volume to 50 μL with $H_2O$.

Test: Test was started by inserting the test strip into the assay solution. After 15 min, 50 μL 1× Extraction Buffer was added to the test tube and test was carried on for another 5 min. At 20 min, the result of test strip was read with a fluorescence reader. Each test was repeated 3 times.

Results: FIG. 18 influenza rapid test strip images under UV light after strips were tested with buffer, influenza A subtype H3N2, H1N1 and H5N1, influenza type B and Epstein-Barr virus.

FIG. 19 Test of influenza rapid test with buffer only

FIG. 20 Test of influenza rapid test with influenza A subtype H3N2, Texas 1/77

FIG. 21 Test of influenza rapid test with influenza type B

FIG. 22 Test of influenza rapid test with influenza A subtype H5N1, Ck/HK/Yu22/02

FIG. 23 Test of influenza rapid test with influenza A subtype H1N1 Beijing/262/95

FIG. 24 Test of influenza rapid test with H5N1 and influenza type B

FIG. 25 Test of influenza rapid test with Epstein-Barr virus

Results: Based on initial test results, antibodies have been selected for detecting influenza type A, type B and subtype H5. Strips with three different test lines that detected type A, type B and subtype H5, respectively, were prepared. The results in FIGS. 1-7 show that when Flu B is tested, only Flu B peak is observed. When either H1N1 or H3N2 is tested, only Flu A test peak is seen and peak corresponding to subtype H5 is not observed, Based one embodiment herein, another test line corresponding to H1 and H3 (together) will be striped on the membrane once anti-H1 and H3 antibodies are selected. Then another peak corresponding to H1/H3 will be also observed in addition to Flu A peak. When subtype H5N1 was tested, both Flu A peak and H5 peak are observed with the Flu A peak showing a stronger signal than the H5 peak. This result was expected as additional optimization of MAb selection and antibody loading and other factors within the assay are optimized. No cross-reaction of influenza test with EB virus was observed. These results clearly demonstrate that the approach discovered herein can yield multiple analyte test results without interference between the test lines.

The results shown above have clearly demonstrated that a new fully integrated POC technology that is highly sensitive and can independently detect different viral Types and subtypes on the same test strip has been discovered.

Example 6

Flu B Rapid Assay Using pRNA as Capture pRNA was fixed on the membrane to determine efficacy for capture of complimentary pRNA conjugated with anti-influenza B nucleoprotein antibody, in order to generate a signal when type B virus is present in the sample and an antibody-antigen-antibody complex is formed.

Materials: Wicking pad: 0.05% tween-20 treated polyester pad, 1.4 cm in width provided by Nanogen POC in Toronto, Canada; Absorbent pad: Ahlstrom Grade 222 paper, 3.5 cm in width, purchased from Fisher, Cat. # 2228-1212, lot# 6150502; Nitrocellulose Membrane: Millipore HiFlow 135 membrane, 2.5 cm in width. Cat. No. SHF1350425, Lot No. R68N46849, Code No. RK04414, roll No. 04OLI; Nitrocellulose membrane striped with 1.5 mg/ml M2110171, lot#M083106; Nitrocellulose membrane striped with 1.35 mg/ml 102a4-5G4, lot#MZ-42-74247-pRNA135; Anti-Flu B HyTest 2/3—Europium conjugate at 1% beads concentration was prepared in Nanogen POC, Toronto, Canada, lot#. E2/3-270706-3; Inactivated influenza B virus: Hong Kong 5/72 from Microbix Biosystems, Inc. Cat.# EL-14-03, lot# 14057A2; 3× extraction buffer containing 0.15 M Tris-Cl, pH 8.0, 2.25 M NaCl, 3% BSA, 0.3% pluronic, 0.06% NaN3, 1.5% digested casein and 6 mM TCEP, was prepared in Nanogen, San Diego. Lot# 2232-001; 0.2 M TCEP, lot# 2232-078; 1× Extraction Buffer, lot# 2232-003; Europium conjugate dilution buffer, lot# RC 6-8-06; Virus dilution buffer: 10 mM PBS with 1% BSA; 10 mM PBS, lot# SP09-22-06; Antibody-europium conjugate dilution buffer: 10 mM PBS, 1% BSA and 0.2% tween-20; Protein 5G4 for conjugation with pRNA that would be fixed on the membrane; Anti-Flu B nucleoprotein M2110171 was purchased from Fitzgerald, Bat# 578; pRNA 102a4-arm and 102b4-amn (both 13 mer) were synthesized and activated by PDITC.

Protocol:
Preparation of pRNA-Antibody Conjugates

TABLE 17

Calculation of amounts of oligo and antibodies required for conjugation.

| Oligo | | Conjugated with Antibody | Oligo/antibody Ratio | Antibody required |
|---|---|---|---|---|
| 102a4amn | 76.3 nmol | 5G4 | 10:1 | 1.15 mg |
| 102b4amn | 54.7 nmol | M2110171 | 5:1 | 1.64 mg |

Dissolve activated p A 102a4amn (total 229 mmol) and 102b4amn (total 164 mmol) in 150 µl of water in two separate tubes.
 a. Aliquot 50 µl into 3 microcentrifuge tubes for each pRNA and dry them using a spin vac.
 b. Place 1.5 mg of 5G4 monoclonal antibody into one spin filter and 2.0 mg M2110171 monoclonal antibody into another spin filter to concentrate both antibody. Antibodies were rinsed with 0.1 M sodium borate buffer. The final concentration of 5G4 and M2110171 were determined by the absorbance at 280 nm and were 33.35 mg/ml and 28.6 mg/ml, respectively
 c. Take 34 µL of concentrated 5G4 (1.15 mg) and 57 µL of concentrated M2110171. Bring the both volumes to 65 µL with 0.1 M borate buffer.
 d. Add each antibody to the corresponding pRNA and let reaction go for 15-20 hours at room temperature.
 e. pRNA-antibody conjugate was then purified with a Sephadex G-50 column with bed volume of 7 mL equilibrated with 0.01 M PBS.
1. Preparation of nitrocellulose membrane striped with 102a4-5G4
 Membrane was striped at NPOC at Toronto, See "Materials".
3. Preparation of the lateral flow test strip:
 Nitrocellulose membrane striped with antibody or 102a4-5G4 was laminated on a plastic card with 1-2 mm overlap with wicking pad at one end and 1-2 nun overlap with absorbent pad at the other end. Strips were cut in 5 mm widths.
4. Viruses dilution:
 Inactivated influenza B virus was diluted to 4.096 HA unit/mL with 0.01 M PBS and 1% BSA buffer.
Antibody Europium Conjugate Pretreatment
 1% anti-Flu B 2/3-Europium conjugate was sonicated in a bath sonicator for 4 min. An amount of 10 µL conjugated beads was then diluted to 0.02% with antibody-europium dilution buffer and sonicated for 20 sec. using a probe sonicator (Fisher Model 550) at power setting 2 for 4 pulses, 5 sec. each, with 10 sec. incubation in ice between each pulse.
 102b4-M2110171 (0.54 mg/ml after purification) was diluted to 0.1 mg/m with 10 mM PBS.
Assay Procedure
 Take 50 µL assay mixture and add it to a test tube. Insert a test strip into the assay mixture. Wait 15 min at room temperature. Add 50 µL 1× Extraction Buffer to the same test tube and incubate for another 5 minutes. Read the test strip with a LRE fluorescence reader
 a. Prepare assay mixture for strips with 102a4-5G4 striped

TABLE 18

| Components | Virus HA units/test | | | | | |
|---|---|---|---|---|---|---|
|  | 0 | 0.002 | 0.004 | 0..008 | 0.016 | 0.032 |
| 3 × buffer (µL) | 41.7 | 41.7 | 41.7 | 41.7 | 41.7 | 41.7 |
| Water (µL) | 52.1 | 50.8 | 49.6 | 47.1 | 42.1 | 32.1 |
| 0.2 M TCEP (µL) | 1.3 | 1.3 | 1.3 | 1.3 | 1.3 | 1.3 |
| 0.1 mg/ml 102b4-M2110171 pRNA conj. (µL) | 5.0 | 5.0 | 5.0 | 5.0 | 5.0 | 5.0 |
| 0.02% 2/3 Europium conj. (µL) | 25.0 | 25.0 | 25.0 | 25.0 | 25.0 | 25.0 |
| Flu B virus 4.096 HA units/ml (µL) | 0.0 | 1.3 | 2.5 | 5.0 | 10.0 | 20.0 |
| Total vol. for 2.5 tests (µL) | 125.0 | 125.0 | 125.0 | 125.0 | 125.0 | 125.0 | b. Prepare assay mixture for strips striped with anti-Flu B antibody M2110171

TABLE 19

| Components | Virus HA units/test | | | | | |
|---|---|---|---|---|---|---|
| | 0 | 0.002 | 0.004 | 0..008 | 0.016 | 0.032 |
| 3 × buffer (μL) | 41.7 | 41.7 | 41.7 | 41.7 | 41.7 | 41.7 |
| Water (μL) | 57.1 | 55.8 | 54.6 | 52.1 | 47.1 | 37.1 |
| 0.2 M TCEP (μL) | 1.3 | 1.3 | 1.3 | 1.3 | 1.3 | 1.3 |
| 0.02% 2/3 Europium conj. (μL) | 25.0 | 25.0 | 25.0 | 25.0 | 25.0 | 25.0 |
| Flu B virus 4.096 HA units/ml (μL) | 0.0 | 1.3 | 2.5 | 5.0 | 10.0 | 20.0 |
| Total vol. for 2.5 tests (μL) | 125.0 | 125.0 | 125.0 | 125.0 | 125.0 | 125.0 |

Result

FIG. 30 A: Raw signals of test strips with 102a4-5G4 conjugate on.

Table 20. Net peak height of signals showed in FIG. 30A

TABLE 16

| HA units/test | 1 | 2 | AVG | Signal/Noise |
|---|---|---|---|---|
| 0 | 360.0 | 331.9 | 345.9 | 1.0 |
| 0.002 | 521.1 | 447.1 | 484.1 | 1.4 |
| 0.004 | 682.0 | 783.3 | 732.7 | 2.1 |
| 0.008 | 1048.5 | 916.2 | 982.4 | 2.8 |
| 0.016 | 1799.0 | 1594.3 | 1696.7 | 4.9 |
| 0.032 | 2745.4 | 3257.2 | 3001.3 | 8.7 |

Figure 30B:
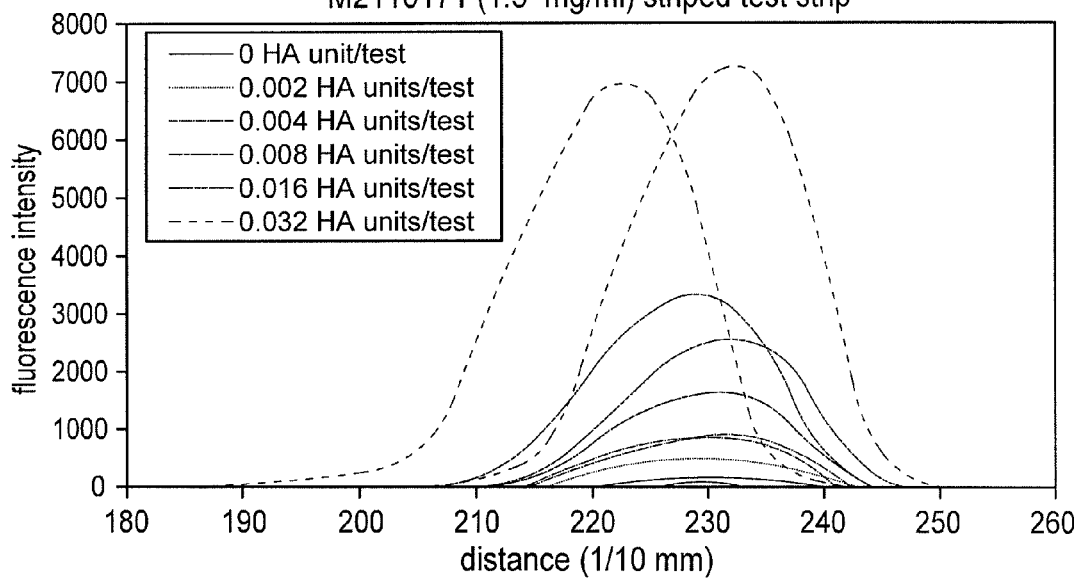

FIG. 30B: Raw signals of test strips with antibody M2110171 on.

TABLE 21

| Net peak height of signals showed in FIG. 30B | | | | |
|---|---|---|---|---|
| HA units/test | 1 | 2 | AVG | signal/noise |
| 0 | 155.1 | 142.6 | 148.8 | 1.0 |
| 0.002 | 495.8 | 538.8 | 517.3 | 3.5 |
| 0.004 | 884.2 | 895.9 | 890.0 | 6.0 |
| 0.008 | 1633.7 | 1698.0 | 1665.8 | 11.2 |
| 0.016 | 3329.4 | 2574.9 | 2952.2 | 19.8 |
| 0.032 | 7203.1 | 6974.3 | 7088.7 | 47.6 |

Figure 31:
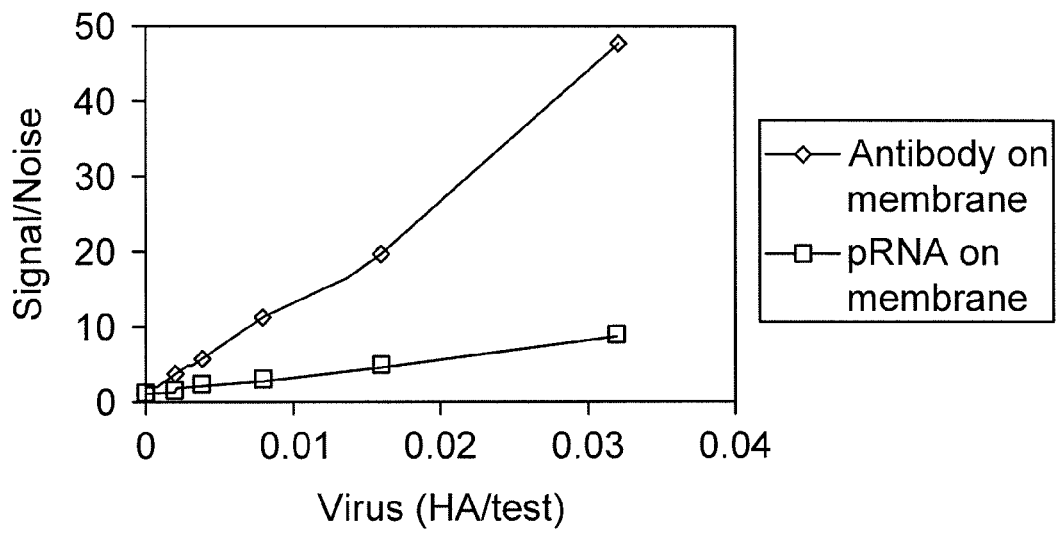
FIG. 31 illustrates a comparison of sensitivity using pRNA and antibody.

FIG. 31 Compare the sensitivity of two Flu B test strips.

The data clearly indicates that 1) pRNA conjugated with a protein, such as 5G4 antibody in this case, can be fixed on the nitrocellulose membrane; 2) pRNA can hybridize with a complementary oligo conjugated with an antibody on the nitrocellulose membrane; 3) the analyte specific antibody is still functioning after conjugated with pRNA. The result has demonstrated that a specific pair of pRNA can be used as a capture system in lateral flow rapid assay.

Example 7

Reader Europium Detection

Six different reference concentrations of Europium were used to test a reader (note the following numerical references correspond to references utilized in figures: (1) $5 \times 10^{-6}$ M; (5) $5 \times 10^{-5}$ M; (3) $5 \times 10^{-5}$M; (6) $5 \times 10^{-4}$M; (2) $5 \times 10^{-4}$M and (4) $5 \times 10^{-3}$M. Europium was encased in acrylic and different sized blocks were cut to provide different concentrations. Measurements are provided as for counts per meters $\times 10^{-4}$ FIG. 33.

Figure 34A:
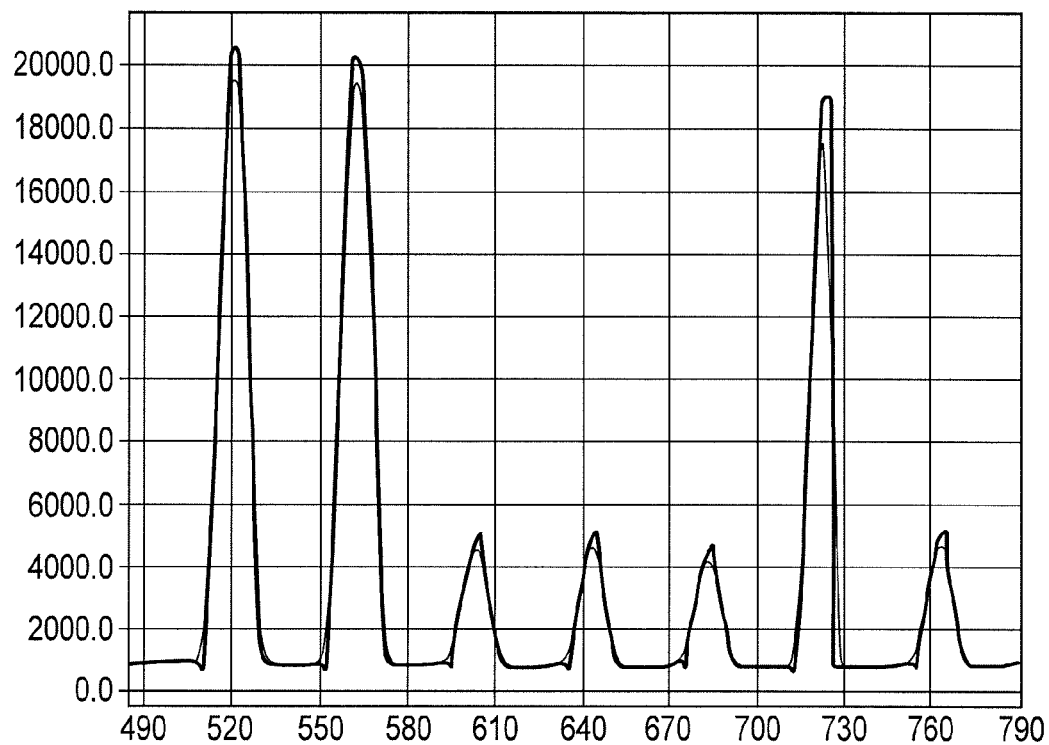
FIG. 34. Hard Standards; (A) provides a graph for 7 different hard standards as read by an UV LED reader; (B) provides a Test Device with multiple windows through which the signal is detected when the Test Device is placed in a reader.
Figure 34B:
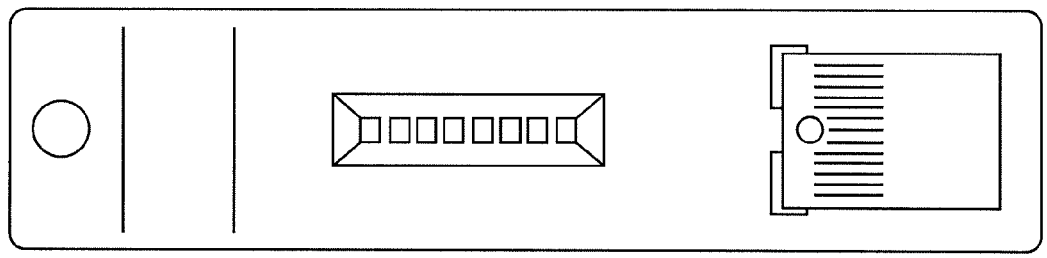
Figure 37:
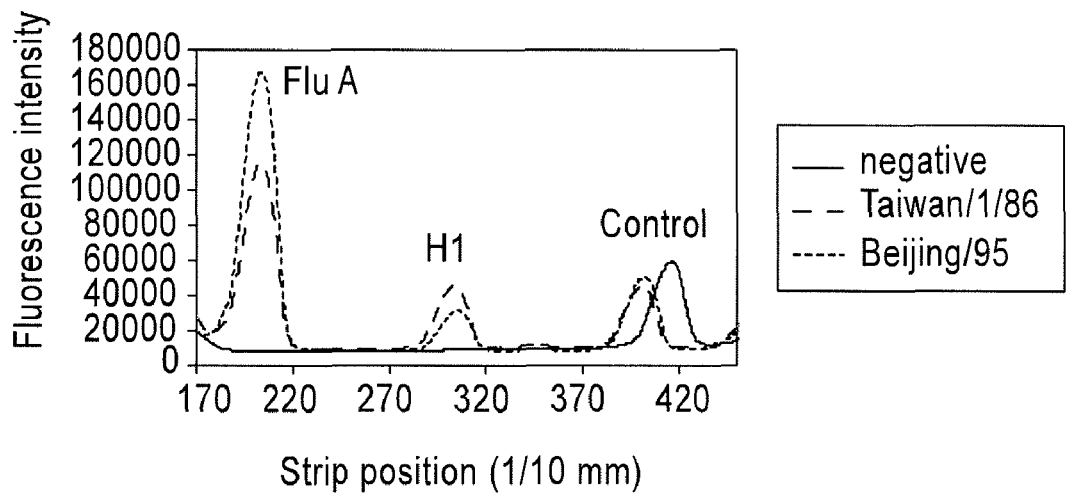
FIG. 37 depicts a graph of fluorescence intensity of subtype H1N1 viruses.
Figure 38:
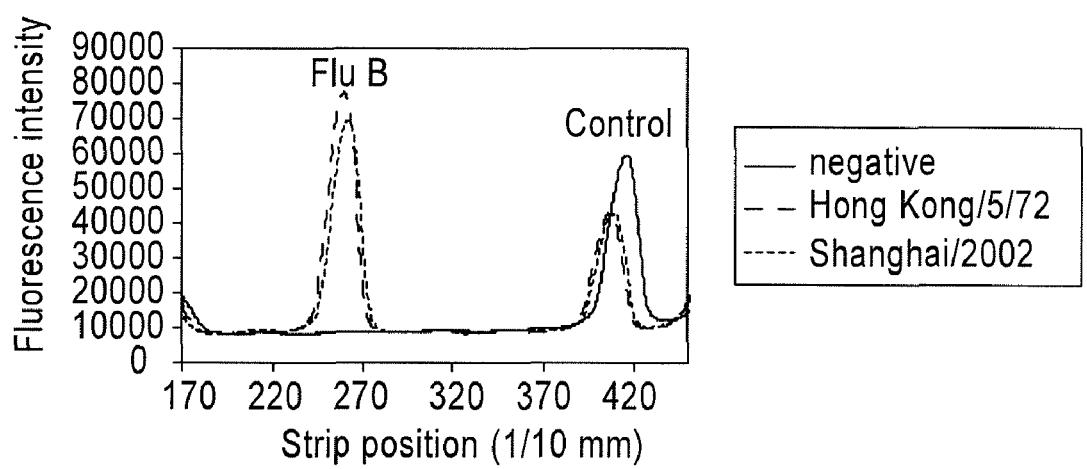

In another example, seven (7) 1 mm wide Europium hard standards pieces were mounted on 4 mm centers FIG. 34.

Example 8

Archive Sample

Influenza Viruses: Inactivated Influenza A/Texas 1/77 (H3N2) at 40960 HA units/μL from Microbix Biosystems, Inc. of Ontario, Canada, catalog number EL-13-02; and inactive Influenza B/Hong Kong 5/72 at 40960 HA units/mL from Microbix Biosystems, Inc. of Ontario, Canada, catalog number EL-14-03.

Viral RNA Transcript Positive Controls; Influenza A RNA Control, PN: 606161, LiN: RRH2174P73 at 50,000 copies/μL; and Influenza B RNA Control, PN: 606162, LN: RH2174P73 at 50,000 copies/μL Extraction Buffer: 3× Extraction Buffer The table below lists the formulation of the 3× Extraction Buffer and the corresponding part number, lot number and vendor of each of the components

TABLE 22

| Component | Concentration | Vendor | Catalog Number | Lot Number |
|---|---|---|---|---|
| Trizma Base | 150 mM | Sigma | T-6791 | 58H5431 |
| BSA | 3% | SeraCare Life Science | AP-4500 | 013-05-015 |
| Pluronic F68 | 0.3% | Pragmatics Inc. | Code 025 | WPMS-561B |
| Casein | 1.5% | Sigma | C5890 | 075K0108 |
| NaN$_3$ | 0.06% | Sigma | S8032 | 125K2502 |
| NaCl | 2.25 M | Sigma | S7653 | 075K0024 |

Tris(2-carboxyethyl)phosphine hydrochloride (TCEP) 200 mM, made on 7-6-06 by HR, powder ordered from PIERCE, Product Number: 20491, Lot Number:GL 102548

Prepare fresh 1× Extraction Buffer: Combine 200 μL of 3× Extraction Buffer with 6 μL of 0.2 M TCEP and 394 μL of water to make 600 μL of 1× Extraction Buffer. The formulation of the 1× Extraction Buffer is: 50 nm r Tris, 1% BSA, 0.1% Pluronic F68, 0.5% Casein, 0.02% NaN3, 0.75 M NaCl and 2 mM TCEP.

Sample binding and storage materials: Whatman FTA Elute Micro Card, Cat.#WB120401, LN: FE6231106; Whatman Harris UNI-CORE 2.00 mm Punch, Cat. # WB640001, LN: 6023; and MicroAmp Reaction Tubes with Caps 0.2 mL, PN: N801-0540, LN: P34H4QA11, ABI Elution materials: Distilled water, DNAse, RNAse free, Cat. # 10977-015, LN: 1317578, Invitrogen Heat source: GeneAmp PCR System 9700, AB1, QA2126 RT and PCR reagents and material:

TABLE 23

| Component | Vendor | Catalog Number | Lot Number |
|---|---|---|---|
| RT Mix | Prodesse | GLS01 | 050105RM |
| MgCl$_2$ 1M | Ambion | 9530G | 064R37A |
| MulV Reverse Transcriptase, 50 u/μL | ABI | N808-0018 | H03264 |
| RNase Inhibitor, 20 u/μL | ABI | N808-0119 | H05526 |
| RVA Primer Mix | Nanogen | Not available | RH2174P100 |
| AmpliTaq Gold Polymerase, 5 u/μL | ABI | N808-0249 | G03670 |
| 96 Well PCR Reaction Plate | ABI | 4306737 | P03F6QA41 |

Materials for evaluating RT-PCR reactions: Agilent DNA 4000 Reagents: PN. 5067-1504, LN: 0623; and Agilent DNA Chips: PN 5067-1522, I.N: JA21BK01

Methods

Preparation of RT Master Mix

TABLE 24

| Component | Volume per reaction (µL) |
|---|---|
| RT Mix | 11 |
| 1M MgCl$_2$ | 0.1 |
| MulV Reverse Transcriptase (50 u/µL) | 1 |
| RNase Inhibitor (20 u/µL) | 1 |
| DNAse, RNAse Free Water | 1.9 |
| Total | 15 |

Add 15 µL of RT master mix into a well in 96 well PCR plate

TABLE 25

Preparation of PCR Master Mix

| Component | Volume per reaction (µL) |
|---|---|
| RVA Primer Mix | 39.5 |
| AmpliTaq Gold Polymerase (5 u/µL) | 0.5 |
| Total | 40 |

Add 40 µL of the PCR master mix into a well in 96 well plate

TABLE 26

Dilution of RNA Positive Controls: Dilute Influenza A and Influenza B RNA with DNase, RNase free water as described in the table below

| Start Conc. (copies/µL) | End conc. (copies/µL) | Dilution Factor | µL RNA | µL water | Total Volume | Copies/rxn | Remain Volume |
|---|---|---|---|---|---|---|---|
| 50,000 | 20,000 | 2.5 | 8 | 12 | 20 | N/A | 10 |
| 20,000 | 2000 | 10 | 10 | 90 | 100 | 10000 | 90 |
| 2000 | 200 | 10 | 10 | 90 | 100 | 1000 | 90 |
| 200 | 20 | 10 | 10 | 90 | 100 | 100 | 90 |
| 20 | 2 | 10 | 10 | 90 | 100 | 10 | 100 |

Add 5 uL of diluted RNA into proper RT reaction

TABLE 27

Dilution of Influenza A and Influenza B inactive viruses with 1 × Extraction Buffer

| Start Conc. (HA units/µL) | End Conc.(HA units/µL) | Dilution Factor | µL virus | µL of 1 × Extraction Buffer | Total Volume | HA units/ disc | Remain Volume |
|---|---|---|---|---|---|---|---|
| 40.96 | 4.096 | 10 | 5 | 45 | 50 | 20.5 | 45 |
| 4.096 | 0.4096 | 10 | 5 | 45 | 50 | 2.05 | 45 |
| 0.4096 | 0.04096 | 10 | 5 | 45 | 50 | 0.2 | 45 |
| 0.04096 | 0.004096 | 10 | 5 | 45 | 50 | 0.02 | 45 |
| 0.004096 | 0.0004096 | 10 | 5 | 45 | 50 | 0.002 | 50 |

Application of samples to ETA Elute Card:

Apply 5 µL of following samples onto the sample area of the Whatman FTA Elute Micro Card; 1× Extraction Buffer as a control; Virus diluted with 1× Extraction Buffer; Air dry the FTA Elute Card for 15-20 min. at room temperature; punch out a 5 to 6 mm diameter disc with the punch from the area that the sample was applied to then place in a 0.2 mL Micro-Amp reaction tube; and elute RNA from FTA Elute disc: Add 150 µL of water into the tube containing the disc and vortex 3× for 5 seconds; remove water by using a sterile pipette tip; repeat addition/removal of water once; centrifuge for 5 seconds, then pipette off the excess liquid; add 50 µL of water, heat at 65° C. for 30 min. then vortex the tubes for 5 seconds; and take out 5 µL of the liquid and add to the appropriate well of the 96 well RT plate.

RT-PCR Assay
Thermal cycler program for RT Step

| Temperature (° C.) | Time (minutes) | Number of Cycles |
|---|---|---|
| 22 | 10 | 1 |
| 42 | 60 | 1 |
| 95 | 5 | 1 |
| 4 | Hold | — |

Transfer 10 µL of the completed RT reaction to the appropriate PCR well containing PCR master mix. Pipette up and down to mix.

TABLE 28

Thermal cycler program for PCR Step

| Temperature (° C.) | Time | Number of Cycles |
|---|---|---|
| 95 | 10 minutes | 1 |
| 95 | 60 seconds | 2 |
| 55 | 30 seconds | |
| 72 | 45 seconds | |
| 94 | 60 seconds | 38 |
| 60 | 30 seconds | |
| 72 | 30 seconds | |
| 72 | 7 minutes | 1 |
| 4 | Hold | — |

Evaluate PCR reactions for amplicon using Agilent Bioanalyzer
RT-PCR Agilent Results: The no template control reactions did not generate any detectable amplicon.
RNA positive controls

TABLE 29

| | Influenza A | | | Influenza B | | |
|---|---|---|---|---|---|---|
| Copies/rxn | band size | ng/µL | Pos/Rxn | band size | ng/µL | Pos/Rxn |
| 10K | 233 bp | 17.33 | 3/3 | 242 bp | 18.28 | 2/2 |
| 1K | 233 bp | 11.57 | 5/5 | 245 bp | 16.96 | 3/3 |
| 100 | 233 bp | 3.84 | 3/3 | 246 bp | 10.62 | 2/2 |
| 10 [1] | 236 bp | 0.30 | 3/3 | 246 bp | 4.08 | 2/2 |

The observed band sizes of Influenza A and Influenza B RNA Positive Controls are of the correct size.

TABLE 30

| | Influenza Viruses | | | | | |
|---|---|---|---|---|---|---|
| HA units/ | Influenza A | | | Influenza B | | |
| disc | band size | ng/µL | Pos/Rxn | band size | ng/µL | Pos/Rxn |
| 20 | 229 bp | 17.39 | 2/2 | 246 bp | 12.31 | 2/2 |
| 2 | 229 bp | 5.83 | 2/2 | 247 bp | 3.02 | 2/2 |
| 0.2 | 230 bp | 2.34 | 2/2 | 247 bp | 7.25 | 2/2 |
| 0.02 | 230 bp | 0.34 | 1/2 | 247 bp | 3.06 | 2/2 |
| 0.002 | Not detected | Not available | 0/2 | 244 bp | 1.08 | 2/2 |

Conclusion: Successfully detected RNA from lysed Influenza types A and B viruses using the Whatman FTA Elute Card and RT-PCR amplification.

The assay detected down to 0.2 HA units/disc of Influenza type A virus and 0.002 HA units/disc of Influenza type B virus.

The Whatman FTA Elute Card can be used to archive viral RNA for later testing in an RT-PCR assay for the detection of Influenza types A and B.

Example 9

Multi-analyte Detection

To demonstrate proof of principle that multianalyte Influenza diagnostic test can differentiate Influenza H5N1 from seasonal flu a rapid and high sensitivity assay was developed and compared with traditional lateral flow tests using colored latex bead or colloidal gold.

A lanthanide label was utilized where latex microbeads filled with Europium chelate, combined with a wash buffer demonstrated improved sensitivity. Seasonal Influenza (in this example, Influenza Type B) was clearly differentiated from avian flu H5N1 using membrane striped directly with anti-Flu A, anti-Flu B and anti-H5 antibodies at different zones on the test strip.

The data demonstrates that using pRNA and direct striping of MAb on to the nitrocellulose as the capture systems on the same lateral flow test strip, is able to separately detect influenza A subtype H1N1 and H5N1 as well as Type B and Type A nucleoprotein on different test zones on a single Nitrocellulose test strip. A table summarizing the areas of the assay that were exercised in this study are is shown below.

TABLE 31

Proof of Concept Table:

| Assay Component | Description |
|---|---|
| Nitrocellulose membrane blocked with hydrolyzed casein | Millipore 135 membrane, same material as currently used by Operations, the size is different |
| Wicking pad treated with Tween | Standard Operations component |
| Absorbent pad | Material same as used in operations, size is different |
| Backing card | Material same as used in operations, size is different |
| Extraction Buffer | Designed to lyse and inactivate influenza |
| Mucolytic Agent | Designed to reduce viscosity of mucus on the specimen swab |
| Wash Buffer | Similar formulation to extraction buffer, designed to "wash" unbound Eu latex beads from the test strip and reduce background and "stop" the assay |
| Type A MAb striped onto Nitrocellulose directly | Showing feasibility of directly spotting MAb in combination with pRNA |
| Type A MAb conjugated to Europium Latex microbeads | Conjugate the MAb directly to the Eu microbeads |
| Type B MAb Pair striped onto nitrocellulose directly | Showing feasibility of directly spotting MAb in combination with pRNA |

TABLE 31-continued

Proof of Concept Table:

| Assay Component | Description |
|---|---|
| Type B MAb conjugated to Eu Microbeads | See comment under Type A above |
| H1N1 MAb conjugated to a specific pRNA | Demonstrating and showing proof of concept that pRNA oligos can be used as a generic capture agent in the assay. |
| H1N1 MAb conjugated to Biotin | Conjugate the MAb to biotin and react the conjugate with Streptavidin coated Eu beads. |
| H5N1 MAb conjugated to a specific pRNA | Demonstrating and showing proof of concept that pRNA oligos can be used as a generic capture agent in the assay. |
| H5N1 MAb conjugated to Eu | See comment under Type A above |
| Europium latex microbeads coated with Streptavidin and reacted with H1N1 | Developed a procedure to react Europium latex beads coated with Streptavidin with a specific MAb conjugated with biotin. After the reaction excess free biotin is added to block the reaction sites. |
| Europium latex microbeads coated with Streptavidin and reacted with anti-H1 MAb | See comment above |
| Europium latex microbeads coated with individual MAbs | See comments above |
| Reader | The reader will have optics better suited to the UV LED light source and with filters to eliminate background light emission, to improve the performance of the system. |
| Assay regent, single solution (mixture of extraction reagent, mucolytic agent, trehalose, buffer agents, Europium latex beads with conjugated/bound detection reagents and capture reagents with detection and capture reagents | This will enable confirming the design with all assay reagents mixed together. |
| Four unique analyte test lines plus a control line | The assay demonstrated four separate functioning analyse test lines |

Materials

1. Preactivated pRNAs were provided by Nanogen Bothell development team.
   a. 102a10 (10 mer), lot# 825-079A
   b. 102b10 (10 mer, the complimentary pRNA of 102a10), lot# 825-065D, lot# S25-065D
   c. 3a10 (10 mer), lot# 825-079C
   d. 3b10 (10 mer, the complimentary pRNA of 3a10), lot# 825-065F, lot# 825-065F
2. Antibody
   a. Anti-Flu A 7304 from BiosPacific
   b. Anti-Flu A M4090913 from Fitzgerald
   c. Anti-Flu B 2/3 from HyTest
   d. Anti-Flu B M2110171 from Fitzgerald
   e. Anti-influenza H1 M322210 from Fitzgerald
   f. Anti-influenza H1 8252 K from Chemicon
   g. Anti-influenza H5 10F7 from Xiamen University
   h. Anti-influenza H5 3G4 from Xiamen University
3. OptiLink Carboxylate-Modified Microparticles (Europium beads)
   Europium beads with 0.3 □M diameter was purchased from ThermoFisher Scientific (Seradyn). Cat.# 83470750010250, manufacture lot# C020512, package lot# 201154.
4. Virus
   Influenza B Hong Kong/5/72 from Microbix, B/Shanghai/2002 from Dr. Bovian's laboratory, A/Taiwan/1/86 (H1N1) from NIBSC, A/Beijing/95(H1N1) provided by Dr. Bovian's laboratory, Bar-headed GS/QH/15/2005 (H5N1) and DK/VNM/568/2005 (H5N1) from Dr. Guan's laboratory in Hong Kong University.
5. Three (3)×Extraction buffer containing 150 mM Tris-Cl, pH 8.0, 2.25 M NaCl, 3% BSA, 1.5% digested casein, 0.3% pluronic F68 and 0.15% ProClin 300, lot# 2277-038.
6. solution: 0.2 M Tris(2-carboxyethylphosphine) hydrochloride solution, lot# 2277-067.
7. Recombinant Streptavidin.
8. Non-specific antibody 5G4 for conjugation with pRNA, prepared by Nanogen Toronto facility and used to strip onto the nitrocellulose.
9. Strip backing card, 0.1" super white polystyrene from G&L
10. Absorbent pad, filter paper grade 222 from Alstrom filtration
11. Wicking pad, 0.05% Tween-20 treated polyester pad.

Procedure

Preparation of Antibody-Europium Conjugate 1.1 Antibodies M4090913, 2/3, and 3G4 were conjugated with 0.3 □M Europium beads by ThermoFisher Scientific (Seradyn).

1.2 Antibody 8252 k Europium conjugate was prepared through an indirect procedure by combining biotinylated 8252K with streptavidin coated Europium microparticles. Biotinylated 8252K and streptavidin Europium microbeads were prepared at the Nanogen Toronto facility. Streptavidin Europium stock at 1% solid was sonicated with a bath sonicator for 5 min. It was then diluted to 0.02% with Europium conjugate dilution buffer and sonicated with a probe sonicator for 20 s. Biotinylated 8252 k was diluted to 10 µg/ml with PBS buffer. Aliquot of 5 µL was added to each tube. Aliquot of 5 µL 0.02% solid streptavidin Europium conjugate was then quickly mixed with biotinylated 8252K. The conjugate was blocked using 2.5 uL of 100 mM Biotin. The 8252 k Europium conjugate was then directly used in the assay.

2. Preparation of antibody-pRNA conjugate: All the antibodies were concentrated to approximately 20 mg/ml using Microcon 50 from Amicon. The buffer was change to 0.1 M sodium borate, pH 9.0. Aliquot of 1 mg non-specific antibody 5G4 was added to tubes containing 33.5 nmol pre-activated pRNA 102b10 or 3b10 (dry powder). Aliquot of 0.5 mg M322210 and 0.5 mg 10F7 were added to tubes containing 16.7 nmol pre-activated pRNA 102a10 and 3a10, respectively. The reaction was carried out for 15 hours at room temperature. The antibody pRNA conjugate was purified with a Sephadex G-50 column equilibrated with 10 mM PBS buffer, pH 7.0. Two peaks were resolved, the first peak with conjugate and second peak with unactivated pRNA (confirmed by HPLC, data not shown).

3. Preparation of nitrocellulose membrane striped with four test lines. For this membrane, anti-Flu A 7304 and anti-Flu B M2110171 at 1.5 mg/ml were striped directly for test line "A" and test line "B", respectively. Conjugate 102b10-5G4 and 3b10-5G4, both at 0.75 mg/ml, were striped for "H1" and "H5" test line. The control line was striped with 0.5 mg/ml rabbit anti-mouse antibody. All lines were 5 rum apart. The membrane was then blocked with a solution containing 0.35% PVP, 0.25% Triton X-100 and 0.5% digested casein, and cured at 37° C.

4. Preparation of test strip Nitrocellulose membrane striped with 4 test lines and one control line was laminated onto the backing card and has 1-2 mm overlap with treated polyester pad and absorbent pad. Strips were cut into 5 mm widths using a Kinematic 2360 strip cutter 5. Test procedure. Assay mixture was prepared as following. To a test tube, add 16.7 μL 3× Extraction Buffer, 0.5 μL 0.2 M TCEP, 0.1 μg 102a10-M322210 conjugate, 0.1 μg 3a 10-10F7 conjugate, antibody Europium conjugate and different viruses. The final concentration of all antibody Europium conjugates is 0.002% solid in a final volume of 50 μL. Test was started by inserting test strip into the assay mixture. After 15 min, another 50 μL of 1× Extraction Buffer was added to wash the strip. Strips were read with a fluorescence reader at 20 min.

Results.

TABLE 32

The following table compares the signal/noise ratio of different test peaks when tested with different viruses.

| | | Signal/noise of each test line | | | |
|---|---|---|---|---|---|
| Virus | Description | H5 | H1 | B | A |
| H5 | Bar Headed GS/QH/15/2005 | 116.9 | 2.0 | 0.6 | 245.7 |
| | DK/VNM/568/2005 | 122.0 | 5.7 | 1.0 | 606.9 |
| H1 | Taiwan/1/86 | 8.5 | 63.8 | 0.4 | 492.7 |
| | Beijing/95 | 6.4 | 44.4 | 0.5 | 896.5 |
| Flu B | Hong Kong 5/72 | 3.5 | 1.3 | 437.1 | 4.8 |
| | Shanghai/2002 | 2.0 | 1.2 | 376.0 | 3.9 |

The data clearly shows that the test system is able to differentiate multiple analytes. In this example, the analytes detected included seasonal influenza subtype H1N1, Flu B from avian flu H5N1 with a good Type A signal. In this test, two pairs of pRNA were used as the capture system to differentiate H1 test line from H5 test line. Some low reactivity was observed at the H1 test line position when H5 viruses were tested indicating small amount of hybridization of pRNA 3a10 conjugated on anti-H5 antibody with 102b10 striped on test line H1. No false positive reaction effects were observed on the H5 specific test line when subtype H1N1 viruses were tested.

In addition, this report clearly shows that the assay, shows good reactivity, good separation of analyte signals when a single multi-analyte reaction mix is used for all test specimens. In addition, the assay can detect all appropriate analytes when testing a single test specimen at moderate viral loads simultaneously.

Conclusion: Results demonstrate that with virus of multiple subtypes and strains significant separation of the signals for each analyte for each viral strain or subtype tested is achieved (FIGS. 36-38). To ensure the results had validity two separate strains of each subtype were tested. Furthermore, the results clearly demonstrate that a pRNA generic capture system to apply to the H1 and H5 detection systems, thus enabling utilization of the pRNA capture system for additional panels of different analytes.

Moreover, the assay can readily be adapted to incorporate additional analyte-specific binding agents. Further, device/assays of the invention can be utilized in methods of screening different analytes. For example, a large number of Anti-H3 expressing clones are can be screened to determine .

Of course the devices/methods of the invention can be utilized to screen new viral strains (an important example is the new Fujan like strain). For example, as new MAb to new strains of the H5N1 subtype are obtained, they can be incorporated in the SCD and Test Device of the invention for screening.

The results shown above have clearly demonstrated that a new fully integrated assay technology that is highly sensitive and can independently detect different viral Types and subtypes on the same test strip has been discovered. Further such assay can be administered in a Point-of-Care setting.

Example 10

Multianalyte Detection: Marker Proteins

The device and methods of the invention may also be used to detect various analytes associated with a disease condition or nutritional state, or any other associative characteristics. For example, multiple cardiac markers may be detected and/or quantified:

(1) The Troponin marker: Capture Antibody is a polyclonal rabbit anti-Troponin-I and conjugated to a specific pRNA sequence (SEQ ID NO: 92). Detection antibody is a mixture of two mouse MAbs and conjugated to biotin and reacted with streptavidin coated 0.3 u Europium latex microparticle.

(2) The CK/MB marker. Capture antibody is a Polyclonal Goat and is conjugated to specific pRNA sequence (SEQ ID NO: 93). Detection antibody is also a MAb and is conjugated to biotin and reacted with streptavidin coated 0.3 u Europium latex microparticles.

(3) The Myoglobin marker: Capture antibody is a Rabbit anti Myoglobin Polyclonal and is conjugated to specific pRNA sequence (SEQ ID NO: 94). Detection antibody is also a MAb and is conjugated to biotin and reacted with streptavidin coated 0.3 u Europium latex microparticle.

(4) Control line made up of rabbit anti mouse.

Therefore, the multianlyte "point of care" assay system can quantitate each of the markers individually in a single assay format as outlined above and as follows:

Using the reader with a hard Europium standard (a Europium standard locked in acrylic and yields a uniform reading under a uniform set of conditions over a long period of time) which ensures the reader is able to meet fluorescent signal intensity requirements reproducibly. Thus each analyte can be quantitated independently

Example 11

Multianalyte Detection: Viruses

As disclosed herein above, the devices of the invention can also be configured to detect multiple different viruses, or different subtypes of a virus. For example, the devices of the invention can be configured to provide an influenza multianalyte plus RSV qualitative assay where multiple analytes can be detected from a single specimen:

(1) Influenza Type A: Capture antibody is a MAb and is conjugated to specific pRNA sequence (SEQ ID NO: 93); Detection antibody is also a MAb and is conjugated to biotin and reacted with streptavidin coated 0.3u Europium latex microparticles (2) Influenza Type B: Capture antibody is a monoclonal mouse MAb and is conjugated to a specific pRNA sequence (SEQ ID NO: 94); Detection antibody is also a MAb and is conjugated to biotin and reacted with streptavidin coated 0.3 u Europium latex microparticles.

(3) Influenza H1 and H3: Capture antibodies are MAb specific for H1 and H3 Hemagglutinin and are all conjugated to specific pRNA sequence (SEQ ID NO: 95); Detection antibody is also a MAb and is conjugated to biotin and reacted with streptavidin coated 0.3u Europium latex microparticles.

(4) Influenza H5: Capture antibody is a monoclonal mouse MAb and is conjugated to specific pRNA sequence (SEQ ID NO: 96); Detection antibody is also a MAb and is conjugated to biotin and reacted with steptavidin coated 0.3 u Europium latex microparticles.

(5) RSV: Capture antibody is a monoclonal mouse MAb and is conjugated to specific pRNA sequence (SEQ ID NO: 97); Detection antibody is also a MAb and is conjugated to biotin and reacted with streptavidin coated 0.3 u Europium latex microparticles.

(6) Control Line: Capture antibody is rabbit anti-mouse and binds to the MAb on the Europium latex microparticle.

Example 12

Expression of Single Chain Antibodies of 10F7 and 4D1 and Test of Their Activities.

The variable region genes of the heavy and light chains of each antibody were linked with a nucleic acid encoding a short peptide (GGGGS(SEG ID NO:114)) to form the DNA fragment encoding a single chain antibody, Use 10F7 VHF/10F7 VHR as the primer pair to amplify the variable region DNA fragment of 10F7 heavy chain. Use 10F7VKF/10F7 VKR as the primer pair to amplify the variable region DNA fragment of 10F7 light chain. Use 4D1 VHF/4D1 VHR as the primer pair to amplify the variable region DNA fragment of 4D1 heavy chain. Use 4D1 VKF/4D1 VKR as the primer pair to amplify the variable region DNA fragment of 4D1 light chain.

Use 10F7 VHF/10F7 VKR as primers to amplify the overlapping 10F7 single chain DNA fragment. Use 4D1 VHF/4D1 VKR as primers to amplify the overlapping 4D1 heavy chain DNA fragment. The amplified DNA fragments were recovered, digested with BamH I and Sal I, and cloned into prokaryotic expression vector pTO-T7 digested with the same restriction enzymes. Using ER2566 *E. coli* as host cells, the single chain antibody proteins were expressed using standard methods. The expressed proteins were in the form of insoluble inclusion bodies. The inclusion bodies were broken up by ultrasound treatment, and the resulting sediments were purified using standard methods, The purified sediments were dissolved in 8M urea. The urea solution was dialyzed slowly in 1×PBS solution, centrifuged at 12000 rpm for 10 min to remove the remaining sediments. The final purified single chain antibody solution was tested for activities.

Select 26 strains of H5N1 viruses to test the activities of the above purified 10F7 and 4D1 single chain antibodies using HI assay as described above. The concentration of 10F7 single chain antibody is used at 1.06 mg/ml. The concentration of 4D1 single chain antibody is used at 0.34 mg/ml. The 4D1 single chain antibody exhibits HA inhibition activity against 23 of the virus strains. The 10F7 single chain antibody shows HA inhibition activity against 14 of the virus strains (Table 33 below).

TABLE 33

HA inhibition activities of the three single chain antibodies against the 25 H5N1 viruses.

| H5N1 Virus Strains | ScFv | | |
|---|---|---|---|
| | 4D1 | 10F7 | 8H5 |
| A1 | >8 | >8 | 3.5 |
| A2 | >8 | >8 | 4.5 |
| A3 | >8 | >8 | 3.5 |
| A5 | >8 | >8 | 4 |
| A6 | 7 | 7.5 | 3 |
| A7 | 6 | 6.5 | 3 |
| A8 | >8 | 6 | 2.5 |
| B1 | >8 | 7 | 4 |
| B2 | 0 | 0 | 0 |
| B3 | >8 | >8 | 5 |
| B4 | >8 | >8 | 5 |
| B5 | 0 | 0 | 0 |
| B6 | >8 | 7 | 3.5 |
| B7 | >8 | 7 | 4 |
| B8 | >8 | 7 | 3 |
| C2 | >8 | 2 | 1 |
| C3 | >8 | 1 | 0 |
| D1 | >8 | 2.5 | 2.5 |
| D2 | 7.5 | 2.5 | 2 |
| E1 | 1 | 0 | 0 |
| E2 | 1 | 0 | 0 |
| F2 | 5 | 0 | 0 |
| F3 | 3 | 0 | 0 |
| G1 | 3.5 | 0 | 0 |
| H1 | 6 | <1 | 0 |
| H2 | 4 | 0 | 0 |

HI titer is diluted by the "n"th power of 2. "n" is the numbers shown in the table.

The activity of the above purified 10F7 single chain antibody was tested using the neutralization method. 7 virus strains that were isolated from chicken, duck and various wild birds in Hong Kong, Indonesia, Qinghai and other areas during the period from 2002 to 2006 were used to test the activity of 10F7 using the 141 assay. The antibody showed good neutralization activity against 5 of the virus strains (Table 34). At 64 times of dilution, the antibody was still able to inhibit virus infection of host cells.

TABLE 34

10F7 single chain antibody neutralization test results.

| Virus strain | dilution of 10F7 scFv |
|---|---|
| CK/HK/Yu22/02 | 64 |
| DK/IDN/MS/04 | 16 |
| CK/IDN/2A/04 | 32 |
| BhGs/QH/15/05 | 16 |
| CK/HK/213/03 | <1 |
| CP Heron/HK/18/05 | 8 |
| Oriental Magpie Robin/HK/366/2006 | <1 |

Example 13

Detection of 7aa Peptides Activities

The three bacteriophages containing the 7aa peptides of 8H5A, 5H5E and 3C8A were amplified in large numbers. They were dissolved in PBS after being precipitated with PEG. Phage titer was between $10^{11}$ and $10^{12}$. Microplates were pre-coated with monoclonal antibodies 8H5, 4A 1, 9N7 and 4D11 at 5 µg/ml. The plates were blocked with PBS containing 5% milk. The three bacteriophages were serially diluted; and added to the plates. The reaction was carried on for 1 hr. Then the plates were washed for 5 times. 1:5,000 diluted mouse anti-M13/HRP antibody (Amersham Phamarcia Biotech, UK) was added as the secondary antibody and incubated for 0.5 hr. The results were read after the reaction was completed. The results are shown in Table 35 below, which demonstrated that the specific reactions between the peptide 8H5A and the monoclonal antibody 8H5 were good, and the specific reactions between 8H5A and the other three monoclonal antibodies were weak. The specific reaction between 8H5E and monoclonal antibody 8H5 was relatively poor.

TABLE 35

Detection results of the specific binding activity of 7aa Peptides to monoclonal antibodies

| Monoclonal Antibody | 8H5A (1:1000) | 8H5E (1:1000) |
|---|---|---|
| 8H5 | 0.559 | 0.25 |
| 4A1 | 0.158 | 0.142 |
| 9N7 | 0.062 | 0.065 |
| 4D11 | 0.118 | 0.078 |

Example 14

MAB Capture System vs. pRNA Capture System Using Nanogen Influenza A Test

To compare the sensitivity of Nanogen Influenza A Test using 2 different capture systems and to compare the pRNA capture system using 2 different test strips Procedure for cutting test strips: Prepare the membrane card by placing absorbent pad (3.5 cm wide) and Tween-20 pre-treated; precut polyester wicking pad (1.4 cm wide) on the adhesive side with 1 mm overlap with the membrane, striped with appropriate antibody. Cut this prepared card into 5 mm wide test strips with a paper cutter Virus Dilution: Dilute Influenza A/Texas/1/77 40960 HA units/mL virus with 1% BSA in PBS according to the following dilution scheme.

TABLE 36

Dilution Scheme for Flu A Virus

| Start conc. (HA units/mL) | dilution factor | Start vol. (µL) | 1% BSA in PBS vol. (µL) | End vol. (µL) | End conc. (HA units/mL) |
|---|---|---|---|---|---|
| 40960 | 1:100 | 1 | 99 | 100 | 409.6 |
| 409.6 | 1:10 | 50 | 450 | 500 | 40.96 |
| 40.96 | 1:10 | 20 | 180 | 200 | 4.096 |

Europium Dilution: Dilute 17-10-06-1 europium conjugate to 0.02% using the europium dilution buffer; 245 µL of europium dilution buffer+5 µL of 1% stock. Sonicate the diluted europium conjugate using a probe sonicator (Fischer Model 550) at power setting of 3, total time 20 seconds (10 sec on time and 5 sec off time).

pRNA Conjugate dilution: Dilute 102a10-7304 (0.39 mg/ml) conjugate to 0.1 mg/ml with 10 mM PBS, pH 7.2; 37.2 µL of PBS+12.8 µL of 102a10-7304 conjugate.

Assay Procedure: Prepare the assay mixtures according to the following tables

TABLE 37

Assay Mix for the MAB capture system

| | 4.096 HA units/ml | | | | 40.96 HA units/ml | |
|---|---|---|---|---|---|---|
| | HA units/test | | | | | |
| | 0 | 0.01 | 0.02 | 0.04 | 0.1 | 1 |
| 3 × extraction buffer (µL) | 41.75 | 41.75 | 41.75 | 41.75 | 41.75 | 41.75 |
| 0.2 M TCEP (µL) | 1.25 | 1.25 | 1.25 | 1.25 | 1.25 | 1.25 |
| 0.02% europium conj. (µL) | 12.5 | 12.5 | 12.5 | 12.5 | 12.5 | 12.5 |
| Flu A virus (µL) | 0 | 6.25 | 12.5 | 25 | 6.25 | 62.5 |
| water (µL) | 69.5 | 63.25 | 57 | 44.5 | 63.25 | 7 |
| Total vol. for 2.5 test (µL) | 125 | 125 | 125 | 125 | 125 | 125 |

TABLE 38

Assay Mix for the pRNA capture system

| | 4.096 HA units/ml | | | | 40.96 HA units/ml | |
|---|---|---|---|---|---|---|
| | HA units/test | | | | | |
| | 0 | 0.01 | 0.02 | 0.04 | 0.1 | 1 |
| 3 × extraction buffer (µL) | 83.5 | 83.5 | 83.5 | 83.5 | 83.5 | 83.5 |
| 0.2 M TCEP (µL) | 2.5 | 2.5 | 2.5 | 2.5 | 2.5 | 2.5 |
| 0.02% europium conj. (µL) | 25.0 | 25.0 | 25.0 | 25.0 | 25.0 | 25.0 |
| Flu A virus (µL) | 0.0 | 12.5 | 25.0 | 50.0 | 12.5 | 125.0 |
| 0.1 mg/mL 102a10-7304 conj. (µL) | 5.0 | 5.0 | 5.0 | 5.0 | 5.0 | 5.0 |
| water (µL) | 134.0 | 121.5 | 109.0 | 84.0 | 121.5 | 9.0 |
| Total vol. for 5 tests (µL) | 250.0 | 250.0 | 250.0 | 250.0 | 250.0 | 250.0 |

TABLE 39

| | Materials | | |
|---|---|---|---|
| | Material | Lot | Note |
| 1 | Absorbent Pad: Grade 222, 12 IN × 12 IN | 6150502 | cat # 2228-1212 |
| 2 | Wicking Pad: Tween 20 Pre-treated Polyester Pad | 06PPP0157C | Grade 6613 |
| 3 | Anti-flu A Medix 7304 (1.5 mg/ml) membrane | 310806 | |
| 4 | 102b10-5G4 striped membrane | 131206-2-1 | conc. 0.75 mg/ml, w/o blocking |
| 5 | 102b10-5G4 striped membrane | 131206-2-2 | conc. 0.75 mg/ml/w/ 0.5% casein (toronto) blocked |
| 6 | 3× Extraction Buffer | 2271-001 | DOM Nov. 15, 2006 |
| 7 | 1× Extraction Buffer | 2232-003 | DOM Nov. 15, 2006 |
| 8 | 0.2 M TCEP | 2232-180 | DOM Nov. 9, 2006 |
| 9 | Molecular Biology Water | 1347929 | CAT # 10977-015, GIBCO |
| 10 | 1% BSA in 0.10 M Phosphate Buffered Saline | 2271-036 | DOM Dec. 14, 2006 |
| 11 | Flu A/Texas/1/77 virus @ 40960 HA units/mL | 13037A3 | CAT # EL-13-02 |
| 12 | Europium dilution buffer | N/A | DOM Jun. 8, 2006 by Roy Chung |
| 13 | Europium conjugate with M4090913 | 17-10-06-1 | Prepared by Philip Lam |
| 14 | 102a10-7304 pRNA conjugate | 2271-028-2 | DOM Dec. 8, 2006, conc. 0.39 mg/ml |
| 15 | 10 mM PBS pH 7.2 | 2271-035 | DOM Dec. 14, 2006 |

Incubate 7304 (1.5 mg/mL) test strips with MAB CAPTURE SYSTEM assay mix.

Incubate 102b10-5G4 (0.75 mg/mL) w/o blocking, and w/0.5% casein blocked test strips with pRNA CAPTURE SYSTEM assay mix.

Run the experiment in duplicates.

Let it stand at room temperature for 15 min.

Add 50 μL of 1× extraction buffer to the same tube to wash the test strips.

After 5 min, read the test strips using a fluorescence reader.

RESULTS

TABLE 40

Figure 39:
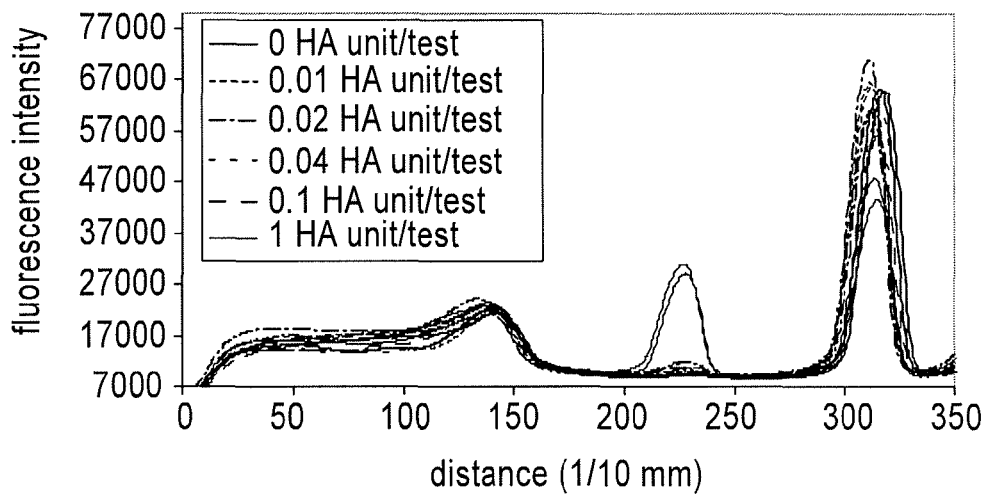

MAB capture system (See FIG. 39)

| HA units/test | 0 | 0.01 | 0.02 | 0.04 | 0.1 | 1 |
|---|---|---|---|---|---|---|
| 1 | 528.1 | 793.7 | 935.7 | 1421.6 | 2550.1 | 21111.3 |
| 2 | 569.6 | 776.0 | 1037.5 | 1440.0 | 2395.4 | 19961.8 |
| AVG | 548.8 | 784.9 | 986.6 | 1430.8 | 2472.8 | 20536.5 |
| S/N | | 1.4 | 1.8 | 2.6 | 4.5 | 37.4 |

Figure 40:
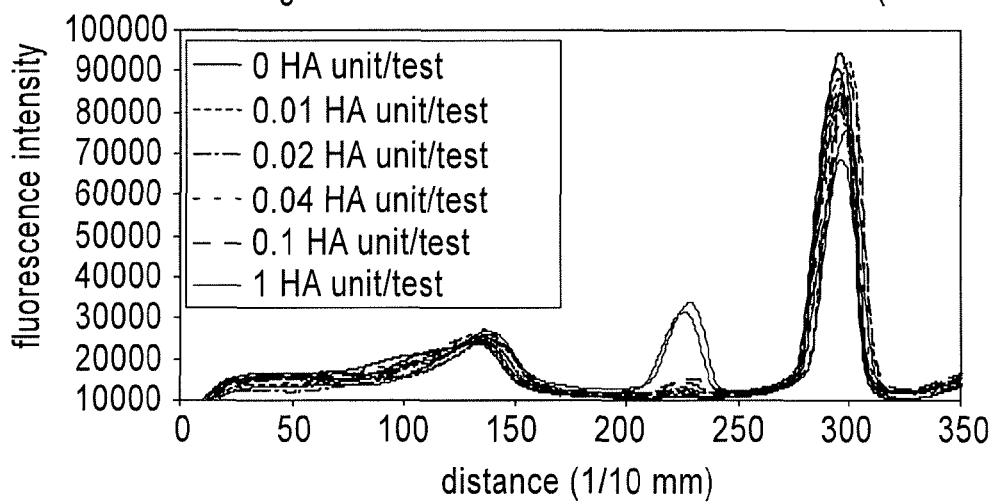

TABLE 41 pRNA capture system with 0.75 mg/ml membrane blocked with 0.5% casein (See FIG. 40)

| HA units/test | 0 | 0.01 | 0.02 | 0.04 | 0.1 | 1 |
|---|---|---|---|---|---|---|
| 1 | 114.6 | 434.1 | 703.0 | 1360.9 | 3222.7 | 21209.1 |
| 2 | 222.6 | 628.5 | 804.6 | 1385.1 | 2891.4 | 19440.1 |
| AVG | 168.6 | 531.3 | 753.8 | 1373.0 | 3057.1 | 20324.6 |
| S/N | | 3.2 | 4.5 | 8.1 | 18.1 | 120.5 |

Figure 41:
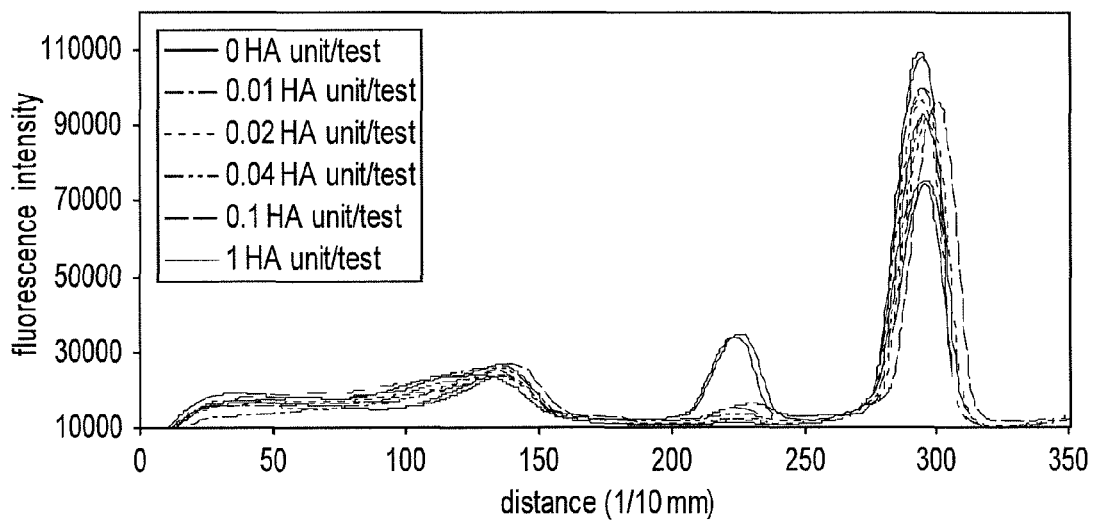
Figure 42:
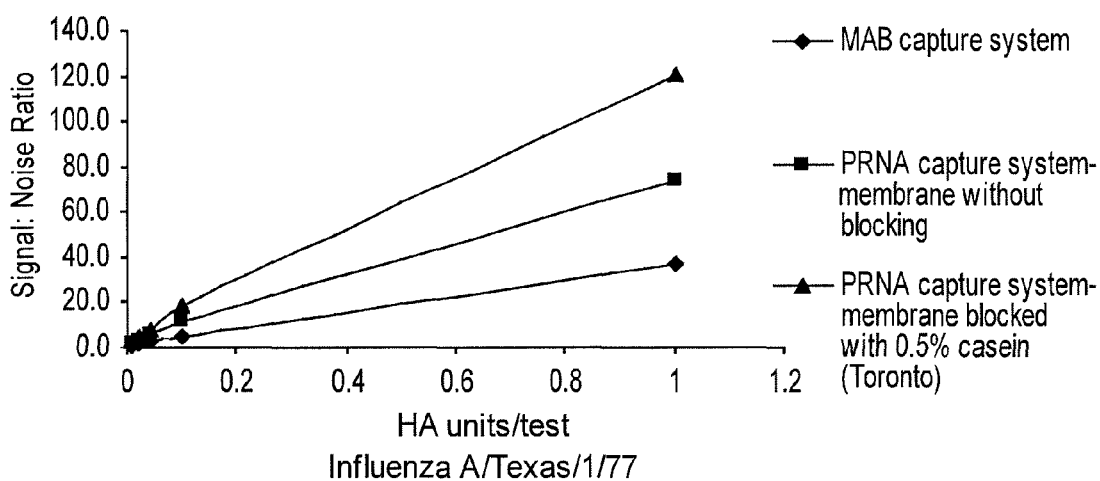

TABLE 42 pRNA capture system with 0.75 mg/ml membrane without blocking (See FIG. 41)

| HA units/test | 0 | 0.01 | 0.02 | 0.04 | 0.1 | 1 |
|---|---|---|---|---|---|---|
| 1 | 284.4 | 737.9 | 940.0 | 1880.4 | 3336.0 | 22387.5 |
| 2 | 318.1 | 612.2 | 814.6 | 1471.3 | 3560.8 | 22383.6 |
| AVG | 301.3 | 675.1 | 877.3 | 1675.9 | 3448.4 | 22385.6 |
| S/N | | 2.2 | 2.9 | 5.6 | 11.4 | 74.3 |

Conclusion: As the data indicates the sensitivity of the test is highest with pRNA capture system when used with test strips blocked with 0.5% casein from Toronto with a single to noise ration of 120 with 1 HA unit but using direct spotting of MAb onto the test strip the SR ratio was only 37.4 indicating the pRNA capture system significantly improved the sensitivity of the assay system.

```
SEQ ID NO: 1 8H5 Vh Nucleotide sequence
caggttcagc tgcagcagtc tggagctgag ccgatgaagc ctggggcctc agtgaagata tcctgcaagg ctactggcta cactttcagt aactactgga tagagtggat aaagcagagg cctggacatg gccttgagtg gattggagag attttacctg gaagcgatag aacaaactac aatgggaagt tcaagggcaa ggccacattc actgcagata catcctccaa cacagcccac atgcaactca gtagcctgac atctgaggac tctgccgtct attactgtgc aaatagatac
```

```
gacgggtatt attttggttt ggattactgg ggtcaaggaa cctcagtcgc cgtctcctca
gcc

SEQ ID NO: 2
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
                20                  25                  30

Trp Ile Glu Trp Ile Lys Gln Arg Pro Gly His Gly Leu Glu Trp Ile
            35                  40                  45

Gly Glu Ile Leu Pro Gly Ser Asp Arg Thr Asn Tyr Asn Gly Lys Phe
        50                  55                  60

Lys Gly Lys Ala Thr Phe Thr Ala Asp Thr Ser Ser Asn Thr Ala His
65                  70                  75                  80

Met Gln Leu Ser Ser Leu Thr Ser Glu Asp Ser Ala Val Tyr Tyr Cys
                85                  90                  95

Ala Asn Arg Tyr Asp Gly Tyr Tyr Phe Gly Leu Asp Tyr Trp Gly Gln
            100                 105                 110

Gly Thr Ser Val Ala Val Ser Ser Ala

SEQ ID NO: 3 8H5 Vk Nucleotide sequence
gaaatcgtgc tcacccagtc tccagcaatc atgtctgcat ctctagggga aaggtcacc atgagctgca gggccagctc aagtgtaaat ttcgtttact ggtaccagca gaggtcagat gcctccccca actattgatt tactattca ccaacctgg ctcctggagt cccacctcgc ttcagtggca gtgggtctgg gaactcttat tctctcacaa tcagcggctt ggagggtgaa gatgctgcca cttattactg ccagcacttt actagttccc cgtacacgtt cggagggggg accaacctgg aaataaaacg g SEQ ID NO: 4 8H5 Vk Amino Acid sequence
Gln Ile Val Leu Thr Gln Ser Pro Ala Ile Met Ser Ala Ser Leu Gly
1               5                   10                  15

Gln Lys Val Thr Met Ser Cys Arg Ala Ser Ser Ser Val Asn The Val
                20                  25                  30

Tyr Trp Tyr Gln Gln Arg Ser Asp Ala Ser Pro Lys Leu Leu Ile Tyr
            35                  40                  45

Tyr Ser Ser Asn Leu Ala Pro Gly Val Pro Arg Pro Ser Gly Ser
        50                  55                  60

Gly Ser Gly Asn Ser Tyr Ser Leu Thr Ile Ser Gly Leu Gln Gly Gln
65                  70                  75                  80

Asp Ala Ala Thr Tyr Tyr Cys Gln His Phe Thr Ser Ser Pro Tyr Thr
                85                  90                  95

Phe Gly Gly Gly Thr An Leu Glu Ile Lys Arg
            100                 105

SEQ ID NO: 5 3C8 Vh Nucleotide sequence
cagatccagt tggtgcagtc tggacctgag ctgaagaagc ctggagagac agtcaagatc tcctgcaagg cctctgggta cagcttcaca aactatggaa tgaactgggt gaagcaggct ccaggaaagg gtctaaagtg gatgggctgg ataaacacct acaccggaga gccagcctat gctgatgact tcaagggacg gcttgccttc tctctggaaa cctctgccag cactgcctat ttgcagatca caaccctcaa aaatgaggac acggctacat atttctgtgc aagatggaat agagatgcta tggactactg gggtcaagga acctcggtca ccgtatctag c SEQ ID NO: 6 3CB Vh Amino Acid sequence
Gln Ile Gln Leu Val Gln Ser Gly Pro Glu Leu Lys Lys Pro Gly Glu
1               5                   10                  15
```

-continued

```
Thr Val Lys Ile Ser Cys Lys Ala Ser Gly Tyr Ser Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Ala Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Asn Arg Asp Ala Met Asp Tyr Trp Gly Gln Gly Thr Ser
            100                 105                 110

Val Thr Val Ser Ser
        115

SEQ ID NO: 7 3CB VK Nucleotide sequence
gacattgtgc tgacccaatc tccagcttct ttggctgtgt ctcttgggca gagggccacc atatcctgca gagccagtga agtgttgat agttctgaca atagtcttat gcactggtac cagcagaaac aggacagcc acccaaactc ctcatctatc gtgcatccaa cctagaatct gggatccctg ccaggttcag tggcagtggg tctaggacag acttcaccct caccattaat cctgtggagg ctgatgatgt tgcaacctat tactgtcagc aaagtattgg ggatcctccg tacacgttcg gaggggggac caagctggaa ataaaacgg SEQ ID NO: 8 3CB VK Amino Acid sequence
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Ser
            20                  25                  30

Asp Asn Ser Leu Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Ile
                85                  90                  95

Gly Asp Pro Pro Tyr Thr Phe Gly Gly Gly Thr Lys Leu Glu Ile Lys
            100                 105                 110

Arg

SEQ ID NO: 9 10F7 Vh Nucleotide sequence
caggtccaac tgcagcagcc tggggctgaa cttgtgaagc ctggggcttc agtgaagctg tcctgcaagg cttctggcta caccttcacc agctactgga tgcactgggt gaagcagagg cctggacagg gccttgagtg gatcggagag attgatcctt ctgattctta ctactaactac aatcagaagt tcaagggcaa ggccacattg actgtagaca atcctccag cacagcctac atgcagctca gcagcctgac atctgaggac tctgcggtct attactgcgc aagggggggt acaggagact tcactatgc tatggactac tggggtcaag gcacctcggt caccgtatca tcg SEQ ID NO: 10 10F7 Vh Amino Acid sequence
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

```
Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Gly Asp Phe His Tyr Ala Met Asp Tyr Trp Gly
            100                 105                 110

Gln Gly Thr Ser Val Thr Val Ser Ser
        115                 120

SEQ ID NO: 11 - 10F7 VK Nucleotide sequence
gacatcctga tgacccaatc tccatcctcc atgtctgtat ctctgggaga cacagtcagc atcacttgcc atgcaagtca gggcattagc agtaatatag gtggtcgca gcagaaacca gggaaatcat ttaagggcct gatctatcat ggaaccaact tggaagatgg agttccatca aggttcagtg gcagtggatc tggagcagat tattctctca ccatcagcag cctggaatct gaagattttg cagactatta ctgtgtacag tatgttcagt tcccgtacac gttcggaggg ggcaccaagc tggaaatcaa acgg SEQ ID NO: 12 10F7 VK Amino Acid sequence
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
                20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Val Gln Phe Pro Tyr
                85                  90                  95

Thr Phe Gly Gly Gly Thr Lys Leu Glu Ile Lys Arg
            100                 105

SEQ ID NO: 13. Artificial sequence/Unknown Organism
catgggatgc tgccggtgta t

SEQ ID NO: 14. Artificial Sequence/Unknown Organism
aattctgggc cttggctgac g

SEQ ID NO: 15. Artificiai Sequence/Unknown Organism
tggccgcctc tgtcgaagaa g

SEQ ID NO: 16. 4D1 VH Nuoleotide sequence
caggtccaac tgcagcagcc tggggctgag cttgtgaagc ctggggcttc agtgaacctg tcctgtaagg cttctggcta caccttcacc agctactgga tgcactgggt gaagcagagg cctggacaag gccttgagtg gatcggagag attgatcctt ctgatagttt tactacctac aatcaaaaact tcaaagacag gccacattg actgtagaca atcatccag cacagcctac atgcagctca gaagtctgac atctgaggac tctgcggtct attactgtgc caggggggt ccaggagact ttcgctatgc tatggattac tggggccaag gcacctcggt caccgtctcc tca SEQ ID NO: 17 - 4D1 VH Amino Acid sequence
Gln Val Gln Leu Gln Gln Pro Gly Ala Glu Leu Val Lys Pro Gly Ala
1               5                   10                  15
```

```
                            -continued
Ser Val Asn Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Asp Ser Phe Thr Thr Tyr Asn Gln Asn Phe
        50                  55                  60

Lys Asp Arg Ala Thr Leu Thr Val Asp Lys Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Gly Gly Pro Gly Asp Phe Arg Tyr Ala Met Asp Tyr Trp Gly
            100                 105                 110

Gln Gly Thr Ser Val Thr Val Ser Ser
        115                 120

SEQ ID NO: 18 - 4D1 VK Nuciectide sequence
gacatcctga tgacccaatc tccatcctcc atgtctgtat ctctgggaga cacagtcagc atcacttgcc atgcaagtca gggcattagc agtaacatag gtggttgca gcagaaacca gggaaatcat tcaagggcct gatctatcat ggaaccaact tggaagatgg agttccatca aggttcagtg gcagtggatc tggagcagat tattctctca ccatcagcag cctggaatcc gaagactttg cagactatta ctgtgtacag tatgttcagt ttccctacac gttcggaggg gggaccaagc tggaaataaa acgggct SEQ ID NO: 19 - 4D1 Vk Amino Acid sequence
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
                20                  25                  30

Ile Gly Trp Leu Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Val Gln Phe Pro Tyr
                85                  90                  95

Thr Phe Gly Gly Gly Thr Lys Leu Glu Ile Lys Arg Ala
            100                 105

SEQ ID NO: 20 - 3G4 VH Nucleotide sequence
caggtccaac tgcagcagtc tggggctgag ctggtgaggc ctggggtctc agtgaagatt tcctgcaagg gttctggcta cacattcact gattatgcta tgcattgggt gaagcagagt catgcaaaga gtctagagtg gattggactt attaatactg actatggtga ctactactac aaccagaagt tcaagggcaa ggccacaatg actgtagaca atcctccaa cacagcctat atggaacttg ccagactgac atctgaggat tctgccatct attactgtgc aagatcggac tatgattact atttctgtgg tatggactac tggggtcaag gaaccacggt caccgaatct cta SEQ ID NO: 21 - 3G4 VH Amino Acid sequence
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45
```

```
Gly Leu Ile Asn Thr Asp Tyr Gly Asp Thr Thr Tyr Asn Gln Lys Phe
        50                  55                  60
Lys Gly Lys Ala Thr Met Thr Val Asp Lys Ser Ser Asn Thr Ala Tyr
 65                  70                  75                  80
Met Glu Leu Ala Arg Leu Thr Ser Glu Asp Ser Ala Ile Tyr Tyr Cys
                 85                  90                  95
Ala Arg Ser Asp Tyr Asp Tyr Tyr Phe Cys Gly Met Asp Tyr Trp Gly
                100                 105                 110
Gln Gly Thr Thr Val Thr Glu Ser Leu
            115                 120

SEQ ID NO: 22 - 2F2 VH Nucleotide sequence
caggtgcagc tgaaggagtc aggacctggc ctggtggcgc cctcacagcg cctgtccatc acatgcaccg tctcagggtt ctcattaacc ggctatggtg tacactggat tcgccagtct ccaggaaagg gtctggagtg gctgggaatg atatgggctg agggaagaac cgactataat tcagttctca atccagact gagcatcaat aaggacaatt ccaggagcca agtttctta gaaatgaaca gtctgcaaac tgatgacaca gccaggtact actgtgccag agaggtgatt actacggaag cctggtactt cgatgtctgg ggccaaggaa cctcggtcac cgaatct SEQ ID NO: 23 - 2F2 VH Amino Acid sequence
Gln Val Gln Leu Lys Glu Ser Gly Pro Gly Leu Val Ala Pro Ser Gln
 1               5                  10                  15
Arg Leu Ser Ile Thr Cys Thr Val Ser Gly Phe Ser Leu Thr Gly Tyr
                 20                  25                  30
Gly Val His Trp Ile Arg Gln Ser Pro Gly Lys Gly Leu Glu Trp Leu
             35                  40                  45
Gly Met Ile Trp Ala Glu Gly Arg Thr Asp Tyr Asn Ser Val Leu Lys
        50                  55                  60
Ser Arg Leu Ser Ile Asn Lys Asp Asn Ser Arg Ser Gln Val Phe Leu
 65                  70                  75                  80
Glu Met Asn Ser Leu Gln Thr Asp Asp Thr Ala Arg Tyr Tyr Cys Ala
                 85                  90                  95
Arg Glu Val Ile Thr Thr Glu Ala Trp Tyr Phe Asp Val Trp Gly Gln
                100                 105                 110
Gly Thr Ser Val Thr Glu Ser
            115

SEQ ID NO: 24 - 2F2 VK Nucleotide sequence
gacattgtga tgactcagtc tccagccacc ctgtctgtga ctccaggaga tagagtctct ctttcctgca gggccagcca gagtattagc gactacttat actggtatca acaaaaatca catgagtctc caaggcttct catcaaatat gcttcccaat ccatctctgg gatcccctcc agattcagtg gcagtggatc agggtcagat ttcactctca ctatcaacag tgtggaacct gaagatgttg gaatgtatta ctgtcaaaat ggtcacacct ttccgctcac gttcggtgct ggcaccaagc tggaaatcaa acgg SEQ ID NO: 25 - 2F2 VK Amino Acid seqnence
Asp Ile Val Met Thr Gln Ser Pro Ala Thr Leu Ser Val Thr Pro Gly
 1               5                  10                  15
Asp Arg Val Ser Leu Ser Cys Arg Ala Ser Gln Ser Ile Ser Asp Tyr
                 20                  25                  30
Leu Tyr Trp Tyr Gln Gln Lys Ser His Glu Ser Pro Arg Leu Leu Ile
             35                  40                  45
Lys Tyr Ala Ser Gln Ser Ile Ser Gly Ile Pro Ser Arg Phe Ser Gly
        50                  55                  60
Ser Gly Ser Gly Ser Asp Phe Thr Leu Thr Ile Asn Ser Val Glu Pro
 65                  70                  75                  80
```

Glu Asp Val Gly Met Tyr Tyr Cys Gln Asn Gly His Thr Phe Pro Leu
                85                  90                  95

Thr Phe Gly Ala Gly Thr Lys Leu Glu Ile Lys Arg.

---

What is claimed:

1. A kit for detecting analytes comprising:
   (a) a lateral flow test device comprising a bibulous strip and an upstream chamber having at least one compartment containing a releasable wash buffer, the bibulous strip comprising:
      (i) a sample application zone,
      (ii) a detection zone comprising one or more discrete oligonucleotide bands non-diffusively bound to said strip, and
      (iii) a control zone; and
   (b) a sample collection device independent of said test device, the sample collection device housing reagents for an immunoassay, the reagents comprising a first conjugate and a second conjugate for each of said analytes;
      (i) each said first conjugate comprising a specific binding partner for its analyte, and an oligonucleotide having a sequence complementary to an oligonucleotide of one of said discrete bands; and
      (ii) each said second conjugate comprising a specific binding partner for its analyte, and a label.

2. The kit of claim 1, wherein the oligonucleotides are pRNAs.

3. The kit of claim 2, wherein the test device comprises from 3 to 7 discrete bands of pRNA, the pRNA in each band having a different sequence.

4. The kit of claim 1, wherein the test device further comprises a mechanism to release the wash buffer by puncturing, depressing, or breaking the compartment for the wash buffer.

5. The kit of claim 4, wherein the compartment comprises a soft membrane or ampoule.

6. The kit of claim 1, wherein the sample collection device comprises the first and second conjugates in a first sealed chamber, and further comprises a sample extraction buffer in a second chamber.

7. The kit of claim 6, wherein the extraction buffer is releasable, so as to allow fluid communication between the first chamber and the second chamber.

8. The kit of claim 1, wherein the first and second conjugates are in dried solid form.

9. The kit of claim 8, wherein the first and second conjugates are in the form of lyophilized pellets.

10. The kit of claim 1, wherein the specific binding partners are independently selected from polyclonal and monoclonal antibodies.

11. The kit of claim 1, wherein the strip is treated with a blocking agent.

12. The kit of claim 1, wherein the control zone comprises an immobilized specific binding member for a labeled control reagent, the labeled control reagent being housed in said sample collection device.

13. The kit of claim 1, wherein the test device comprises an aperture or port to receive the sample collection device for application of sample.

14. The kit of claim 1, wherein the label is a particulate label.

15. The kit of claim 14, wherein the particulate label is colloidal gold.

16. The kit of claim 14, wherein the particulate label is a dyed or colored particle.

17. The kit of claim 14, wherein the label comprises a lanthanide metal.

18. The kit of claim 17, wherein the label is a fluorescent europium(III) chelate particle.

19. The kit of claim 18, further comprises a fluorescent reader.

20. The kit of claim 19, wherein the fluorescent reader comprises a lamp emitting UV A.

21. The kit of claim 19, wherein the fluorescent reader further comprises a hard standard.

22. The kit of claim 2, wherein at least one of the specific binding agent is specific to an infectious agent.

23. The kit of claim 22, wherein said infectious agent is selected from influenza virus, HIV, hepatitis virus, adenovirus, enterovirus, and parainfluenza virus.

24. The kit of claim 22, wherein the specific binding partners are specific for at least two different infectious agents.

25. The kit of claim 22, wherein the infectious agent are influenza viruses.

26. The kit of claim 25, wherein said influenza viruses are independently selected from influenza A, B, C.

27. The kit of claim 25, wherein said influenza viruses are influenza A, influenza B, a subtype of influenza A that is pandemic, and a subtype of influenza A that is non-pandemic.

28. The kit of claim 25 capable of detecting H1 and H3 influenza type A antigens.

29. The kit of claim 25 capable of detecting H1N1 or an H4 influenza.

* * * * *